US009402621B2

(12) United States Patent  (10) Patent No.: US 9,402,621 B2
Stone et al.  (45) Date of Patent: Aug. 2, 2016

(54) METHOD FOR TISSUE FIXATION

(71) Applicant: Biomet Sports Medicine, LLC, Warsaw, IN (US)

(72) Inventors: Kevin T. Stone, Winona Lake, IN (US); Gregory J. Denham, Warsaw, IN (US); Ryan Harper, Leesburg, IN (US)

(73) Assignee: Biomet Sports Medicine, LLC., Warsaw, IN (US)

( * ) Notice: Subject to any disclaimer, the term of this patent is extended or adjusted under 35 U.S.C. 154(b) by 641 days.

(21) Appl. No.: 13/625,413

(22) Filed: Sep. 24, 2012

(65) Prior Publication Data

US 2013/0023930 A1  Jan. 24, 2013

Related U.S. Application Data

(60) Division of application No. 12/489,181, filed on Jun. 22, 2009, now Pat. No. 8,298,262, which is a continuation-in-part of application No. 12/474,802, filed on May 29, 2009, now Pat. No. 8,088,130, and a (Continued)

(51) Int. Cl.
*A61B 17/04* (2006.01)
(52) U.S. Cl.
CPC ......... *A61B 17/0487* (2013.01); *A61B 17/0401* (2013.01); *A61B 2017/0404* (2013.01); *A61B 2017/044* (2013.01); *A61B 2017/0414* (2013.01); *A61B 2017/0432* (2013.01); *A61B 2017/0448* (2013.01); *A61B 2017/0458* (2013.01)

(58) Field of Classification Search
CPC ........... A61B 17/0401; A61B 17/0487; A61B 2017/0404; A61B 2017/0414; A61B 2017/0432; A61B 2017/044; A61B 2017/0448; A61B 2017/0458; A61B 2017/0409; A61B 2017/0496; A61B 2017/0446

See application file for complete search history.

(56) References Cited

U.S. PATENT DOCUMENTS

| 64,499 | A | 5/1867 | Daubert |
| 65,499 | A | 6/1867 | Miller |
| 126,366 | A | 4/1872 | Wills |
| 233,475 | A | 10/1880 | Cook et al. |
| 261,501 | A | 7/1882 | Vandermark |

(Continued)

FOREIGN PATENT DOCUMENTS

| AU | 4957264 | 3/1966 |
| AU | 440266 | 10/1967 |

(Continued)

OTHER PUBLICATIONS

"AperFix® System Surgical Technique Guide. Single Tunnel Double Bundle.™" Cayenne Medical brochure. (Aug. 2008) 8 sheets.

(Continued)

*Primary Examiner* — Dianne Dornbusch
(74) *Attorney, Agent, or Firm* — Schwegman Lundberg & Woessner, P.A.

(57) ABSTRACT

A method for securing a strand to a fixation member for arthroscopic fixation, wherein the fixation member includes a channel on an exterior surface and an aperture therethrough. The method includes passing a strand having first and second ends through a flexible sleeve, passing the sleeve through the aperture of the fixation member in a first direction, tensioning the strand, and pulling the sleeve in a second direction different than the first direction to secure the sleeve to the fixation member without tying the strand on the fixation member.

16 Claims, 20 Drawing Sheets

Related U.S. Application Data continuation-in-part of application No. 11/541,506, filed on Sep. 29, 2006, now Pat. No. 7,601,165, and a continuation-in-part of application No. 11/541,505, filed on Sep. 29, 2006, now Pat. No. 7,658,751, and a continuation-in-part of application No. 12/014,399, filed on Jan. 15, 2008, now Pat. No. 7,909,851, and a continuation-in-part of application No. 12/014,340, filed on Jan. 15, 2008, now Pat. No. 7,905,904, and a continuation-in-part of application No. 11/935,681, filed on Nov. 6, 2007, now Pat. No. 7,905,903, and a continuation-in-part of application No. 11/869,440, filed on Oct. 9, 2007, now Pat. No. 7,857,830, and a continuation-in-part of application No. 11/784,821, filed on Apr. 10, 2007, now Pat. No. 9,017,381, and a continuation-in-part of application No. 11/347,661, filed on Feb. 3, 2006, now Pat. No. 7,749,250, and a continuation-in-part of application No. 11/347,662, filed on Feb. 3, 2006, now abandoned, application No. 13/625,413, which is a division of application No. 13/412,116, filed on Mar. 5, 2012, now Pat. No. 8,771,316, which is a continuation-in-part of application No. 12/196,405, filed on Aug. 22, 2008, now Pat. No. 8,128,658, and a continuation-in-part of application No. 12/196,407, filed on Aug. 22, 2008, now Pat. No. 8,137,382, and a continuation-in-part of application No. 12/196,410, filed on Aug. 22, 2008, now Pat. No. 8,118,836.

(56) References Cited

U.S. PATENT DOCUMENTS

| | | | |
|---|---|---|---|
| 268,407 | A | 12/1882 | Hughes |
| 330,087 | A | 11/1885 | Binns |
| 394,739 | A | 12/1888 | Toulmin |
| 401,677 | A | 4/1889 | Autenrieth |
| 417,805 | A | 12/1889 | Beaman |
| 445,875 | A | 2/1891 | Brickell |
| 487,304 | A | 12/1892 | Todd |
| 762,710 | A | 6/1901 | Hall |
| 837,767 | A | 12/1906 | Aims |
| 838,203 | A | 12/1906 | Neil |
| 1,059,631 | A | 4/1913 | Popovics |
| 1,131,155 | A | 3/1915 | Murphy |
| 1,153,450 | A | 9/1915 | Schaff |
| 1,346,940 | A | 7/1920 | Collins |
| 1,635,066 | A | 7/1927 | Wells |
| 1,950,799 | A | 3/1934 | Jones |
| 2,065,659 | A | 12/1936 | Cullen |
| 2,108,206 | A | 2/1938 | Meeker |
| 2,121,193 | A | 6/1938 | Hanicke |
| 2,242,003 | A | 5/1941 | Lorenzo |
| 2,267,925 | A | 12/1941 | Johnston |
| 2,302,986 | A | 11/1942 | Vollrath |
| 2,329,398 | A | 9/1943 | Duffy |
| 2,379,629 | A | 7/1945 | Eweson |
| 2,397,216 | A | 3/1946 | Stellin |
| RE22,857 | E | 3/1947 | Ogburn |
| 2,526,959 | A | 10/1950 | Lorenzo |
| 2,528,456 | A | 10/1950 | Stevenson |
| 2,562,419 | A | 7/1951 | Ferris |
| 2,581,564 | A | 1/1952 | Villegas |
| 2,600,395 | A | 6/1952 | Domoj et al. |
| 2,610,631 | A | 9/1952 | Calicchio |
| 2,665,597 | A | 1/1954 | J.L. Hill |
| 2,669,774 | A | 2/1954 | Mitchell |
| 2,698,986 | A | 1/1955 | Brown |
| 2,760,488 | A | 8/1956 | Pierce |
| 2,833,284 | A | 5/1958 | Springer |
| 2,846,712 | A | 8/1958 | Markman |
| 2,860,393 | A | 11/1958 | Brock |
| 2,880,728 | A | 4/1959 | Rights |
| 2,881,762 | A | 4/1959 | Lowrie |
| 2,883,096 | A | 4/1959 | Dawson |
| 2,913,042 | A | 11/1959 | Taylor |
| 3,000,009 | A | 9/1961 | Selstad |
| 3,003,155 | A | 10/1961 | Mielzynski et al. |
| 3,013,559 | A | 12/1961 | Thomas |
| 3,037,619 | A | 6/1962 | Stevans |
| 3,039,460 | A | 6/1962 | Chandler |
| 3,081,781 | A | 3/1963 | Stermer |
| 3,090,386 | A | 5/1963 | Curtis |
| 3,103,666 | A | 9/1963 | Bone |
| 3,123,077 | A | 3/1964 | Alcamo |
| 3,125,095 | A | 3/1964 | Kaufman et al. |
| 3,209,422 | A | 10/1965 | Dritz |
| 3,223,083 | A | 12/1965 | Cobey |
| 3,234,938 | A | 2/1966 | Robinson |
| 3,240,379 | A | 3/1966 | Bremer et al. |
| 3,250,271 | A | 5/1966 | Lippes |
| 3,399,432 | A | 9/1968 | Merser |
| 3,409,014 | A | 11/1968 | Shannon |
| RE26,501 | E | 12/1968 | Himmelstein et al. |
| 3,435,475 | A | 4/1969 | Bisk |
| 3,467,089 | A | 9/1969 | Hasson |
| 3,470,834 | A | 10/1969 | Bone |
| 3,470,875 | A | 10/1969 | Johnson |
| 3,500,820 | A | 3/1970 | Almen |
| 3,507,274 | A | 4/1970 | Soichet |
| 3,513,484 | A | 5/1970 | Hausner |
| 3,515,132 | A | 6/1970 | McKnight |
| 3,522,803 | A | 8/1970 | Majzlin |
| 3,527,223 | A | 9/1970 | Shein |
| 3,533,406 | A | 10/1970 | Hutterer et al. |
| 3,541,591 | A | 11/1970 | Hoegerman |
| 3,547,389 | A | 12/1970 | Mitchell |
| 3,579,831 | A | 5/1971 | Stevens et al. |
| 3,590,616 | A | 7/1971 | Schussler et al. |
| 3,608,095 | A | 9/1971 | Barry |
| 3,618,447 | A | 11/1971 | Goins |
| 3,628,530 | A | 12/1971 | Schwartz |
| 3,643,649 | A | 2/1972 | Amato |
| 3,648,705 | A | 3/1972 | Lary |
| 3,650,274 | A | 3/1972 | Edwards et al. |
| 3,656,483 | A | 4/1972 | Rudel |
| 3,659,597 | A | 5/1972 | Wolfers |
| 3,664,345 | A | 5/1972 | Dabbs et al. |
| 3,665,560 | A | 5/1972 | Bennett et al. |
| 3,675,639 | A | 7/1972 | Cimber |
| 3,683,422 | A | 8/1972 | Stemmer et al. |
| 3,692,022 | A | 9/1972 | Ewing |
| 3,695,271 | A | 10/1972 | Chodorow |
| 3,699,969 | A | 10/1972 | Allen |
| 3,716,058 | A | 2/1973 | Tanner, Jr. |
| 3,744,488 | A | 7/1973 | Cox |
| 3,752,516 | A | 8/1973 | Mumma |
| 3,757,629 | A | 9/1973 | Schneider |
| 3,763,856 | A | 10/1973 | Blomberg |
| 3,771,520 | A | 11/1973 | Lerner |
| 3,777,748 | A | 12/1973 | Abramson |
| 3,786,801 | A | 1/1974 | Sartorius |
| 3,807,407 | A | 4/1974 | Schweizer |
| 3,810,456 | A | 5/1974 | Karman |
| 3,825,010 | A | 7/1974 | McDonald |
| 3,840,017 | A | 10/1974 | Violante et al. |
| 3,842,824 | A | 10/1974 | Neufeld |
| 3,842,840 | A | 10/1974 | Schweizer |
| 3,845,772 | A | 11/1974 | Smith |
| 3,867,933 | A | 2/1975 | Kitrilakis |
| 3,867,944 | A | 2/1975 | Samuels |
| 3,871,368 | A | 3/1975 | Johnson et al. |
| 3,871,379 | A | 3/1975 | Clarke |
| 3,874,388 | A | 4/1975 | King et al. |
| 3,875,648 | A | 4/1975 | Bone |
| 3,877,570 | A | 4/1975 | Barry |
| 3,880,156 | A | 4/1975 | Hoff |
| 3,881,475 | A | 5/1975 | Gordon et al. |
| 3,889,666 | A | 6/1975 | Lerner |
| 3,892,240 | A | 7/1975 | Park |
| 3,896,500 | A | 7/1975 | Rambert et al. |

(56) References Cited

U.S. PATENT DOCUMENTS

| | | | |
|---|---|---|---|
| 3,896,810 A | 7/1975 | Akiyama |
| 3,907,442 A | 9/1975 | Reid |
| 3,910,281 A | 10/1975 | Kletschka et al. |
| 3,918,444 A | 11/1975 | Hoff et al. |
| 3,918,455 A | 11/1975 | Coplan |
| 3,927,666 A | 12/1975 | Hoff |
| 3,931,667 A | 1/1976 | Merser et al. |
| 3,933,153 A | 1/1976 | Csatary et al. |
| 3,937,217 A | 2/1976 | Kosonen et al. |
| 3,943,932 A | 3/1976 | Woo |
| 3,946,446 A | 3/1976 | Schofield |
| 3,946,728 A | 3/1976 | Bettex |
| 3,946,740 A | 3/1976 | Bassett |
| 3,953,896 A | 5/1976 | Treace |
| 3,954,103 A | 5/1976 | Garcia-Roel et al. |
| 3,961,632 A | 6/1976 | Moossun |
| 3,973,560 A | 8/1976 | Emmett et al. |
| 3,976,079 A | 8/1976 | Samuels et al. |
| 3,977,050 A | 8/1976 | Perez et al. |
| 3,979,799 A | 9/1976 | Merser et al. |
| 3,985,138 A | 10/1976 | Jarvik |
| 3,990,619 A | 11/1976 | Russell |
| 4,005,707 A | 2/1977 | Moulding, Jr. |
| 4,006,747 A | 2/1977 | Kronenthal et al. |
| 4,007,743 A | 2/1977 | Blake |
| 4,013,071 A | 3/1977 | Rosenberg et al. |
| 4,026,281 A | 5/1977 | Mayberry et al. |
| 4,036,101 A | 7/1977 | Burnett |
| 4,050,100 A | 9/1977 | Barry |
| 4,054,954 A | 10/1977 | Nakayama et al. |
| 4,084,478 A | 4/1978 | Simmons |
| 4,085,466 A | 4/1978 | Goodfellow et al. |
| 4,094,313 A | 6/1978 | Komamura et al. |
| 4,099,750 A | 7/1978 | McGrew |
| 4,103,690 A | 8/1978 | Harris |
| RE29,819 E | 10/1978 | Bone |
| 4,121,487 A | 10/1978 | Bone |
| 4,143,656 A | 3/1979 | Holmes et al. |
| 4,144,876 A | 3/1979 | DeLeo |
| 4,146,022 A | 3/1979 | Johnson et al. |
| 4,149,277 A | 4/1979 | Bokros |
| 4,157,714 A | 6/1979 | Foltz et al. |
| 4,158,250 A | 6/1979 | Ringwald |
| 4,160,453 A | 7/1979 | Miller |
| 4,164,225 A | 8/1979 | Johnson et al. |
| 4,172,458 A | 10/1979 | Pereyra |
| 4,175,555 A | 11/1979 | Herbert |
| 4,185,636 A | 1/1980 | Gabbay et al. |
| 4,196,883 A | 4/1980 | Einhorn et al. |
| 4,207,627 A | 6/1980 | Cloutier |
| 4,210,148 A | 7/1980 | Stivala |
| 4,235,161 A | 11/1980 | Kunreuther |
| 4,235,238 A | 11/1980 | Ogiu et al. |
| 4,237,779 A | 12/1980 | Kunreuther |
| 4,243,037 A | 1/1981 | Smith |
| 4,249,525 A | 2/1981 | Krzeminski |
| 4,263,913 A | 4/1981 | Malmin |
| 4,265,246 A | 5/1981 | Barry |
| 4,273,117 A | 6/1981 | Neuhauser et al. |
| 4,275,490 A | 6/1981 | Bivins |
| 4,275,717 A | 6/1981 | Bolesky |
| 4,287,807 A | 9/1981 | Pacharis et al. |
| 4,291,698 A | 9/1981 | Fuchs et al. |
| 4,301,551 A | 11/1981 | Dore et al. |
| 4,307,723 A | 12/1981 | Finney |
| 4,312,337 A | 1/1982 | Donohue |
| 4,316,469 A | 2/1982 | Kapitanov et al. |
| 4,326,531 A | 4/1982 | Shimonaka et al. |
| 4,344,193 A | 8/1982 | Kenny |
| 4,345,601 A | 8/1982 | Fukuda |
| 4,349,027 A | 9/1982 | DiFrancesco |
| 4,388,921 A | 6/1983 | Sutter et al. |
| 4,400,833 A | 8/1983 | Kurland |
| 4,402,445 A | 9/1983 | Green |
| 4,409,974 A | 10/1983 | Freedland |
| 4,438,769 A | 3/1984 | Pratt et al. |
| 4,441,489 A | 4/1984 | Evans et al. |
| 4,454,875 A | 6/1984 | Pratt et al. |
| 4,462,395 A | 7/1984 | Johnson |
| 4,463,753 A | 8/1984 | Gustilo |
| 4,473,102 A | 9/1984 | Ohman et al. |
| 4,484,570 A | 11/1984 | Sutter et al. |
| 4,489,446 A | 12/1984 | Reed |
| 4,489,464 A | 12/1984 | Massari et al. |
| 4,493,323 A | 1/1985 | Albright et al. |
| 4,496,468 A | 1/1985 | House et al. |
| 4,505,274 A | 3/1985 | Speelman |
| 4,509,516 A | 4/1985 | Richmond |
| 4,531,522 A | 7/1985 | Bedi et al. |
| 4,532,926 A | 8/1985 | O'Holla |
| 4,534,350 A | 8/1985 | Golden et al. |
| 4,535,764 A | 8/1985 | Ebert |
| 4,537,185 A | 8/1985 | Stednitz |
| 4,549,545 A | 10/1985 | Levy |
| 4,549,652 A | 10/1985 | Free |
| 4,561,432 A | 12/1985 | Mazor |
| 4,564,007 A | 1/1986 | Coombs et al. |
| 4,570,623 A | 2/1986 | Ellison et al. |
| 4,573,844 A | 3/1986 | Smith |
| 4,576,608 A | 3/1986 | Homsy |
| 4,584,722 A | 4/1986 | Levy et al. |
| 4,587,963 A | 5/1986 | Leibinger et al. |
| 4,590,928 A | 5/1986 | Hunt et al. |
| 4,595,007 A | 6/1986 | Mericle |
| 4,596,249 A | 6/1986 | Freda et al. |
| 4,597,766 A | 7/1986 | Hilal et al. |
| 4,602,635 A | 7/1986 | Mulhollan et al. |
| 4,602,636 A | 7/1986 | Noiles |
| 4,604,997 A | 8/1986 | De Bastiani et al. |
| 4,605,414 A | 8/1986 | Czajka |
| 4,616,650 A | 10/1986 | Green et al. |
| 4,621,640 A | 11/1986 | Mulhollan et al. |
| 4,624,254 A | 11/1986 | McGarry et al. |
| 4,632,100 A | 12/1986 | Somers et al. |
| 4,635,637 A | 1/1987 | Schreiber |
| 4,636,121 A | 1/1987 | Miller |
| 4,641,652 A | 2/1987 | Hutterer et al. |
| 4,649,916 A | 3/1987 | Frimberger |
| 4,649,952 A | 3/1987 | Jobe |
| 4,653,486 A | 3/1987 | Coker |
| 4,653,487 A | 3/1987 | Maale |
| 4,653,489 A | 3/1987 | Tronzo |
| 4,655,777 A | 4/1987 | Dunn et al. |
| 4,662,068 A | 5/1987 | Polonsky |
| 4,667,662 A | 5/1987 | Titone et al. |
| 4,667,675 A | 5/1987 | Davis |
| 4,669,473 A | 6/1987 | Richards et al. |
| 4,683,895 A | 8/1987 | Pohndorf |
| 4,688,561 A | 8/1987 | Reese |
| 4,690,169 A | 9/1987 | Jobe |
| 4,696,300 A | 9/1987 | Anderson |
| 4,705,040 A | 11/1987 | Mueller et al. |
| 4,708,132 A | 11/1987 | Silvestrini |
| 4,714,475 A | 12/1987 | Grundei et al. |
| 4,716,893 A | 1/1988 | Fischer et al. |
| 4,719,671 A | 1/1988 | Ito et al. |
| 4,719,917 A | 1/1988 | Barrows et al. |
| 4,723,540 A | 2/1988 | Gilmer, Jr. |
| 4,724,839 A | 2/1988 | Bedi et al. |
| 4,728,332 A | 3/1988 | Albrektsson |
| 4,736,746 A | 4/1988 | Anderson |
| 4,738,255 A | 4/1988 | Goble et al. |
| 4,739,751 A | 4/1988 | Sapega et al. |
| 4,741,330 A | 5/1988 | Hayhurst |
| 4,741,336 A | 5/1988 | Failla et al. |
| 4,744,353 A | 5/1988 | McFarland |
| 4,744,793 A | 5/1988 | Parr et al. |
| 4,750,492 A | 6/1988 | Jacobs |
| 4,751,922 A | 6/1988 | Dipietropolo |
| 4,760,843 A | 8/1988 | Fischer et al. |
| 4,760,844 A | 8/1988 | Kyle |
| 4,760,848 A | 8/1988 | Hasson |
| 4,770,663 A | 9/1988 | Hanslik et al. |
| 4,772,261 A | 9/1988 | Von Hoff et al. |

(56) References Cited

U.S. PATENT DOCUMENTS

| | | |
|---|---|---|
| 4,772,286 A | 9/1988 | Goble et al. |
| 4,773,910 A | 9/1988 | Chen et al. |
| 4,775,380 A | 10/1988 | Seedhom et al. |
| 4,776,328 A | 10/1988 | Frey et al. |
| 4,781,190 A | 11/1988 | Lee |
| 4,784,126 A | 11/1988 | Hourahane |
| 4,787,882 A | 11/1988 | Claren |
| 4,790,297 A | 12/1988 | Luque |
| 4,790,850 A | 12/1988 | Dunn et al. |
| 4,793,363 A | 12/1988 | Ausherman et al. |
| 4,809,695 A | 3/1989 | Gwathmey et al. |
| 4,813,406 A | 3/1989 | Ogle, II |
| 4,823,780 A | 4/1989 | Odensten et al. |
| 4,823,794 A | 4/1989 | Pierce |
| 4,828,562 A | 5/1989 | Kenna |
| 4,832,026 A | 5/1989 | Jones |
| 4,834,098 A | 5/1989 | Jones |
| 4,838,282 A | 6/1989 | Strasser et al. |
| 4,841,960 A | 6/1989 | Garner |
| 4,846,835 A | 7/1989 | Grande |
| 4,851,005 A | 7/1989 | Hunt et al. |
| 4,858,601 A | 8/1989 | Glisson |
| 4,858,603 A | 8/1989 | Clemow et al. |
| 4,858,608 A | 8/1989 | McQuilkin et al. |
| 4,860,513 A | 8/1989 | Whitman |
| 4,863,383 A | 9/1989 | Grafelmann et al. |
| 4,870,957 A | 10/1989 | Goble et al. |
| 4,872,450 A | 10/1989 | Austad |
| 4,873,976 A | 10/1989 | Schreiber |
| 4,884,572 A | 12/1989 | Bays et al. |
| 4,887,601 A | 12/1989 | Richards |
| 4,889,110 A | 12/1989 | Galline et al. |
| 4,890,615 A | 1/1990 | Caspari et al. |
| 4,893,619 A | 1/1990 | Dale et al. |
| 4,893,974 A | 1/1990 | Fischer et al. |
| 4,895,148 A | 1/1990 | Bays et al. |
| 4,896,668 A | 1/1990 | Popoff et al. |
| 4,898,156 A | 2/1990 | Gatturna et al. |
| 4,899,743 A | 2/1990 | Nicholson et al. |
| 4,901,721 A | 2/1990 | Hakki |
| 4,919,667 A | 4/1990 | Richmond |
| 4,922,897 A | 5/1990 | Sapega et al. |
| 4,923,461 A | 5/1990 | Caspari et al. |
| 4,927,421 A | 5/1990 | Goble et al. |
| 4,946,377 A | 8/1990 | Kovach |
| 4,946,468 A | 8/1990 | Li |
| 4,950,270 A | 8/1990 | Bowman et al. |
| 4,950,285 A | 8/1990 | Wilk |
| 4,960,381 A | 10/1990 | Niznick |
| 4,961,741 A | 10/1990 | Hayhurst |
| 4,968,315 A | 11/1990 | Gatturna |
| 4,968,317 A | 11/1990 | Tormala et al. |
| 4,969,886 A | 11/1990 | Cziffer et al. |
| 4,974,488 A | 12/1990 | Spralja |
| 4,976,736 A | 12/1990 | White et al. |
| 4,978,350 A | 12/1990 | Wagenknecht et al. |
| 4,979,956 A | 12/1990 | Silvestrini |
| 4,983,176 A | 1/1991 | Cushman et al. |
| 4,988,351 A | 1/1991 | Paulos et al. |
| 4,994,074 A | 2/1991 | Bezwada et al. |
| 4,997,433 A | 3/1991 | Goble et al. |
| 5,002,545 A | 3/1991 | Whiteside et al. |
| 5,002,550 A | 3/1991 | Li |
| 5,002,562 A | 3/1991 | Oberlander |
| 5,002,574 A | 3/1991 | May et al. |
| 5,007,921 A | 4/1991 | Brown |
| 5,020,713 A | 6/1991 | Kunreuther |
| 5,030,224 A | 7/1991 | Wright et al. |
| 5,030,235 A | 7/1991 | Campbell, Jr. |
| 5,035,701 A | 7/1991 | Kabbara |
| 5,037,422 A | 8/1991 | Hayhurst et al. |
| 5,037,426 A | 8/1991 | Goble et al. |
| 5,041,129 A | 8/1991 | Hayhurst et al. |
| 5,046,513 A | 9/1991 | Gatturna et al. |
| 5,047,030 A | 9/1991 | Draenert et al. |
| 5,053,046 A | 10/1991 | Janese |
| 5,053,047 A | 10/1991 | Yoon |
| 5,059,201 A | 10/1991 | Asnis |
| 5,059,206 A | 10/1991 | Winters |
| 5,061,277 A | 10/1991 | Carpentier et al. |
| 5,062,344 A | 11/1991 | Gerker |
| 5,062,843 A | 11/1991 | Mahony, III |
| 5,064,431 A | 11/1991 | Gilbertson et al. |
| 5,067,962 A | 11/1991 | Campbell et al. |
| 5,071,420 A | 12/1991 | Paulos et al. |
| 5,074,874 A | 12/1991 | Yoon et al. |
| 5,078,731 A | 1/1992 | Hayhurst |
| 5,078,843 A | 1/1992 | Pratt |
| 5,080,050 A | 1/1992 | Dale |
| 5,084,050 A | 1/1992 | Draenert |
| 5,084,058 A | 1/1992 | Li |
| 5,085,661 A | 2/1992 | Moss |
| 5,087,263 A | 2/1992 | Li |
| 5,087,309 A | 2/1992 | Melton, Jr. |
| 5,089,012 A | 2/1992 | Prou |
| 5,092,866 A | 3/1992 | Breard et al. |
| 5,098,435 A | 3/1992 | Stednitz et al. |
| 5,100,415 A | 3/1992 | Hayhurst |
| 5,100,417 A | 3/1992 | Cerier et al. |
| 5,108,433 A | 4/1992 | May et al. |
| 5,112,335 A | 5/1992 | Laboureau et al. |
| 5,116,337 A | 5/1992 | Johnson |
| 5,116,373 A | 5/1992 | Jakob et al. |
| 5,116,375 A | 5/1992 | Hofmann |
| 5,123,913 A | 6/1992 | Wilk et al. |
| 5,123,914 A | 6/1992 | Cope |
| 5,127,785 A | 7/1992 | Faucher et al. |
| 5,129,901 A | 7/1992 | Decoste |
| 5,129,902 A | 7/1992 | Goble et al. |
| 5,129,904 A | 7/1992 | Illi et al. |
| 5,129,906 A | 7/1992 | Ross et al. |
| 5,139,498 A | 8/1992 | Astudillo Ley |
| 5,139,499 A | 8/1992 | Small et al. |
| 5,139,520 A | 8/1992 | Rosenberg |
| 5,143,498 A | 9/1992 | Whitman |
| 5,147,362 A | 9/1992 | Goble |
| 5,149,329 A | 9/1992 | Richardson |
| 5,151,104 A | 9/1992 | Kenna |
| 5,152,790 A | 10/1992 | Rosenberg et al. |
| 5,154,189 A | 10/1992 | Oberlander |
| 5,156,616 A | 10/1992 | Meadows et al. |
| 5,163,960 A | 11/1992 | Bonutti |
| D331,626 S | 12/1992 | Hayhurst et al. |
| 5,169,400 A | 12/1992 | Muhling et al. |
| 5,171,274 A | 12/1992 | Fluckiger et al. |
| 5,176,682 A | 1/1993 | Chow |
| 5,178,629 A | 1/1993 | Kammerer |
| 5,183,458 A | 2/1993 | Marx |
| 5,190,545 A | 3/1993 | Corsi et al. |
| 5,192,282 A | 3/1993 | Draenert et al. |
| 5,197,987 A | 3/1993 | Koch et al. |
| 5,199,135 A | 4/1993 | Gold |
| 5,203,784 A | 4/1993 | Ross et al. |
| 5,203,787 A | 4/1993 | Noblitt et al. |
| 5,207,679 A | 5/1993 | Li |
| 5,209,753 A | 5/1993 | Biedermann et al. |
| 5,209,805 A | 5/1993 | Spraggins |
| 5,211,647 A | 5/1993 | Schmieding |
| 5,211,650 A | 5/1993 | Noda |
| 5,214,987 A | 6/1993 | Fenton, Sr. |
| 5,219,359 A | 6/1993 | McQuilkin et al. |
| 5,222,976 A | 6/1993 | Yoon |
| 5,224,940 A | 7/1993 | Dann et al. |
| 5,224,946 A | 7/1993 | Hayhurst et al. |
| 5,226,914 A | 7/1993 | Caplan et al. |
| 5,230,699 A | 7/1993 | Grasinger |
| 5,232,436 A | 8/1993 | Janevski |
| 5,234,435 A | 8/1993 | Seagrave, Jr. |
| 5,235,238 A | 8/1993 | Nomura et al. |
| 5,236,445 A | 8/1993 | Hayhurst et al. |
| 5,236,461 A | 8/1993 | Forte |
| 5,242,447 A | 9/1993 | Borzone |
| 5,246,441 A | 9/1993 | Ross et al. |
| 5,249,899 A | 10/1993 | Wilson |

(56) References Cited

U.S. PATENT DOCUMENTS

| | | |
|---|---|---|
| 5,250,053 A | 10/1993 | Snyder |
| 5,258,015 A | 11/1993 | Li et al. |
| 5,258,016 A | 11/1993 | DiPoto et al. |
| 5,258,040 A | 11/1993 | Bruchman et al. |
| 5,261,908 A | 11/1993 | Campbell, Jr. |
| 5,268,001 A | 12/1993 | Nicholson et al. |
| 5,269,160 A | 12/1993 | Wood |
| 5,269,783 A | 12/1993 | Sander |
| 5,269,806 A | 12/1993 | Sardelis et al. |
| 5,269,809 A * | 12/1993 | Hayhurst et al. ............... 606/232 |
| 5,279,311 A | 1/1994 | Snyder |
| 5,281,422 A | 1/1994 | Badylak et al. |
| 5,282,809 A | 2/1994 | Kammerer et al. |
| 5,282,832 A | 2/1994 | Toso et al. |
| 5,282,867 A | 2/1994 | Mikhail |
| 5,282,868 A | 2/1994 | Bahler |
| 5,285,040 A | 2/1994 | Brandberg et al. |
| 5,290,217 A | 3/1994 | Campos |
| 5,290,243 A | 3/1994 | Chodorow et al. |
| 5,306,301 A | 4/1994 | Graf et al. |
| 5,312,410 A | 5/1994 | Miller et al. |
| 5,312,422 A | 5/1994 | Trott |
| 5,312,438 A | 5/1994 | Johnson |
| 5,314,429 A | 5/1994 | Goble |
| 5,318,566 A | 6/1994 | Miller |
| 5,318,575 A | 6/1994 | Chesterfield et al. |
| 5,318,577 A | 6/1994 | Li |
| 5,318,578 A | 6/1994 | Hasson |
| 5,320,115 A | 6/1994 | Kenna |
| 5,320,626 A | 6/1994 | Schmieding |
| 5,320,633 A | 6/1994 | Allen et al. |
| 5,324,308 A | 6/1994 | Pierce |
| 5,330,489 A | 7/1994 | Green et al. |
| 5,333,625 A | 8/1994 | Klein |
| 5,334,204 A | 8/1994 | Clewett et al. |
| 5,336,229 A | 8/1994 | Noda |
| 5,336,231 A | 8/1994 | Adair |
| 5,336,240 A | 8/1994 | Metzler et al. |
| 5,339,870 A | 8/1994 | Green et al. |
| 5,342,369 A | 8/1994 | Harryman, II |
| 5,346,462 A | 9/1994 | Barber |
| 5,350,380 A | 9/1994 | Goble et al. |
| RE34,762 E | 10/1994 | Goble et al. |
| 5,354,292 A | 10/1994 | Braeuer et al. |
| 5,354,298 A | 10/1994 | Lee et al. |
| 5,354,299 A | 10/1994 | Coleman |
| 5,356,412 A | 10/1994 | Golds et al. |
| 5,356,413 A | 10/1994 | Martins et al. |
| 5,356,417 A | 10/1994 | Golds |
| 5,358,511 A | 10/1994 | Gatturna et al. |
| 5,360,431 A | 11/1994 | Puno et al. |
| 5,362,294 A | 11/1994 | Seitzinger |
| 5,362,911 A | 11/1994 | Cevasco et al. |
| 5,364,400 A | 11/1994 | Rego, Jr. et al. |
| 5,366,461 A | 11/1994 | Blasnik |
| 5,368,599 A | 11/1994 | Hirsch et al. |
| 5,370,661 A | 12/1994 | Branch |
| 5,370,662 A | 12/1994 | Stone et al. |
| 5,372,146 A | 12/1994 | Branch |
| 5,372,604 A | 12/1994 | Trott |
| 5,372,821 A | 12/1994 | Badylak et al. |
| 5,374,268 A | 12/1994 | Sander |
| 5,374,269 A | 12/1994 | Rosenberg |
| 5,379,492 A | 1/1995 | Glesser |
| 5,383,878 A | 1/1995 | Roger et al. |
| 5,383,904 A | 1/1995 | Totakura et al. |
| 5,385,567 A | 1/1995 | Goble |
| 5,391,171 A | 2/1995 | Schmieding |
| 5,391,176 A | 2/1995 | de la Torre |
| 5,391,182 A | 2/1995 | Chin |
| 5,393,302 A | 2/1995 | Clark et al. |
| RE34,871 E | 3/1995 | McGuire et al. |
| 5,395,374 A | 3/1995 | Miller et al. |
| 5,397,356 A | 3/1995 | Goble et al. |
| 5,403,328 A | 4/1995 | Shallman |
| 5,403,329 A | 4/1995 | Hinchcliffe |
| 5,403,348 A * | 4/1995 | Bonutti ..................... 606/232 |
| 5,405,359 A | 4/1995 | Pierce |
| 5,411,550 A | 5/1995 | Herweck et al. |
| 5,415,658 A | 5/1995 | Kilpela et al. |
| 5,417,690 A | 5/1995 | Sennett et al. |
| 5,417,691 A | 5/1995 | Hayhurst |
| 5,417,698 A | 5/1995 | Green et al. |
| 5,417,712 A | 5/1995 | Whittaker et al. |
| 5,423,819 A | 6/1995 | Small et al. |
| 5,423,821 A | 6/1995 | Pasque |
| 5,423,823 A | 6/1995 | Schmieding |
| 5,423,824 A | 6/1995 | Akerfeldt et al. |
| 5,423,860 A | 6/1995 | Lizardi et al. |
| 5,425,733 A | 6/1995 | Schmieding |
| 5,425,766 A | 6/1995 | Bowald et al. |
| 5,433,751 A | 7/1995 | Christel et al. |
| 5,437,680 A | 8/1995 | Yoon |
| 5,437,685 A | 8/1995 | Blasnik |
| 5,439,684 A | 8/1995 | Prewett et al. |
| 5,441,508 A | 8/1995 | Gazielly et al. |
| 5,443,468 A | 8/1995 | Johnson |
| 5,443,482 A | 8/1995 | Stone et al. |
| 5,443,483 A | 8/1995 | Kirsch et al. |
| 5,443,509 A | 8/1995 | Boucher et al. |
| 5,445,833 A | 8/1995 | Badylak et al. |
| 5,447,512 A | 9/1995 | Wilson et al. |
| 5,449,361 A | 9/1995 | Preissman |
| 5,451,203 A | 9/1995 | Lamb |
| 5,454,811 A | 10/1995 | Huebner |
| 5,454,821 A | 10/1995 | Harm et al. |
| 5,456,685 A | 10/1995 | Huebner |
| 5,456,721 A | 10/1995 | Legrand |
| 5,456,722 A | 10/1995 | McLeod et al. |
| 5,458,601 A | 10/1995 | Young, Jr. et al. |
| 5,458,604 A | 10/1995 | Schmieding |
| 5,462,542 A | 10/1995 | Alesi, Jr. |
| 5,462,560 A | 10/1995 | Stevens |
| 5,464,426 A | 11/1995 | Bonutti |
| 5,464,427 A | 11/1995 | Curtis et al. |
| 5,464,440 A | 11/1995 | Johansson et al. |
| 5,466,237 A | 11/1995 | Byrd, III et al. |
| 5,467,786 A | 11/1995 | Allen et al. |
| 5,470,334 A | 11/1995 | Ross et al. |
| 5,470,337 A | 11/1995 | Moss |
| 5,470,338 A | 11/1995 | Whitfield et al. |
| 5,472,452 A | 12/1995 | Trott |
| 5,474,565 A | 12/1995 | Trott |
| 5,474,568 A | 12/1995 | Scott |
| 5,474,572 A | 12/1995 | Hayhurst |
| 5,476,465 A | 12/1995 | Preissman |
| 5,478,344 A | 12/1995 | Stone et al. |
| 5,478,345 A | 12/1995 | Stone et al. |
| 5,480,403 A | 1/1996 | Lee et al. |
| 5,480,406 A | 1/1996 | Nolan et al. |
| 5,484,442 A | 1/1996 | Melker et al. |
| 5,486,197 A | 1/1996 | Le et al. |
| 5,486,359 A | 1/1996 | Caplan et al. |
| 5,490,750 A | 2/1996 | Gundy |
| 5,495,974 A | 3/1996 | Deschenes et al. |
| 5,496,290 A | 3/1996 | Ackerman |
| 5,496,331 A | 3/1996 | Xu et al. |
| 5,496,348 A | 3/1996 | Bonutti |
| 5,498,302 A | 3/1996 | Davidson |
| 5,500,000 A | 3/1996 | Feagin et al. |
| 5,505,735 A | 4/1996 | Li |
| 5,505,736 A | 4/1996 | Reimels et al. |
| 5,507,754 A | 4/1996 | Green et al. |
| 5,520,691 A | 5/1996 | Branch |
| 5,520,694 A | 5/1996 | Dance et al. |
| 5,520,700 A | 5/1996 | Beyar et al. |
| 5,520,702 A | 5/1996 | Sauer et al. |
| 5,522,817 A | 6/1996 | Sander et al. |
| 5,522,820 A | 6/1996 | Caspari et al. |
| 5,522,843 A | 6/1996 | Zang |
| 5,522,844 A | 6/1996 | Johnson |
| 5,522,845 A | 6/1996 | Wenstrom, Jr. |
| 5,522,846 A | 6/1996 | Bonutti |
| 5,524,946 A | 6/1996 | Thompson |

(56) References Cited

U.S. PATENT DOCUMENTS

| | | |
|---|---|---|
| 5,527,321 A | 6/1996 | Hinchliffe |
| 5,527,342 A | 6/1996 | Pietrzak et al. |
| 5,527,343 A | 6/1996 | Bonutti |
| 5,531,759 A * | 7/1996 | Kensey et al. .......... 606/213 |
| 5,534,012 A | 7/1996 | Bonutti |
| 5,534,033 A | 7/1996 | Simpson |
| 5,536,270 A | 7/1996 | Songer et al. |
| 5,540,698 A | 7/1996 | Preissman |
| 5,540,703 A | 7/1996 | Barker, Jr. et al. |
| 5,540,718 A | 7/1996 | Bartlett |
| 5,545,168 A | 8/1996 | Burke |
| 5,545,178 A * | 8/1996 | Kensey et al. .......... 606/213 |
| 5,545,180 A | 8/1996 | Le et al. |
| 5,545,228 A | 8/1996 | Kambin |
| 5,549,613 A | 8/1996 | Goble et al. |
| 5,549,617 A | 8/1996 | Green et al. |
| 5,549,619 A | 8/1996 | Peters et al. |
| 5,549,630 A | 8/1996 | Bonutti |
| 5,549,631 A | 8/1996 | Bonutti |
| 5,562,664 A | 10/1996 | Durlacher et al. |
| 5,562,668 A | 10/1996 | Johnson |
| 5,562,669 A | 10/1996 | McGuire |
| 5,562,683 A | 10/1996 | Chan |
| 5,562,685 A | 10/1996 | Mollenauer et al. |
| 5,562,686 A | 10/1996 | Sauer et al. |
| 5,569,269 A | 10/1996 | Hart et al. |
| 5,569,305 A | 10/1996 | Bonutti |
| 5,570,706 A | 11/1996 | Howell |
| 5,571,090 A | 11/1996 | Sherts |
| 5,571,104 A | 11/1996 | Li |
| 5,571,139 A | 11/1996 | Jenkins, Jr. |
| 5,572,655 A | 11/1996 | Tuljapurkar et al. |
| 5,573,286 A | 11/1996 | Rogozinski |
| 5,573,542 A | 11/1996 | Stevens |
| 5,573,547 A | 11/1996 | LeVeen et al. |
| 5,573,548 A | 11/1996 | Nazre et al. |
| 5,577,299 A | 11/1996 | Thompson et al. |
| 5,578,057 A | 11/1996 | Wenstrom, Jr. |
| 5,584,695 A | 12/1996 | Lal Sachdeva et al. |
| 5,584,835 A | 12/1996 | Greenfield |
| 5,584,836 A | 12/1996 | Ballintyn et al. |
| 5,584,862 A | 12/1996 | Bonutti |
| 5,586,986 A | 12/1996 | Hinchliffe |
| 5,588,575 A | 12/1996 | Davignon |
| 5,591,180 A | 1/1997 | Hinchliffe |
| 5,591,181 A | 1/1997 | Stone et al. |
| 5,591,207 A | 1/1997 | Coleman |
| 5,593,407 A | 1/1997 | Reis et al. |
| 5,593,425 A | 1/1997 | Bonutti et al. |
| 5,601,557 A | 2/1997 | Hayhurst |
| 5,601,559 A | 2/1997 | Melker et al. |
| 5,601,571 A | 2/1997 | Moss |
| 5,603,716 A | 2/1997 | Morgan et al. |
| 5,607,429 A | 3/1997 | Hayano et al. |
| 5,607,430 A | 3/1997 | Bailey |
| 5,613,971 A | 3/1997 | Lower et al. |
| 5,618,290 A | 4/1997 | Toy et al. |
| 5,626,611 A | 5/1997 | Liu et al. |
| 5,626,614 A | 5/1997 | Hart |
| 5,628,756 A | 5/1997 | Barker, Jr. et al. |
| 5,628,766 A | 5/1997 | Johnson |
| 5,630,824 A | 5/1997 | Hart |
| 5,632,745 A | 5/1997 | Schwartz |
| 5,632,748 A | 5/1997 | Beck, Jr. et al. |
| 5,641,256 A | 6/1997 | Gundy |
| 5,643,266 A | 7/1997 | Li |
| 5,643,269 A | 7/1997 | Harle et al. |
| 5,643,273 A | 7/1997 | Clark |
| 5,643,295 A | 7/1997 | Yoon |
| 5,643,319 A | 7/1997 | Green et al. |
| 5,643,320 A | 7/1997 | Lower et al. |
| 5,643,321 A | 7/1997 | McDevitt |
| 5,645,546 A | 7/1997 | Fard |
| 5,645,547 A | 7/1997 | Coleman |
| 5,645,568 A | 7/1997 | Chervitz et al. |
| 5,645,588 A | 7/1997 | Graf et al. |
| 5,647,874 A | 7/1997 | Hayhurst |
| 5,649,959 A | 7/1997 | Hannam et al. |
| 5,649,960 A | 7/1997 | Pavletic |
| 5,649,963 A | 7/1997 | McDevitt |
| 5,658,289 A | 8/1997 | Boucher et al. |
| 5,658,299 A | 8/1997 | Hart |
| 5,658,313 A | 8/1997 | Thal |
| 5,662,658 A | 9/1997 | Wenstrom, Jr. |
| 5,662,663 A | 9/1997 | Shallman |
| 5,662,677 A | 9/1997 | Wimmer |
| 5,662,681 A | 9/1997 | Nash et al. |
| 5,665,112 A | 9/1997 | Thal |
| 5,667,513 A | 9/1997 | Torrie et al. |
| 5,671,695 A | 9/1997 | Schroeder |
| 5,674,224 A | 10/1997 | Howell et al. |
| 5,679,723 A | 10/1997 | Cooper et al. |
| 5,681,334 A | 10/1997 | Evans et al. |
| 5,681,352 A | 10/1997 | Clancy, III et al. |
| 5,683,404 A | 11/1997 | Johnson |
| 5,683,419 A | 11/1997 | Thal |
| 5,688,284 A | 11/1997 | Chervitz et al. |
| 5,688,285 A | 11/1997 | Yamada et al. |
| 5,690,655 A | 11/1997 | Hart et al. |
| 5,690,676 A | 11/1997 | DiPoto et al. |
| 5,690,678 A | 11/1997 | Johnson |
| 5,693,046 A | 12/1997 | Songer et al. |
| 5,695,497 A | 12/1997 | Stahelin et al. |
| 5,697,929 A | 12/1997 | Mellinger |
| 5,699,657 A | 12/1997 | Paulson |
| 5,702,397 A | 12/1997 | Goble et al. |
| 5,702,422 A | 12/1997 | Stone |
| 5,702,462 A | 12/1997 | Oberlander |
| 5,707,373 A | 1/1998 | Sevrain et al. |
| 5,709,708 A | 1/1998 | Thal |
| 5,711,969 A | 1/1998 | Patel et al. |
| 5,713,005 A | 1/1998 | Proebsting |
| 5,713,897 A | 2/1998 | Goble et al. |
| 5,713,904 A | 2/1998 | Errico et al. |
| 5,713,905 A | 2/1998 | Goble et al. |
| 5,713,921 A | 2/1998 | Bonutti |
| 5,715,578 A | 2/1998 | Knudson |
| 5,716,359 A | 2/1998 | Ojima et al. |
| 5,716,397 A | 2/1998 | Myers |
| 5,716,616 A | 2/1998 | Prockop et al. |
| 5,718,717 A | 2/1998 | Bonutti |
| 5,720,747 A | 2/1998 | Burke |
| 5,720,765 A | 2/1998 | Thal |
| 5,720,766 A | 2/1998 | Zang et al. |
| 5,722,976 A | 3/1998 | Brown |
| 5,723,331 A | 3/1998 | Tubo et al. |
| 5,725,529 A | 3/1998 | Nicholson et al. |
| 5,725,549 A | 3/1998 | Lam |
| 5,725,556 A | 3/1998 | Moser et al. |
| 5,725,557 A | 3/1998 | Gatturna et al. |
| 5,725,581 A | 3/1998 | Brånemark |
| 5,725,582 A | 3/1998 | Bevan et al. |
| 5,726,722 A | 3/1998 | Uehara et al. |
| 5,728,107 A | 3/1998 | Zlock et al. |
| 5,728,109 A | 3/1998 | Schulze et al. |
| 5,728,136 A | 3/1998 | Thal |
| 5,733,293 A | 3/1998 | Scirica et al. |
| 5,733,306 A | 3/1998 | Bonutti |
| 5,733,307 A | 3/1998 | Dinsdale |
| 5,735,875 A | 4/1998 | Bonutti et al. |
| 5,741,259 A | 4/1998 | Chan |
| 5,741,260 A | 4/1998 | Songer et al. |
| 5,741,281 A | 4/1998 | Martin et al. |
| 5,743,912 A | 4/1998 | Lahille et al. |
| 5,746,751 A | 5/1998 | Sherts |
| 5,746,752 A | 5/1998 | Burkhart |
| 5,746,754 A | 5/1998 | Chan |
| 5,749,898 A | 5/1998 | Schulze et al. |
| 5,755,729 A | 5/1998 | de la Torre et al. |
| 5,755,791 A | 5/1998 | Whitson et al. |
| 5,766,176 A | 6/1998 | Duncan |
| 5,766,218 A | 6/1998 | Arnott |
| 5,766,250 A | 6/1998 | Chervitz et al. |
| 5,769,894 A | 6/1998 | Ferragamo |

(56) References Cited

U.S. PATENT DOCUMENTS

| | | |
|---|---|---|
| 5,769,899 A | 6/1998 | Schwartz et al. |
| 5,772,673 A | 6/1998 | Cuny et al. |
| 5,776,196 A | 7/1998 | Matsuzaki et al. |
| 5,776,200 A | 7/1998 | Johnson et al. |
| 5,782,845 A | 7/1998 | Shewchuk |
| 5,782,862 A | 7/1998 | Bonutti |
| 5,782,864 A | 7/1998 | Lizardi |
| 5,782,866 A | 7/1998 | Wenstrom, Jr. |
| 5,782,925 A | 7/1998 | Collazo et al. |
| 5,785,714 A | 7/1998 | Morgan et al. |
| 5,786,217 A | 7/1998 | Tubo et al. |
| 5,792,142 A | 8/1998 | Galitzer |
| 5,792,149 A | 8/1998 | Sherts et al. |
| 5,796,127 A | 8/1998 | Hayafuji et al. |
| 5,797,913 A | 8/1998 | Dambreville et al. |
| 5,797,915 A | 8/1998 | Pierson, III et al. |
| 5,797,916 A | 8/1998 | McDowell |
| 5,797,928 A | 8/1998 | Kogasaka |
| 5,800,407 A | 9/1998 | Eldor et al. |
| 5,810,824 A | 9/1998 | Chan |
| 5,810,848 A | 9/1998 | Hayhurst |
| 5,811,094 A | 9/1998 | Caplan et al. |
| 5,814,056 A | 9/1998 | Prosst et al. |
| 5,814,069 A | 9/1998 | Schulze et al. |
| 5,814,070 A | 9/1998 | Borzone et al. |
| 5,814,072 A * | 9/1998 | Bonutti .................. 606/232 |
| 5,814,073 A | 9/1998 | Bonutti |
| 5,817,095 A | 10/1998 | Smith |
| 5,823,980 A | 10/1998 | Kopfer |
| 5,824,011 A | 10/1998 | Stone et al. |
| 5,824,066 A | 10/1998 | Gross |
| 5,830,234 A | 11/1998 | Wojciechowicz et al. |
| 5,836,955 A | 11/1998 | Buelna et al. |
| 5,843,084 A | 12/1998 | Hart et al. |
| 5,845,645 A * | 12/1998 | Bonutti .................. 128/898 |
| 5,846,254 A | 12/1998 | Schulze et al. |
| 5,848,983 A | 12/1998 | Basaj et al. |
| 5,849,012 A | 12/1998 | Abboudi |
| 5,860,947 A | 1/1999 | Stamler |
| 5,860,973 A | 1/1999 | Michelson |
| 5,860,978 A | 1/1999 | McDevitt et al. |
| 5,868,740 A | 2/1999 | LeVeen et al. |
| 5,868,748 A | 2/1999 | Burke |
| 5,868,789 A | 2/1999 | Huebner |
| 5,871,456 A | 2/1999 | Armstrong et al. |
| 5,871,484 A | 2/1999 | Spievack et al. |
| 5,871,486 A | 2/1999 | Huebner et al. |
| 5,871,490 A | 2/1999 | Schulze et al. |
| 5,885,294 A | 3/1999 | Pedlick et al. |
| 5,891,168 A | 4/1999 | Thal |
| 5,893,592 A | 4/1999 | Schulze et al. |
| 5,895,395 A | 4/1999 | Yeung |
| 5,897,564 A | 4/1999 | Schulze et al. |
| 5,897,574 A | 4/1999 | Bonutti |
| 5,899,902 A | 5/1999 | Brown et al. |
| 5,899,938 A | 5/1999 | Sklar et al. |
| 5,906,934 A | 5/1999 | Grande et al. |
| 5,908,421 A | 6/1999 | Beger et al. |
| 5,908,436 A | 6/1999 | Cuschieri et al. |
| 5,910,148 A | 6/1999 | Reimels et al. |
| 5,911,721 A | 6/1999 | Nicholson et al. |
| 5,916,557 A | 6/1999 | Berlowitz-tarrant et al. |
| 5,918,604 A | 7/1999 | Whelan |
| 5,921,986 A | 7/1999 | Bonutti |
| 5,925,008 A | 7/1999 | Douglas |
| 5,928,231 A | 7/1999 | Klein et al. |
| 5,928,267 A | 7/1999 | Bonutti et al. |
| 5,928,286 A | 7/1999 | Ashby et al. |
| RE36,289 E | 8/1999 | Le et al. |
| 5,931,838 A | 8/1999 | Vito |
| 5,931,844 A | 8/1999 | Thompson et al. |
| 5,931,869 A | 8/1999 | Boucher et al. |
| 5,935,119 A | 8/1999 | Guy et al. |
| 5,935,133 A | 8/1999 | Wagner et al. |
| 5,935,134 A | 8/1999 | Pedlick et al. |
| 5,935,149 A | 8/1999 | Ek |
| 5,938,668 A | 8/1999 | Scirica et al. |
| 5,941,439 A | 8/1999 | Kammerer et al. |
| 5,941,900 A | 8/1999 | Bonutti |
| 5,944,739 A | 8/1999 | Zlock et al. |
| 5,946,783 A | 9/1999 | Plociennik et al. |
| 5,947,915 A | 9/1999 | Thibodo, Jr. |
| 5,947,982 A | 9/1999 | Duran |
| 5,947,999 A | 9/1999 | Groiso |
| 5,948,002 A | 9/1999 | Bonutti |
| 5,951,559 A | 9/1999 | Burkhart |
| 5,951,560 A | 9/1999 | Simon et al. |
| 5,954,747 A * | 9/1999 | Clark .................. 606/216 |
| 5,957,953 A | 9/1999 | DiPoto et al. |
| 5,961,520 A | 10/1999 | Beck, Jr. et al. |
| 5,961,521 A | 10/1999 | Roger et al. |
| 5,961,524 A | 10/1999 | Crombie |
| 5,963,869 A | 10/1999 | Fehnel |
| 5,964,764 A | 10/1999 | West, Jr. et al. |
| 5,964,767 A | 10/1999 | Tapia et al. |
| 5,964,769 A | 10/1999 | Wagner et al. |
| 5,964,783 A | 10/1999 | Grafton et al. |
| 5,968,045 A | 10/1999 | Frazier |
| 5,968,047 A | 10/1999 | Reed |
| 5,968,077 A | 10/1999 | Wojciechowicz et al. |
| 5,970,697 A | 10/1999 | Jacobs et al. |
| 5,972,006 A | 10/1999 | Sciaino, Jr. |
| 5,976,125 A | 11/1999 | Graham |
| 5,976,127 A | 11/1999 | Lax |
| 5,980,473 A | 11/1999 | Korakianitis et al. |
| 5,980,524 A | 11/1999 | Justin et al. |
| 5,980,539 A | 11/1999 | Kontos |
| 5,980,548 A | 11/1999 | Evans et al. |
| 5,980,558 A | 11/1999 | Wiley |
| 5,980,559 A | 11/1999 | Bonutti |
| 5,989,252 A | 11/1999 | Fumex |
| 5,989,256 A | 11/1999 | Kuslich et al. |
| 5,989,282 A | 11/1999 | Bonutti |
| 5,989,294 A | 11/1999 | Marlow |
| 5,993,452 A | 11/1999 | Vandewalle |
| 5,993,476 A | 11/1999 | Groiso |
| 5,997,542 A | 12/1999 | Burke |
| 5,997,552 A | 12/1999 | Person et al. |
| 5,997,575 A | 12/1999 | Whitson et al. |
| 6,001,100 A | 12/1999 | Sherman et al. |
| 6,001,106 A | 12/1999 | Ryan et al. |
| 6,004,351 A | 12/1999 | Tomita et al. |
| 6,004,352 A | 12/1999 | Buni |
| 6,007,538 A | 12/1999 | Levin |
| 6,007,567 A | 12/1999 | Bonutti |
| 6,010,525 A | 1/2000 | Bonutti et al. |
| 6,013,103 A | 1/2000 | Kaufman et al. |
| 6,016,727 A | 1/2000 | Morgan |
| 6,019,767 A | 2/2000 | Howell |
| 6,022,352 A | 2/2000 | Vandewalle |
| 6,022,373 A | 2/2000 | Li |
| 6,024,758 A | 2/2000 | Thal |
| 6,027,523 A | 2/2000 | Schmieding |
| 6,030,410 A | 2/2000 | Zurbrugg |
| 6,033,429 A | 3/2000 | Magovern |
| 6,033,430 A | 3/2000 | Bonutti |
| 6,036,695 A | 3/2000 | Smith |
| 6,039,753 A | 3/2000 | Meislin |
| 6,041,485 A | 3/2000 | Pedlick et al. |
| 6,042,601 A | 3/2000 | Smith |
| 6,042,609 A | 3/2000 | Giordano et al. |
| 6,045,551 A | 4/2000 | Bonutti |
| 6,045,571 A | 4/2000 | Hill et al. |
| 6,045,572 A | 4/2000 | Johnson et al. |
| 6,045,573 A | 4/2000 | Wenstrom, Jr. et al. |
| 6,045,574 A | 4/2000 | Thal |
| 6,047,826 A | 4/2000 | Kalinski et al. |
| 6,048,343 A | 4/2000 | Mathis et al. |
| 6,051,006 A | 4/2000 | Shluzas et al. |
| 6,051,007 A | 4/2000 | Hogendijk et al. |
| 6,053,916 A | 4/2000 | Moore |
| 6,053,921 A | 4/2000 | Wagner et al. |
| 6,056,752 A | 5/2000 | Roger |
| 6,056,772 A | 5/2000 | Bonutti |

(56) References Cited

U.S. PATENT DOCUMENTS

| | | |
|---|---|---|
| 6,056,773 A | 5/2000 | Bonutti |
| 6,059,817 A | 5/2000 | Bonutti et al. |
| 6,059,818 A | 5/2000 | Johnson et al. |
| 6,062,344 A | 5/2000 | Okabe et al. |
| 6,066,173 A | 5/2000 | McKernan et al. |
| 6,068,648 A | 5/2000 | Cole et al. |
| 6,071,305 A | 6/2000 | Brown et al. |
| 6,074,403 A | 6/2000 | Nord |
| 6,077,277 A | 6/2000 | Mollenauer et al. |
| 6,077,292 A | 6/2000 | Bonutti |
| 6,080,185 A | 6/2000 | Johnson et al. |
| 6,086,591 A | 7/2000 | Bojarski |
| 6,086,592 A | 7/2000 | Rosenberg et al. |
| 6,086,608 A | 7/2000 | Ek et al. |
| 6,093,200 A | 7/2000 | Liu et al. |
| 6,096,060 A | 8/2000 | Fitts et al. |
| 6,099,527 A | 8/2000 | Hochschuler et al. |
| 6,099,530 A | 8/2000 | Simonian et al. |
| 6,099,568 A | 8/2000 | Simonian et al. |
| 6,102,934 A | 8/2000 | Li |
| 6,106,545 A | 8/2000 | Egan |
| 6,110,128 A | 8/2000 | Andelin et al. |
| 6,110,207 A | 8/2000 | Eichhorn et al. |
| 6,113,604 A | 9/2000 | Whittaker et al. |
| 6,117,160 A | 9/2000 | Bonutti |
| 6,117,162 A | 9/2000 | Schmieding et al. |
| 6,123,710 A | 9/2000 | Pinczewski et al. |
| 6,127,596 A | 10/2000 | Brown et al. |
| 6,132,433 A | 10/2000 | Whelan |
| 6,132,437 A | 10/2000 | Omurtag et al. |
| 6,136,010 A | 10/2000 | Modesitt et al. |
| 6,139,565 A | 10/2000 | Stone et al. |
| RE36,974 E | 11/2000 | Bonutti |
| 6,143,017 A | 11/2000 | Thal |
| 6,146,406 A | 11/2000 | Shluzas et al. |
| 6,146,408 A | 11/2000 | Bartlett |
| 6,149,653 A | 11/2000 | Deslauriers |
| 6,149,669 A | 11/2000 | Li |
| 6,150,163 A | 11/2000 | McPherson et al. |
| 6,152,928 A | 11/2000 | Wenstrom, Jr. |
| 6,152,934 A | 11/2000 | Harper et al. |
| 6,152,936 A | 11/2000 | Christy et al. |
| 6,152,949 A | 11/2000 | Bonutti |
| 6,156,039 A | 12/2000 | Thal |
| 6,156,056 A | 12/2000 | Kearns et al. |
| 6,159,234 A | 12/2000 | Bonutti et al. |
| 6,165,203 A | 12/2000 | Krebs |
| 6,168,598 B1 | 1/2001 | Martello |
| 6,168,628 B1 | 1/2001 | Huebner |
| 6,171,310 B1 | 1/2001 | Giordano et al. |
| 6,179,840 B1 | 1/2001 | Bowman |
| 6,183,461 B1 | 2/2001 | Matsuura et al. |
| 6,183,737 B1 | 2/2001 | Zaleske et al. |
| 6,187,025 B1 | 2/2001 | Machek |
| 6,190,348 B1 | 2/2001 | Tiemann |
| 6,190,401 B1 | 2/2001 | Green et al. |
| 6,190,411 B1 | 2/2001 | Lo et al. |
| 6,193,754 B1 | 2/2001 | Seedhom |
| 6,200,318 B1 | 3/2001 | Har-Shai et al. |
| 6,200,329 B1 | 3/2001 | Fung et al. |
| 6,200,330 B1 | 3/2001 | Benderev et al. |
| 6,200,606 B1 | 3/2001 | Peterson et al. |
| 6,200,685 B1 | 3/2001 | Davidson |
| 6,203,556 B1 | 3/2001 | Evans et al. |
| 6,203,563 B1 | 3/2001 | Fernandez |
| 6,203,565 B1 | 3/2001 | Bonutti et al. |
| 6,203,572 B1 | 3/2001 | Johnson et al. |
| 6,203,576 B1 | 3/2001 | Afriat et al. |
| 6,206,883 B1 | 3/2001 | Tunc |
| 6,210,376 B1 | 4/2001 | Grayson |
| 6,210,381 B1 | 4/2001 | Morse |
| 6,214,007 B1 | 4/2001 | Anderson |
| 6,214,012 B1 | 4/2001 | Karpman et al. |
| 6,217,580 B1 | 4/2001 | Levin |
| 6,221,107 B1 | 4/2001 | Steiner et al. |
| 6,228,096 B1 | 5/2001 | Marchand |
| 6,231,592 B1 | 5/2001 | Bonutti et al. |
| 6,234,980 B1 | 5/2001 | Bell |
| 6,235,057 B1 | 5/2001 | Roger et al. |
| 6,235,058 B1 | 5/2001 | Huene |
| 6,238,395 B1 | 5/2001 | Bonutti |
| 6,241,734 B1 | 6/2001 | Scribner et al. |
| 6,241,747 B1 | 6/2001 | Ruff |
| 6,241,771 B1 | 6/2001 | Gresser et al. |
| 6,245,081 B1 | 6/2001 | Bowman et al. |
| 6,254,604 B1 | 7/2001 | Howell |
| 6,258,091 B1 | 7/2001 | Sevrain et al. |
| 6,267,766 B1 | 7/2001 | Burkhart |
| 6,269,716 B1 | 8/2001 | Amis |
| 6,270,518 B1 | 8/2001 | Pedlick et al. |
| 6,273,890 B1 | 8/2001 | Frazier |
| 6,280,474 B1 | 8/2001 | Cassidy et al. |
| 6,283,973 B1 | 9/2001 | Hubbard et al. |
| 6,283,996 B1 | 9/2001 | Chervitz et al. |
| 6,287,307 B1 | 9/2001 | Abboudi |
| 6,287,325 B1 | 9/2001 | Bonutti |
| 6,293,929 B1 | 9/2001 | Smith et al. |
| 6,293,961 B2 | 9/2001 | Schwartz et al. |
| 6,296,659 B1 * | 10/2001 | Foerster .................. 606/224 |
| 6,299,615 B1 | 10/2001 | Huebner |
| 6,302,888 B1 | 10/2001 | Mellinger et al. |
| 6,302,899 B1 | 10/2001 | Johnson et al. |
| 6,302,915 B1 | 10/2001 | Cooney, III et al. |
| 6,303,158 B1 | 10/2001 | Odgaard et al. |
| 6,306,156 B1 | 10/2001 | Clark |
| 6,306,158 B1 | 10/2001 | Bartlett |
| 6,306,159 B1 | 10/2001 | Schwartz et al. |
| 6,309,124 B1 | 10/2001 | Gueret |
| 6,309,405 B1 | 10/2001 | Bonutti |
| 6,312,448 B1 | 11/2001 | Bonutti |
| 6,315,788 B1 | 11/2001 | Roby |
| 6,319,224 B1 | 11/2001 | Stout et al. |
| 6,319,271 B1 | 11/2001 | Schwartz et al. |
| 6,328,758 B1 | 12/2001 | Tornier et al. |
| 6,334,064 B1 | 12/2001 | Fiddian-green |
| 6,342,060 B1 | 1/2002 | Adams |
| 6,343,531 B2 | 2/2002 | Amis |
| 6,355,066 B1 | 3/2002 | Kim |
| 6,358,270 B1 | 3/2002 | Lemer |
| 6,364,897 B1 | 4/2002 | Bonutti |
| 6,368,322 B1 | 4/2002 | Luks et al. |
| 6,368,326 B1 | 4/2002 | Dakin et al. |
| 6,368,343 B1 | 4/2002 | Bonutti et al. |
| 6,371,124 B1 | 4/2002 | Whelan |
| 6,379,361 B1 | 4/2002 | Beck, Jr. et al. |
| 6,383,190 B1 | 5/2002 | Preissman |
| 6,383,199 B2 | 5/2002 | Carter et al. |
| 6,387,113 B1 | 5/2002 | Hawkins et al. |
| 6,387,129 B2 | 5/2002 | Rieser et al. |
| 6,391,030 B1 | 5/2002 | Wagner et al. |
| 6,398,785 B2 | 6/2002 | Carchidi et al. |
| 6,406,456 B1 | 6/2002 | Slate et al. |
| 6,406,479 B1 | 6/2002 | Justin et al. |
| 6,409,743 B1 | 6/2002 | Fenton, Jr. |
| 6,413,260 B1 | 7/2002 | Berrevoets et al. |
| 6,423,073 B2 | 7/2002 | Bowman |
| 6,423,088 B1 | 7/2002 | Fenton, Jr. |
| 6,425,924 B1 | 7/2002 | Rousseau |
| 6,428,562 B2 | 8/2002 | Bonutti |
| 6,432,123 B2 | 8/2002 | Schwartz et al. |
| 6,436,123 B1 | 8/2002 | Magovern |
| 6,436,124 B1 | 8/2002 | Anderson et al. |
| 6,440,134 B1 | 8/2002 | Zaccherotti et al. |
| 6,440,136 B1 | 8/2002 | Gambale et al. |
| 6,447,516 B1 | 9/2002 | Bonutti |
| 6,451,030 B2 * | 9/2002 | Li et al. .................. 606/139 |
| 6,454,768 B1 | 9/2002 | Jackson |
| 6,458,134 B1 | 10/2002 | Songer et al. |
| 6,458,161 B1 | 10/2002 | Gibbs et al. |
| 6,461,373 B2 | 10/2002 | Wyman et al. |
| 6,464,690 B1 | 10/2002 | Castaneda et al. |
| 6,464,713 B2 | 10/2002 | Bonutti |
| 6,468,293 B2 | 10/2002 | Bonutti et al. |
| 6,471,707 B1 | 10/2002 | Miller et al. |

(56) References Cited

U.S. PATENT DOCUMENTS

| | | | |
|---|---|---|---|
| 6,475,230 B1 * | 11/2002 | Bonutti et al. | 606/232 |
| 6,478,753 B2 | 11/2002 | Reay-Young | |
| 6,482,210 B1 | 11/2002 | Skiba et al. | |
| 6,485,504 B1 * | 11/2002 | Johnson et al. | 606/216 |
| 6,491,714 B1 | 12/2002 | Bennett | |
| 6,497,901 B1 | 12/2002 | Royer | |
| 6,500,184 B1 | 12/2002 | Chan et al. | |
| 6,500,195 B2 | 12/2002 | Bonutti | |
| RE37,963 E | 1/2003 | Thal | |
| 6,503,267 B2 | 1/2003 | Bonutti et al. | |
| 6,506,190 B1 | 1/2003 | Walshe | |
| 6,508,820 B2 | 1/2003 | Bales | |
| 6,508,821 B1 | 1/2003 | Schwartz et al. | |
| 6,508,830 B2 | 1/2003 | Steiner | |
| 6,511,498 B1 | 1/2003 | Fumex | |
| 6,511,499 B2 | 1/2003 | Schmieding et al. | |
| 6,514,274 B1 | 2/2003 | Boucher et al. | |
| 6,517,542 B1 | 2/2003 | Papay et al. | |
| 6,517,552 B1 | 2/2003 | Nord et al. | |
| 6,517,564 B1 | 2/2003 | Grafton et al. | |
| 6,517,578 B2 | 2/2003 | Hein | |
| 6,517,579 B1 | 2/2003 | Paulos et al. | |
| 6,520,964 B2 | 2/2003 | Tallarida et al. | |
| 6,520,980 B1 | 2/2003 | Foerster | |
| 6,524,317 B1 | 2/2003 | Ritchart et al. | |
| 6,527,777 B2 | 3/2003 | Justin | |
| 6,527,794 B1 | 3/2003 | McDevitt et al. | |
| 6,527,795 B1 | 3/2003 | Lizardi | |
| 6,533,795 B1 | 3/2003 | Tran et al. | |
| 6,533,802 B2 | 3/2003 | Bojarski et al. | |
| 6,537,319 B2 | 3/2003 | Whelan | |
| 6,540,750 B2 | 4/2003 | Burkhart | |
| 6,540,769 B1 | 4/2003 | Miller, III | |
| 6,540,770 B1 | 4/2003 | Tornier et al. | |
| 6,540,783 B1 | 4/2003 | Whittaker et al. | |
| 6,543,094 B2 | 4/2003 | D'Addario | |
| 6,544,281 B2 | 4/2003 | ElAttrache et al. | |
| 6,547,564 B1 | 4/2003 | Hansson et al. | |
| 6,547,778 B1 | 4/2003 | Sklar et al. | |
| 6,547,800 B2 | 4/2003 | Foerster et al. | |
| 6,551,330 B1 | 4/2003 | Bain et al. | |
| 6,551,343 B1 | 4/2003 | Tormala et al. | |
| 6,551,353 B1 | 4/2003 | Baker et al. | |
| 6,553,802 B1 | 4/2003 | Jacob et al. | |
| 6,554,830 B1 | 4/2003 | Chappius | |
| 6,554,852 B1 | 4/2003 | Oberlander | |
| 6,554,862 B2 | 4/2003 | Hays et al. | |
| 6,558,389 B2 | 5/2003 | Clark et al. | |
| 6,562,071 B2 | 5/2003 | Jarvinen et al. | |
| 6,565,572 B2 | 5/2003 | Chappius | |
| 6,565,573 B1 | 5/2003 | Ferrante et al. | |
| 6,569,186 B1 | 5/2003 | Winters et al. | |
| 6,569,187 B1 | 5/2003 | Bonutti et al. | |
| 6,572,635 B1 | 6/2003 | Bonutti | |
| 6,572,655 B1 | 6/2003 | Johnson | |
| 6,575,925 B1 | 6/2003 | Noble | |
| 6,579,295 B1 | 6/2003 | Supinski | |
| 6,582,453 B1 | 6/2003 | Tran et al. | |
| 6,585,730 B1 | 7/2003 | Foerster | |
| 6,585,740 B2 | 7/2003 | Schlapfer et al. | |
| 6,585,750 B2 | 7/2003 | Bonutti et al. | |
| 6,589,245 B1 | 7/2003 | Weiler et al. | |
| 6,589,246 B1 | 7/2003 | Hack et al. | |
| 6,592,609 B1 * | 7/2003 | Bonutti | 606/232 |
| 6,592,622 B1 | 7/2003 | Ferguson | |
| 6,595,911 B2 | 7/2003 | LoVuolo | |
| 6,599,289 B1 | 7/2003 | Bojarski et al. | |
| 6,599,319 B2 | 7/2003 | Knudsen et al. | |
| 6,605,096 B1 | 8/2003 | Ritchart | |
| 6,607,548 B2 | 8/2003 | Pohjonen et al. | |
| 6,610,079 B1 | 8/2003 | Li et al. | |
| 6,613,018 B2 | 9/2003 | Bagga et al. | |
| 6,616,694 B1 | 9/2003 | Hart | |
| 6,620,166 B1 | 9/2003 | Wenstrom, Jr. et al. | |
| 6,620,185 B1 | 9/2003 | Harvie et al. | |
| 6,620,195 B2 | 9/2003 | Goble et al. | |
| 6,620,329 B2 | 9/2003 | Rosen et al. | |
| 6,620,349 B1 | 9/2003 | Lopez | |
| 6,623,492 B1 | 9/2003 | Berube et al. | |
| 6,623,524 B2 | 9/2003 | Schmieding | |
| 6,626,910 B1 | 9/2003 | Hugues | |
| 6,626,919 B1 | 9/2003 | Swanstrom | |
| 6,626,930 B1 | 9/2003 | Allen et al. | |
| 6,629,977 B1 | 10/2003 | Wolf | |
| 6,629,997 B2 | 10/2003 | Mansmann | |
| 6,632,245 B2 | 10/2003 | Kim | |
| 6,635,073 B2 | 10/2003 | Bonutti | |
| 6,638,279 B2 | 10/2003 | Bonutti | |
| 6,638,286 B1 | 10/2003 | Burbank et al. | |
| 6,638,312 B2 | 10/2003 | Plouhar et al. | |
| 6,641,596 B1 | 11/2003 | Lizardi | |
| 6,641,597 B2 | 11/2003 | Burkhart et al. | |
| 6,645,169 B1 | 11/2003 | Slate et al. | |
| 6,645,211 B2 | 11/2003 | Magana | |
| 6,645,227 B2 | 11/2003 | Fallin et al. | |
| 6,648,921 B2 | 11/2003 | Anderson et al. | |
| 6,652,450 B2 | 11/2003 | Neisz et al. | |
| 6,652,533 B2 | 11/2003 | O'neil | |
| 6,652,560 B1 | 11/2003 | Gerke et al. | |
| 6,652,562 B2 | 11/2003 | Collier et al. | |
| 6,652,563 B2 | 11/2003 | Dreyfuss | |
| 6,656,182 B1 | 12/2003 | Hayhurst | |
| 6,656,183 B2 | 12/2003 | Colleran et al. | |
| 6,658,182 B1 | 12/2003 | Gonthier | |
| 6,660,008 B1 | 12/2003 | Foerster et al. | |
| 6,660,022 B1 | 12/2003 | Li et al. | |
| 6,663,634 B2 | 12/2003 | Ahrens et al. | |
| 6,663,656 B2 | 12/2003 | Schmieding et al. | |
| 6,666,868 B2 | 12/2003 | Fallin | |
| 6,666,877 B2 | 12/2003 | Morgan et al. | |
| 6,669,707 B1 | 12/2003 | Swanstrom et al. | |
| 6,679,889 B1 | 1/2004 | West, Jr. et al. | |
| 6,682,533 B1 | 1/2004 | Dinsdale et al. | |
| 6,682,549 B2 | 1/2004 | Bartlett | |
| 6,685,728 B2 | 2/2004 | Sinnott et al. | |
| 6,689,137 B2 | 2/2004 | Reed | |
| 6,689,153 B1 | 2/2004 | Skiba | |
| 6,689,154 B2 | 2/2004 | Bartlett | |
| 6,692,499 B2 | 2/2004 | Tormala et al. | |
| 6,692,516 B2 | 2/2004 | West, Jr. et al. | |
| 6,695,852 B2 | 2/2004 | Gleason | |
| 6,712,849 B2 | 3/2004 | Re et al. | |
| 6,712,859 B2 | 3/2004 | Rousseau et al. | |
| 6,716,190 B1 | 4/2004 | Glines et al. | |
| 6,716,224 B2 | 4/2004 | Singhatat | |
| 6,716,957 B2 | 4/2004 | Tunc | |
| 6,730,092 B2 | 5/2004 | Songer | |
| 6,730,124 B2 | 5/2004 | Steiner | |
| 6,736,799 B1 | 5/2004 | Erbe et al. | |
| 6,737,053 B1 | 5/2004 | Goh et al. | |
| 6,746,483 B1 | 6/2004 | Bojarski et al. | |
| 6,752,780 B2 | 6/2004 | Stout et al. | |
| 6,752,810 B2 | 6/2004 | Gao et al. | |
| 6,752,831 B2 | 6/2004 | Sybert et al. | |
| 6,755,836 B1 | 6/2004 | Lewis | |
| 6,755,868 B2 | 6/2004 | Rousseau | |
| 6,761,722 B2 | 7/2004 | Cole et al. | |
| 6,761,739 B2 | 7/2004 | Shepard | |
| 6,767,037 B2 | 7/2004 | Wenstrom, Jr. | |
| 6,770,076 B2 | 8/2004 | Foerster | |
| 6,770,084 B1 | 8/2004 | Bain et al. | |
| 6,773,450 B2 | 8/2004 | Leung et al. | |
| 6,779,701 B2 | 8/2004 | Bailly et al. | |
| 6,780,190 B2 | 8/2004 | Maroney | |
| 6,780,198 B1 | 8/2004 | Gregoire et al. | |
| 6,790,210 B1 | 9/2004 | Cragg et al. | |
| 6,793,595 B1 | 9/2004 | Monnet | |
| 6,802,862 B1 | 10/2004 | Roger et al. | |
| 6,808,502 B2 | 10/2004 | Nguyen et al. | |
| 6,808,526 B1 | 10/2004 | Magerl et al. | |
| 6,814,741 B2 | 11/2004 | Bowman et al. | |
| 6,830,572 B2 | 12/2004 | McDevitt et al. | |
| 6,833,005 B1 | 12/2004 | Mantas et al. | |
| 6,835,377 B2 | 12/2004 | Goldberg et al. | |

(56) References Cited

U.S. PATENT DOCUMENTS

| | | |
|---|---|---|
| 6,840,953 B2 | 1/2005 | Martinek |
| 6,860,885 B2 | 3/2005 | Bonutti |
| 6,860,895 B1 | 3/2005 | Akerfeldt et al. |
| 6,863,671 B1 | 3/2005 | Strobel et al. |
| 6,872,040 B2 | 3/2005 | Deeg et al. |
| 6,872,210 B2 | 3/2005 | Hearn |
| 6,875,216 B2 | 4/2005 | Wolf |
| 6,884,249 B2 | 4/2005 | May et al. |
| 6,887,259 B2 | 5/2005 | Lizardi |
| 6,887,271 B2 | 5/2005 | Justin et al. |
| 6,890,354 B2 | 5/2005 | Steiner et al. |
| 6,893,448 B2 | 5/2005 | O'Quinn et al. |
| 6,896,686 B2 | 5/2005 | Weber |
| 6,899,722 B2 | 5/2005 | Bonutti |
| 6,902,573 B2 | 6/2005 | Strobel et al. |
| 6,905,513 B1 | 6/2005 | Metzger |
| 6,908,466 B1 | 6/2005 | Bonutti et al. |
| 6,911,202 B2 | 6/2005 | Amir et al. |
| 6,916,292 B2 | 7/2005 | Morawski et al. |
| 6,916,321 B2 | 7/2005 | TenHuisen et al. |
| 6,921,402 B2 | 7/2005 | Contiliano et al. |
| 6,923,823 B1 | 8/2005 | Bartlett et al. |
| 6,923,824 B2 | 8/2005 | Morgan et al. |
| 6,939,379 B2 | 9/2005 | Sklar |
| 6,949,102 B2 | 9/2005 | Andrews |
| 6,951,565 B2 | 10/2005 | Keane et al. |
| 6,960,214 B2 | 11/2005 | Burkinshaw |
| 6,966,887 B1 | 11/2005 | Chin |
| 6,966,916 B2 | 11/2005 | Kumar |
| 6,969,391 B1 | 11/2005 | Gazzani |
| 6,969,398 B2 | 11/2005 | Stevens et al. |
| 6,972,027 B2 | 12/2005 | Fallin et al. |
| 6,980,903 B2 | 12/2005 | Daniels et al. |
| 6,984,237 B2 | 1/2006 | Hatch et al. |
| 6,986,781 B2 | 1/2006 | Smith |
| 6,989,034 B2 | 1/2006 | Hammer et al. |
| 6,994,719 B2 | 2/2006 | Grafton |
| 6,994,725 B1 | 2/2006 | Goble |
| 7,001,429 B2 | 2/2006 | Ferguson |
| 7,004,959 B2 | 2/2006 | Bonutti |
| 7,008,451 B2 | 3/2006 | Justin et al. |
| 7,048,754 B2 | 5/2006 | Martin et al. |
| 7,052,499 B2 | 5/2006 | Steger et al. |
| 7,066,942 B2 | 6/2006 | Treace |
| 7,066,944 B2 | 6/2006 | Laufer et al. |
| 7,081,126 B2 | 7/2006 | McDevitt et al. |
| 7,083,638 B2 | 8/2006 | Foerster |
| 7,087,064 B1 | 8/2006 | Hyde |
| 7,097,654 B1 | 8/2006 | Freedland |
| 7,105,010 B2 | 9/2006 | Hart et al. |
| 7,112,221 B2 | 9/2006 | Harris et al. |
| 7,118,578 B2 | 10/2006 | West, Jr. et al. |
| 7,118,583 B2 | 10/2006 | O'Quinn et al. |
| 7,125,421 B2 | 10/2006 | Tremulis et al. |
| 7,131,467 B2 | 11/2006 | Gao et al. |
| 7,137,996 B2 | 11/2006 | Steiner et al. |
| 7,141,066 B2 | 11/2006 | Steiner et al. |
| 7,144,414 B2 | 12/2006 | Harvie et al. |
| 7,148,209 B2 | 12/2006 | Hoemann et al. |
| 7,153,127 B2 | 12/2006 | Struble et al. |
| 7,153,307 B2 | 12/2006 | Scribner et al. |
| 7,153,312 B1 | 12/2006 | Torrie et al. |
| 7,153,327 B1 | 12/2006 | Metzger |
| 7,160,285 B2 | 1/2007 | Sklar et al. |
| 7,160,333 B2 | 1/2007 | Plouhar et al. |
| 7,172,626 B1 | 2/2007 | Andrews |
| 7,179,259 B1 | 2/2007 | Gibbs |
| 7,201,722 B2 | 4/2007 | Krueger |
| 7,207,993 B1 | 4/2007 | Baldwin et al. |
| 7,255,675 B2 | 8/2007 | Gertner et al. |
| 7,255,700 B2 | 8/2007 | Kaiser et al. |
| 7,255,715 B2 | 8/2007 | Metzger |
| 7,261,716 B2 | 8/2007 | Strobel et al. |
| 7,264,634 B2 | 9/2007 | Schmieding |
| 7,279,008 B2 | 10/2007 | Brown et al. |
| 7,285,124 B2 | 10/2007 | Foerster |
| 7,291,177 B2 | 11/2007 | Gibbs |
| 7,303,577 B1 | 12/2007 | Dean |
| 7,306,417 B2 | 12/2007 | Dorstewitz |
| 7,309,355 B2 | 12/2007 | Donnelly et al. |
| 7,326,222 B2 | 2/2008 | Dreyfuss et al. |
| 7,329,272 B2 | 2/2008 | Burkhart et al. |
| 7,361,179 B2 | 4/2008 | Rousseau et al. |
| 7,377,845 B2 | 5/2008 | Stewart et al. |
| 7,390,329 B2 | 6/2008 | Westra et al. |
| 7,390,332 B2 | 6/2008 | Selvitelli et al. |
| 7,399,018 B1 | 7/2008 | Khachaturian |
| 7,442,210 B2 | 10/2008 | Segal et al. |
| 7,465,308 B2 | 12/2008 | Sikora et al. |
| 7,468,074 B2 | 12/2008 | Caborn et al. |
| 7,481,814 B1 | 1/2009 | Metzger |
| 7,485,149 B1 | 2/2009 | White |
| 7,494,506 B2 | 2/2009 | Brulez et al. |
| D587,807 S | 3/2009 | Wolf et al. |
| 7,500,983 B1 | 3/2009 | Kaiser et al. |
| 7,513,910 B2 | 4/2009 | Buskirk et al. |
| 7,572,275 B2 | 8/2009 | Fallin et al. |
| 7,572,298 B2 | 8/2009 | Roller et al. |
| 7,578,825 B2 | 8/2009 | Huebner |
| 7,585,311 B2 | 9/2009 | Green et al. |
| 7,591,823 B2 | 9/2009 | Tipirneni |
| 7,597,705 B2 | 10/2009 | Forsberg et al. |
| 7,601,165 B2 | 10/2009 | Stone |
| 7,604,636 B1 | 10/2009 | Walters et al. |
| 7,608,092 B1 | 10/2009 | Schaffhausen |
| 7,608,098 B1 | 10/2009 | Stone et al. |
| 7,615,076 B2 | 11/2009 | Cauthen, III et al. |
| 7,621,937 B2 | 11/2009 | Pipenhagen et al. |
| 7,632,287 B2 | 12/2009 | Baker et al. |
| 7,651,509 B2 | 1/2010 | Bojarski et al. |
| 7,658,750 B2 | 2/2010 | Li |
| 7,658,751 B2 | 2/2010 | Stone et al. |
| 7,670,279 B2 | 3/2010 | Gertner |
| 7,678,123 B2 | 3/2010 | Chanduszko |
| 7,691,112 B2 | 4/2010 | Chanduszko et al. |
| 7,695,493 B2 | 4/2010 | Saadat et al. |
| 7,695,503 B1 | 4/2010 | Kaiser et al. |
| 7,703,372 B1 | 4/2010 | Shakespeare |
| 7,717,929 B2 | 5/2010 | Fallman |
| 7,731,732 B2 | 6/2010 | Ken |
| 7,736,364 B2 | 6/2010 | Stone |
| 7,736,379 B2 | 6/2010 | Ewers et al. |
| 7,749,250 B2 | 7/2010 | Stone et al. |
| 7,758,594 B2 | 7/2010 | Lamson et al. |
| 7,758,611 B2 | 7/2010 | Kato |
| 7,762,942 B2 | 7/2010 | Neisz et al. |
| 7,771,482 B1 | 8/2010 | Karmon |
| 7,776,041 B1 | 8/2010 | Walters |
| 7,790,945 B1 | 9/2010 | Watson, Jr. |
| 7,803,173 B2 | 9/2010 | Burkhart et al. |
| 7,819,895 B2 | 10/2010 | Ginn et al. |
| 7,828,820 B2 | 11/2010 | Stone et al. |
| 7,828,850 B2 | 11/2010 | Cauthen, III et al. |
| 7,856,698 B2 | 12/2010 | Hays |
| 7,857,830 B2 | 12/2010 | Stone et al. |
| 7,867,252 B2 | 1/2011 | Criscuolo et al. |
| 7,867,264 B2 | 1/2011 | McDevitt et al. |
| 7,875,058 B2 | 1/2011 | Holmes, Jr. |
| 7,878,058 B2 | 2/2011 | Blendinger et al. |
| 7,887,586 B2 | 2/2011 | Linares |
| 7,905,903 B2 | 3/2011 | Stone et al. |
| 7,905,904 B2 | 3/2011 | Stone et al. |
| 7,909,851 B2 | 3/2011 | Stone et al. |
| 7,914,539 B2 | 3/2011 | Stone et al. |
| 7,938,847 B2 | 5/2011 | Fanton et al. |
| 7,959,650 B2 | 6/2011 | Kaiser et al. |
| 7,981,140 B2 | 7/2011 | Burkhart |
| 7,998,203 B2 | 8/2011 | Blum |
| 8,034,090 B2 | 10/2011 | Stone et al. |
| 8,062,334 B2 | 11/2011 | Green et al. |
| 8,075,574 B2 | 12/2011 | May et al. |
| 8,088,108 B2 | 1/2012 | Kraft |
| 8,088,130 B2 | 1/2012 | Kaiser et al. |
| 8,114,127 B2 | 2/2012 | West, Jr. |

(56) References Cited

U.S. PATENT DOCUMENTS

| | | |
|---|---|---|
| 8,114,128 B2 | 2/2012 | Cauldwell et al. |
| 8,118,835 B2 | 2/2012 | Weisel et al. |
| 8,118,836 B2 | 2/2012 | Denham et al. |
| 8,118,868 B2 | 2/2012 | May et al. |
| 8,128,658 B2 | 3/2012 | Kaiser et al. |
| 8,137,354 B2 | 3/2012 | Stone |
| 8,137,382 B2 | 3/2012 | Denham et al. |
| 8,162,997 B2 | 4/2012 | Struhl |
| 8,167,906 B2 | 5/2012 | Cauldwell et al. |
| 8,177,810 B2 | 5/2012 | Ferree |
| 8,202,318 B2 | 6/2012 | Willobee |
| 8,221,454 B2 | 7/2012 | Schaffhausen |
| 8,231,654 B2 | 7/2012 | Kaiser et al. |
| 8,251,998 B2 | 8/2012 | Hoeppner et al. |
| 8,252,022 B2 | 8/2012 | Holman et al. |
| 8,273,106 B2 | 9/2012 | Stone et al. |
| 8,292,921 B2 | 10/2012 | Stone et al. |
| 8,298,262 B2 | 10/2012 | Stone et al. |
| 8,298,284 B2 | 10/2012 | Cassani |
| 8,303,604 B2 | 11/2012 | Stone et al. |
| 8,317,825 B2 | 11/2012 | Stone |
| 8,337,525 B2 | 12/2012 | Stone et al. |
| 8,343,155 B2 | 1/2013 | Fisher et al. |
| 8,343,227 B2 | 1/2013 | Metzger et al. |
| 8,361,054 B2 | 1/2013 | Ducharme et al. |
| 8,361,113 B2 | 1/2013 | Stone et al. |
| 8,409,253 B2 | 4/2013 | Stone et al. |
| 8,486,114 B2 | 7/2013 | Gillard et al. |
| 8,500,818 B2 | 8/2013 | Metzger et al. |
| 8,506,597 B2 | 8/2013 | Kaiser et al. |
| 8,551,140 B2 | 10/2013 | Denham et al. |
| 8,562,645 B2 | 10/2013 | Stone et al. |
| 8,562,647 B2 | 10/2013 | Kaiser et al. |
| 8,574,235 B2 | 11/2013 | Stone |
| 8,579,944 B2 | 11/2013 | Holloway et al. |
| 8,597,327 B2 | 12/2013 | Stone et al. |
| 8,608,777 B2 | 12/2013 | Kaiser et al. |
| 8,632,566 B2 | 1/2014 | Olson |
| 8,632,569 B2 | 1/2014 | Stone et al. |
| 8,652,171 B2 | 2/2014 | Stone et al. |
| 8,652,172 B2 | 2/2014 | Denham et al. |
| 8,672,904 B1 | 3/2014 | Schultz |
| 8,672,968 B2 | 3/2014 | Stone et al. |
| 8,672,969 B2 | 3/2014 | Stone et al. |
| 8,721,650 B2 | 5/2014 | Fanton et al. |
| 8,721,684 B2 | 5/2014 | Denham et al. |
| 8,771,316 B2 | 7/2014 | Denham et al. |
| 8,771,352 B2 | 7/2014 | Conner et al. |
| 8,777,956 B2 | 7/2014 | Hoeppner et al. |
| 8,801,783 B2 | 8/2014 | Stone et al. |
| 8,840,645 B2 | 9/2014 | Denham et al. |
| 8,900,314 B2 | 12/2014 | Metzger et al. |
| 8,926,613 B2 | 1/2015 | Kaiser et al. |
| 8,932,331 B2 | 1/2015 | Kaiser et al. |
| 8,936,621 B2 | 1/2015 | Denham et al. |
| 8,968,364 B2 | 3/2015 | Berelsman et al. |
| 8,998,949 B2 | 4/2015 | Stone et al. |
| 9,005,287 B2 | 4/2015 | Stone |
| 9,017,381 B2 | 4/2015 | Kaiser et al. |
| 9,023,058 B2 | 5/2015 | Jaramillo et al. |
| 9,078,644 B2 | 7/2015 | Stone |
| 9,149,267 B2 | 10/2015 | Norton et al. |
| 9,173,651 B2 | 11/2015 | Stone et al. |
| 9,198,673 B2 | 12/2015 | Stone |
| 9,216,078 B2 | 12/2015 | Conner et al. |
| 9,271,713 B2 | 3/2016 | Denham et al. |
| 2001/0010005 A1 | 7/2001 | Kammerer et al. |
| 2001/0014825 A1 | 8/2001 | Burke et al. |
| 2001/0019649 A1 | 9/2001 | Field et al. |
| 2001/0029387 A1 | 10/2001 | Wolf et al. |
| 2001/0037131 A1 | 11/2001 | Schmieding et al. |
| 2001/0037153 A1 | 11/2001 | Rockwood et al. |
| 2001/0041916 A1 | 11/2001 | Bonutti |
| 2001/0041937 A1 | 11/2001 | Rieser et al. |
| 2001/0041938 A1 | 11/2001 | Hein |
| 2001/0044639 A1 | 11/2001 | Levinson |
| 2001/0047206 A1 | 11/2001 | Sklar et al. |
| 2001/0051815 A1 | 12/2001 | Esplin |
| 2001/0051816 A1 | 12/2001 | Enzerink et al. |
| 2001/0053934 A1 | 12/2001 | Schmieding |
| 2002/0001964 A1 | 1/2002 | Choi |
| 2002/0004669 A1 | 1/2002 | Bartlett |
| 2002/0007182 A1 | 1/2002 | Kim |
| 2002/0010513 A1 | 1/2002 | Schmieding |
| 2002/0013607 A1 | 1/2002 | Lemer |
| 2002/0013608 A1 | 1/2002 | ElAttrache et al. |
| 2002/0019649 A1 | 2/2002 | Sikora et al. |
| 2002/0029066 A1 | 3/2002 | Foerster |
| 2002/0032465 A1 | 3/2002 | Lemer |
| 2002/0055780 A1 | 5/2002 | Sklar |
| 2002/0058966 A1 | 5/2002 | Tormala et al. |
| 2002/0068254 A1 | 6/2002 | Campbell |
| 2002/0077629 A1 | 6/2002 | Hoffman et al. |
| 2002/0077659 A1 | 6/2002 | Johnson et al. |
| 2002/0082220 A1 | 6/2002 | Hoemann et al. |
| 2002/0099411 A1 | 7/2002 | Bartlett |
| 2002/0111591 A1 | 8/2002 | Mckinnon et al. |
| 2002/0111653 A1 | 8/2002 | Foerster |
| 2002/0120270 A1 | 8/2002 | Trieu et al. |
| 2002/0120292 A1 | 8/2002 | Morgan |
| 2002/0123752 A1 | 9/2002 | Schultheiss et al. |
| 2002/0128654 A1 | 9/2002 | Steger et al. |
| 2002/0128684 A1 | 9/2002 | Foerster |
| 2002/0129820 A1 | 9/2002 | Ryan et al. |
| 2002/0143336 A1 | 10/2002 | Hearn |
| 2002/0147463 A1 | 10/2002 | Martinek |
| 2002/0156475 A1 | 10/2002 | Lerch et al. |
| 2002/0161401 A1 | 10/2002 | Steiner |
| 2002/0161439 A1 | 10/2002 | Strobel et al. |
| 2002/0165548 A1 | 11/2002 | Jutley |
| 2002/0165611 A1 | 11/2002 | Enzerink et al. |
| 2002/0169452 A1 | 11/2002 | Tormala et al. |
| 2002/0169477 A1 | 11/2002 | Demopulos et al. |
| 2002/0169478 A1 | 11/2002 | Schwartz et al. |
| 2002/0173788 A1 | 11/2002 | Bojarski et al. |
| 2002/0177853 A1 | 11/2002 | Chervitz et al. |
| 2002/0188298 A1 | 12/2002 | Chan |
| 2002/0193830 A1 | 12/2002 | Bonutti |
| 2003/0004545 A1 | 1/2003 | Burkhart et al. |
| 2003/0009235 A1 | 1/2003 | Manrique et al. |
| 2003/0023268 A1 | 1/2003 | Lizardi |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0065391 A1 | 4/2003 | Re et al. |
| 2003/0065402 A1 | 4/2003 | Anderson et al. |
| 2003/0078585 A1 | 4/2003 | Johnson et al. |
| 2003/0078603 A1 | 4/2003 | Schaller et al. |
| 2003/0078617 A1 | 4/2003 | Schwartz et al. |
| 2003/0083662 A1 | 5/2003 | Middleton |
| 2003/0083694 A1 | 5/2003 | Miller |
| 2003/0088251 A1 | 5/2003 | Braun et al. |
| 2003/0088272 A1 | 5/2003 | Smith |
| 2003/0105477 A1 | 6/2003 | Schwartz et al. |
| 2003/0105489 A1 | 6/2003 | Eichhorn et al. |
| 2003/0120309 A1 | 6/2003 | Colleran et al. |
| 2003/0130670 A1 | 7/2003 | Anderson et al. |
| 2003/0130694 A1 | 7/2003 | Bojarski et al. |
| 2003/0130695 A1 | 7/2003 | McDevitt et al. |
| 2003/0135214 A1 | 7/2003 | Fetto et al. |
| 2003/0135239 A1 | 7/2003 | Gabriel et al. |
| 2003/0135963 A1 | 7/2003 | Holbrook et al. |
| 2003/0139752 A1 | 7/2003 | Pasricha et al. |
| 2003/0139775 A1 | 7/2003 | Grafton |
| 2003/0149448 A1 | 8/2003 | Foerster et al. |
| 2003/0152522 A1 | 8/2003 | Miller et al. |
| 2003/0153947 A1 | 8/2003 | Koseki |
| 2003/0167072 A1 | 9/2003 | Oberlander |
| 2003/0167090 A1 | 9/2003 | Chervitz et al. |
| 2003/0171811 A1 | 9/2003 | Steiner et al. |
| 2003/0176865 A1 | 9/2003 | Supinski |
| 2003/0176919 A1 | 9/2003 | Schmieding |

(56) References Cited

U.S. PATENT DOCUMENTS

| | | |
|---|---|---|
| 2003/0176920 A1 | 9/2003 | Sklar et al. |
| 2003/0181925 A1 | 9/2003 | Bain et al. |
| 2003/0195528 A1 | 10/2003 | Ritchart |
| 2003/0195564 A1 | 10/2003 | Tran et al. |
| 2003/0208209 A1 | 11/2003 | Gambale et al. |
| 2003/0208210 A1 | 11/2003 | Dreyfuss et al. |
| 2003/0212456 A1 | 11/2003 | Lipchitz et al. |
| 2003/0216809 A1 | 11/2003 | Ferguson |
| 2003/0220646 A1 | 11/2003 | Thelen et al. |
| 2003/0220660 A1 | 11/2003 | Kortenbach et al. |
| 2003/0225459 A1 | 12/2003 | Hammer et al. |
| 2003/0229361 A1 | 12/2003 | Jackson |
| 2003/0229396 A1 | 12/2003 | Andrews |
| 2003/0236555 A1 | 12/2003 | Thornes |
| 2004/0002734 A1 | 1/2004 | Fallin et al. |
| 2004/0006345 A1 | 1/2004 | Vlahos et al. |
| 2004/0006346 A1 | 1/2004 | Holmen et al. |
| 2004/0015171 A1 | 1/2004 | Bojarski et al. |
| 2004/0015172 A1 | 1/2004 | Biedermann et al. |
| 2004/0024456 A1 | 2/2004 | Brown et al. |
| 2004/0024457 A1 | 2/2004 | Boyce et al. |
| 2004/0039389 A1 | 2/2004 | West et al. |
| 2004/0044391 A1 | 3/2004 | Porter |
| 2004/0059357 A1 | 3/2004 | Koseki |
| 2004/0073176 A1 | 4/2004 | Utterberg |
| 2004/0087981 A1 | 5/2004 | Berube et al. |
| 2004/0092936 A1 | 5/2004 | Miller et al. |
| 2004/0093031 A1 | 5/2004 | Burkhart et al. |
| 2004/0093032 A1 | 5/2004 | Sinnott et al. |
| 2004/0098051 A1 | 5/2004 | Fallin et al. |
| 2004/0098053 A1 | 5/2004 | Tran |
| 2004/0111117 A1 | 6/2004 | Colleran et al. |
| 2004/0122431 A1 | 6/2004 | Biedermann et al. |
| 2004/0127907 A1 | 7/2004 | Dakin et al. |
| 2004/0133206 A1 | 7/2004 | Stevens et al. |
| 2004/0133211 A1 | 7/2004 | Raskin et al. |
| 2004/0138664 A1 | 7/2004 | Bowman |
| 2004/0138683 A1 | 7/2004 | Shelton et al. |
| 2004/0138704 A1 | 7/2004 | Gambale et al. |
| 2004/0138706 A1 | 7/2004 | Abrams et al. |
| 2004/0138747 A1 | 7/2004 | Kaladelfos |
| 2004/0143344 A1 | 7/2004 | Malaviya et al. |
| 2004/0147932 A1 | 7/2004 | Burkinshaw et al. |
| 2004/0147958 A1 | 7/2004 | Lam et al. |
| 2004/0153103 A1 | 8/2004 | Schwartz et al. |
| 2004/0153153 A1 | 8/2004 | Elson et al. |
| 2004/0162579 A1 | 8/2004 | Foerster |
| 2004/0166169 A1 | 8/2004 | Malaviya et al. |
| 2004/0181234 A1 | 9/2004 | McDevitt et al. |
| 2004/0182968 A1 | 9/2004 | Gentry |
| 2004/0187314 A1 | 9/2004 | Johnson |
| 2004/0193185 A1 | 9/2004 | McBrayer |
| 2004/0199169 A1 | 10/2004 | Koons et al. |
| 2004/0204722 A1 | 10/2004 | Sikora et al. |
| 2004/0220574 A1 | 11/2004 | Pelo et al. |
| 2004/0225183 A1 | 11/2004 | Michlitsch et al. |
| 2004/0225292 A1 | 11/2004 | Sasso et al. |
| 2004/0225305 A1* | 11/2004 | Ewers et al. ............ 606/153 |
| 2004/0236353 A1 | 11/2004 | Bain et al. |
| 2004/0236373 A1 | 11/2004 | Anspach |
| 2004/0243139 A1 | 12/2004 | Lewis et al. |
| 2004/0243178 A1 | 12/2004 | Haut et al. |
| 2004/0243180 A1 | 12/2004 | Donnelly et al. |
| 2004/0243235 A1 | 12/2004 | Goh et al. |
| 2004/0249394 A1 | 12/2004 | Morris et al. |
| 2004/0260296 A1 | 12/2004 | Kaiser et al. |
| 2004/0260298 A1 | 12/2004 | Kaiser et al. |
| 2004/0267164 A1 | 12/2004 | Rhodes et al. |
| 2004/0267265 A1 | 12/2004 | Kyle |
| 2004/0267270 A1 | 12/2004 | Jacobs et al. |
| 2004/0267276 A1 | 12/2004 | Camino et al. |
| 2004/0267277 A1 | 12/2004 | Zannis et al. |
| 2004/0267286 A1 | 12/2004 | Gao et al. |
| 2004/0267304 A1 | 12/2004 | Zannis et al. |
| 2004/0267309 A1 | 12/2004 | Garvin |
| 2004/0267317 A1 | 12/2004 | Higgins et al. |
| 2004/0267361 A1 | 12/2004 | Donnelly et al. |
| 2004/0267362 A1 | 12/2004 | Hwang et al. |
| 2005/0004670 A1 | 1/2005 | Gebhardt et al. |
| 2005/0021087 A1 | 1/2005 | Koseki |
| 2005/0021148 A1 | 1/2005 | Gibbs |
| 2005/0027307 A1 | 2/2005 | Schwartz et al. |
| 2005/0033363 A1 | 2/2005 | Bojarski et al. |
| 2005/0038426 A1 | 2/2005 | Chan |
| 2005/0049598 A1 | 3/2005 | West, Jr. et al. |
| 2005/0055027 A1 | 3/2005 | Yeung et al. |
| 2005/0055037 A1 | 3/2005 | Fathauer |
| 2005/0064042 A1 | 3/2005 | Vunjak-Novakovic et al. |
| 2005/0065521 A1 | 3/2005 | Steger et al. |
| 2005/0065526 A1 | 3/2005 | Drew et al. |
| 2005/0070906 A1 | 3/2005 | Clark et al. |
| 2005/0070928 A1 | 3/2005 | Heino et al. |
| 2005/0074495 A1 | 4/2005 | Schwartz et al. |
| 2005/0076478 A1 | 4/2005 | Miyazaki et al. |
| 2005/0085819 A1 | 4/2005 | Ellis et al. |
| 2005/0090827 A1 | 4/2005 | Gedebou |
| 2005/0090828 A1 | 4/2005 | Alford |
| 2005/0090862 A1 | 4/2005 | McDevitt et al. |
| 2005/0096696 A1 | 5/2005 | Forsberg |
| 2005/0096697 A1 | 5/2005 | Forsberg et al. |
| 2005/0096743 A1 | 5/2005 | Schmieding et al. |
| 2005/0101957 A1 | 5/2005 | Buskirk et al. |
| 2005/0107795 A1 | 5/2005 | Morris et al. |
| 2005/0107828 A1 | 5/2005 | Reese |
| 2005/0107882 A1 | 5/2005 | Stone et al. |
| 2005/0119531 A1 | 6/2005 | Sharratt |
| 2005/0119696 A1 | 6/2005 | Walters et al. |
| 2005/0124996 A1 | 6/2005 | Hearn |
| 2005/0125031 A1 | 6/2005 | Pipenhagen et al. |
| 2005/0125036 A1 | 6/2005 | Roby |
| 2005/0125073 A1 | 6/2005 | Orban et al. |
| 2005/0130301 A1 | 6/2005 | Mckay et al. |
| 2005/0131413 A1 | 6/2005 | O'Driscoll et al. |
| 2005/0137600 A1 | 6/2005 | Jacobs et al. |
| 2005/0137624 A1 | 6/2005 | Fallman |
| 2005/0149033 A1 | 7/2005 | McGuire et al. |
| 2005/0149118 A1 | 7/2005 | Koyfman et al. |
| 2005/0149122 A1 | 7/2005 | McDevitt et al. |
| 2005/0149187 A1 | 7/2005 | Clark et al. |
| 2005/0159812 A1 | 7/2005 | Dinger et al. |
| 2005/0165416 A1 | 7/2005 | Bojarski et al. |
| 2005/0165482 A1 | 7/2005 | Goldhahn et al. |
| 2005/0171547 A1 | 8/2005 | Aram |
| 2005/0171603 A1 | 8/2005 | Justin et al. |
| 2005/0171604 A1 | 8/2005 | Michalow |
| 2005/0177237 A1 | 8/2005 | Shappley et al. |
| 2005/0187565 A1 | 8/2005 | Baker et al. |
| 2005/0187577 A1 | 8/2005 | Selvitelli et al. |
| 2005/0187635 A1 | 8/2005 | Metzger |
| 2005/0192632 A1 | 9/2005 | Geissler et al. |
| 2005/0203620 A1 | 9/2005 | Steiner et al. |
| 2005/0222618 A1 | 10/2005 | Dreyfuss et al. |
| 2005/0222619 A1 | 10/2005 | Dreyfuss et al. |
| 2005/0228448 A1 | 10/2005 | Li |
| 2005/0240198 A1 | 10/2005 | Albertson et al. |
| 2005/0251153 A1 | 11/2005 | Sakamoto et al. |
| 2005/0251159 A1 | 11/2005 | Ewers et al. |
| 2005/0251177 A1 | 11/2005 | Saadat et al. |
| 2005/0251208 A1 | 11/2005 | Elmer et al. |
| 2005/0251209 A1 | 11/2005 | Saadat et al. |
| 2005/0251210 A1 | 11/2005 | Westra et al. |
| 2005/0261642 A1 | 11/2005 | Weston |
| 2005/0267479 A1 | 12/2005 | Morgan et al. |
| 2005/0267533 A1 | 12/2005 | Gertner |
| 2005/0277939 A1 | 12/2005 | Miller |
| 2005/0277961 A1 | 12/2005 | Stone et al. |
| 2005/0283040 A1 | 12/2005 | Greenhalgh |
| 2005/0283156 A1 | 12/2005 | Schmieding et al. |
| 2005/0283158 A1 | 12/2005 | West |
| 2005/0283192 A1 | 12/2005 | Torrie et al. |
| 2006/0004364 A1 | 1/2006 | Green et al. |
| 2006/0004410 A1 | 1/2006 | Nobis et al. |
| 2006/0015103 A1 | 1/2006 | Burke |
| 2006/0015106 A1 | 1/2006 | Lerch et al. |

(56) References Cited

U.S. PATENT DOCUMENTS

| | | |
|---|---|---|
| 2006/0015107 A1 | 1/2006 | Sklar |
| 2006/0030884 A1 | 2/2006 | Yeung et al. |
| 2006/0030948 A1 | 2/2006 | Manrique et al. |
| 2006/0036265 A1 | 2/2006 | Dant |
| 2006/0052787 A1 | 3/2006 | Re et al. |
| 2006/0052818 A1 | 3/2006 | Drake et al. |
| 2006/0064125 A1 | 3/2006 | Henderson et al. |
| 2006/0064126 A1 | 3/2006 | Fallin et al. |
| 2006/0069334 A1 | 3/2006 | Moskowitz |
| 2006/0079904 A1 | 4/2006 | Thal |
| 2006/0084943 A1 | 4/2006 | Rosenman et al. |
| 2006/0085000 A1 | 4/2006 | Mohr et al. |
| 2006/0089672 A1 | 4/2006 | Martinek |
| 2006/0095130 A1 | 5/2006 | Caborn et al. |
| 2006/0095131 A1 | 5/2006 | Justin et al. |
| 2006/0100627 A1 | 5/2006 | Stone et al. |
| 2006/0100637 A1 | 5/2006 | Rathbun et al. |
| 2006/0106423 A1 | 5/2006 | Weisel et al. |
| 2006/0111721 A1 | 5/2006 | Puricelli et al. |
| 2006/0116685 A1 | 6/2006 | Urbanski et al. |
| 2006/0121084 A1 | 6/2006 | Borden et al. |
| 2006/0122608 A1 | 6/2006 | Fallin et al. |
| 2006/0122611 A1 | 6/2006 | Morales et al. |
| 2006/0135958 A1 | 6/2006 | Marissen et al. |
| 2006/0149258 A1 | 7/2006 | Sousa |
| 2006/0149266 A1 | 7/2006 | Cordasco |
| 2006/0155287 A1 | 7/2006 | Montgomery et al. |
| 2006/0155328 A1 | 7/2006 | Foerster |
| 2006/0161161 A1 | 7/2006 | Shifrin et al. |
| 2006/0167458 A1 | 7/2006 | Gabele |
| 2006/0167481 A1 | 7/2006 | Baker et al. |
| 2006/0167482 A1 | 7/2006 | Swain et al. |
| 2006/0173492 A1 | 8/2006 | Akerfeldt et al. |
| 2006/0178680 A1 | 8/2006 | Nelson et al. |
| 2006/0178743 A1 | 8/2006 | Carter |
| 2006/0189993 A1 | 8/2006 | Stone |
| 2006/0190042 A1 | 8/2006 | Stone et al. |
| 2006/0195101 A1 | 8/2006 | Stevens |
| 2006/0195106 A1 | 8/2006 | Jones et al. |
| 2006/0200235 A1 | 9/2006 | Bianchi et al. |
| 2006/0212055 A1 | 9/2006 | Karabey et al. |
| 2006/0229623 A1 | 10/2006 | Bonutti et al. |
| 2006/0229671 A1 | 10/2006 | Steiner et al. |
| 2006/0229676 A1 | 10/2006 | Doll et al. |
| 2006/0235407 A1 | 10/2006 | Wang et al. |
| 2006/0235413 A1 | 10/2006 | Denham et al. |
| 2006/0241624 A1 | 10/2006 | Kizuka et al. |
| 2006/0241776 A1 | 10/2006 | Brown et al. |
| 2006/0241781 A1 | 10/2006 | Brown et al. |
| 2006/0247642 A1 | 11/2006 | Stone et al. |
| 2006/0253130 A1 | 11/2006 | Wolniewicz |
| 2006/0259048 A1 | 11/2006 | Koseki |
| 2006/0259076 A1 | 11/2006 | Burkhart et al. |
| 2006/0264944 A1 | 11/2006 | Cole |
| 2006/0271192 A1 | 11/2006 | Olsen et al. |
| 2006/0276793 A1 | 12/2006 | Berry |
| 2006/0276809 A1 | 12/2006 | Oliveira |
| 2006/0276841 A1 | 12/2006 | Barbieri et al. |
| 2006/0276896 A1 | 12/2006 | Fallin et al. |
| 2006/0280768 A1 | 12/2006 | Hwang et al. |
| 2006/0280803 A1 | 12/2006 | Kumar et al. |
| 2006/0282082 A1 | 12/2006 | Fanton et al. |
| 2006/0282083 A1 | 12/2006 | Fanton et al. |
| 2006/0282085 A1 | 12/2006 | Stone et al. |
| 2006/0293709 A1 | 12/2006 | Bojarski et al. |
| 2007/0005068 A1 | 1/2007 | Sklar |
| 2007/0005080 A1 | 1/2007 | Wolniewicz et al. |
| 2007/0010857 A1 | 1/2007 | Sugimoto et al. |
| 2007/0016305 A1 | 1/2007 | Chudik |
| 2007/0021779 A1 | 1/2007 | Garvin et al. |
| 2007/0027476 A1 | 2/2007 | Harris et al. |
| 2007/0032800 A1 | 2/2007 | Ortiz et al. |
| 2007/0032823 A1* | 2/2007 | Tegg .................. 606/232 |
| 2007/0038218 A1 | 2/2007 | Grevious |
| 2007/0043371 A1 | 2/2007 | Teague et al. |
| 2007/0055249 A1 | 3/2007 | Jensen et al. |
| 2007/0055251 A1 | 3/2007 | Huebner et al. |
| 2007/0055255 A1 | 3/2007 | Siegel |
| 2007/0060922 A1 | 3/2007 | Dreyfuss |
| 2007/0067025 A1 | 3/2007 | Schwartz |
| 2007/0071568 A1 | 3/2007 | Dorstewitz |
| 2007/0073307 A1 | 3/2007 | Scribner et al. |
| 2007/0073319 A1 | 3/2007 | Mikkaichi et al. |
| 2007/0073322 A1 | 3/2007 | Mikkaichi et al. |
| 2007/0078435 A1 | 4/2007 | Stone et al. |
| 2007/0083236 A1 | 4/2007 | Sikora et al. |
| 2007/0088362 A1 | 4/2007 | Bonutti et al. |
| 2007/0093847 A1 | 4/2007 | Scribner et al. |
| 2007/0100350 A1 | 5/2007 | Deffenbaugh et al. |
| 2007/0112384 A1 | 5/2007 | Conlon et al. |
| 2007/0118217 A1 | 5/2007 | Brulez et al. |
| 2007/0123883 A1 | 5/2007 | Ellis et al. |
| 2007/0123984 A1 | 5/2007 | Hodorek |
| 2007/0129809 A1 | 6/2007 | Meridew et al. |
| 2007/0142838 A1 | 6/2007 | Jordan |
| 2007/0156174 A1 | 7/2007 | Kaiser et al. |
| 2007/0162018 A1 | 7/2007 | Jensen et al. |
| 2007/0167926 A1 | 7/2007 | Blott et al. |
| 2007/0167950 A1 | 7/2007 | Tauro et al. |
| 2007/0173948 A1 | 7/2007 | Meridew et al. |
| 2007/0185488 A1 | 8/2007 | Pohjonen et al. |
| 2007/0185532 A1 | 8/2007 | Stone et al. |
| 2007/0185568 A1 | 8/2007 | Schwartz |
| 2007/0191849 A1 | 8/2007 | ElAttrache et al. |
| 2007/0191853 A1 | 8/2007 | Stone |
| 2007/0198022 A1 | 8/2007 | Lang et al. |
| 2007/0198036 A1 | 8/2007 | Sklar et al. |
| 2007/0219558 A1 | 9/2007 | Deutsch |
| 2007/0225715 A1 | 9/2007 | Deffenbaugh et al. |
| 2007/0225719 A1 | 9/2007 | Stone et al. |
| 2007/0225805 A1 | 9/2007 | Schmieding |
| 2007/0233241 A1 | 10/2007 | Graf et al. |
| 2007/0239209 A1 | 10/2007 | Fallman |
| 2007/0239275 A1 | 10/2007 | Willobee |
| 2007/0244565 A1 | 10/2007 | Stchur |
| 2007/0250059 A1 | 10/2007 | Weisshaupt et al. |
| 2007/0250163 A1 | 10/2007 | Cassani |
| 2007/0250175 A1 | 10/2007 | Meridew et al. |
| 2007/0260251 A1 | 11/2007 | Weier et al. |
| 2007/0260279 A1 | 11/2007 | Hotter et al. |
| 2007/0265704 A1 | 11/2007 | Mayer et al. |
| 2007/0270856 A1 | 11/2007 | Morales et al. |
| 2007/0270878 A1 | 11/2007 | Leisinger |
| 2007/0276387 A1 | 11/2007 | Morales et al. |
| 2007/0288023 A1 | 12/2007 | Pellegrino et al. |
| 2008/0027430 A1 | 1/2008 | Montgomery et al. |
| 2008/0027440 A1 | 1/2008 | Marissen et al. |
| 2008/0027446 A1 | 1/2008 | Stone et al. |
| 2008/0033549 A1 | 2/2008 | Marshall et al. |
| 2008/0046009 A1 | 2/2008 | Albertorio et al. |
| 2008/0051836 A1 | 2/2008 | Foerster et al. |
| 2008/0058787 A1 | 3/2008 | Gertner |
| 2008/0065114 A1 | 3/2008 | Stone et al. |
| 2008/0071299 A1 | 3/2008 | Allinniemi et al. |
| 2008/0082101 A1 | 4/2008 | Reisberg |
| 2008/0082127 A1 | 4/2008 | Stone et al. |
| 2008/0082128 A1 | 4/2008 | Stone |
| 2008/0097430 A1 | 4/2008 | Bernstein et al. |
| 2008/0114460 A1 | 5/2008 | Willobee et al. |
| 2008/0119892 A1 | 5/2008 | Brailovski et al. |
| 2008/0132753 A1 | 6/2008 | Goddard |
| 2008/0132932 A1 | 6/2008 | Hoeppner et al. |
| 2008/0132948 A1 | 6/2008 | Surti et al. |
| 2008/0133007 A1 | 6/2008 | Donnelly et al. |
| 2008/0140092 A1 | 6/2008 | Stone et al. |
| 2008/0140093 A1 | 6/2008 | Stone et al. |
| 2008/0140128 A1 | 6/2008 | Smisson et al. |
| 2008/0147187 A1 | 6/2008 | Bollinger et al. |
| 2008/0154260 A1 | 6/2008 | Hoof |
| 2008/0154314 A1 | 6/2008 | McDevitt |
| 2008/0161806 A1 | 7/2008 | Donnelly et al. |
| 2008/0161852 A1 | 7/2008 | Kaiser et al. |
| 2008/0161861 A1 | 7/2008 | Huebner |
| 2008/0161864 A1 | 7/2008 | Beck et al. |

(56) References Cited

U.S. PATENT DOCUMENTS

| | | |
|---|---|---|
| 2008/0166421 A1 | 7/2008 | Buhr et al. |
| 2008/0172097 A1 | 7/2008 | Lerch et al. |
| 2008/0177302 A1 | 7/2008 | Shurnas |
| 2008/0183290 A1 | 7/2008 | Baird et al. |
| 2008/0188933 A1 | 8/2008 | Koob et al. |
| 2008/0188936 A1 | 8/2008 | Ball et al. |
| 2008/0208252 A1 | 8/2008 | Holmes |
| 2008/0217263 A1 | 9/2008 | Higgins et al. |
| 2008/0221527 A1 | 9/2008 | Bradley et al. |
| 2008/0221578 A1 | 9/2008 | Zeitani |
| 2008/0228186 A1 | 9/2008 | Gall et al. |
| 2008/0234730 A1 | 9/2008 | Cotton et al. |
| 2008/0255613 A1 | 10/2008 | Kaiser et al. |
| 2008/0257363 A1 | 10/2008 | Schoenefeld et al. |
| 2008/0262544 A1 | 10/2008 | Burkhart |
| 2008/0268064 A1 | 10/2008 | Woodell-May |
| 2008/0269674 A1 | 10/2008 | Stone |
| 2008/0275477 A1 | 11/2008 | Sterrett et al. |
| 2008/0281428 A1 | 11/2008 | Meyers et al. |
| 2008/0300611 A1 | 12/2008 | Houser et al. |
| 2008/0312689 A1 | 12/2008 | Denham et al. |
| 2008/0319478 A1 | 12/2008 | Foerster et al. |
| 2009/0018589 A1 | 1/2009 | Smisson, III et al. |
| 2009/0018655 A1 | 1/2009 | Brunelle et al. |
| 2009/0043342 A1 | 2/2009 | Freedland |
| 2009/0054928 A1 | 2/2009 | Denham et al. |
| 2009/0062847 A1 | 3/2009 | Ken |
| 2009/0062854 A1 | 3/2009 | Kaiser et al. |
| 2009/0082790 A1 | 3/2009 | Shad et al. |
| 2009/0082805 A1 | 3/2009 | Kaiser et al. |
| 2009/0084491 A1 | 4/2009 | Uthgenannt et al. |
| 2009/0099598 A1 | 4/2009 | McDevitt et al. |
| 2009/0105717 A1 | 4/2009 | Bluechel |
| 2009/0105754 A1 | 4/2009 | Sethi |
| 2009/0118774 A1 | 5/2009 | Miller, III |
| 2009/0118775 A1 | 5/2009 | Burke |
| 2009/0125073 A1 | 5/2009 | Rehm |
| 2009/0138002 A1 | 5/2009 | Fenton |
| 2009/0138054 A1 | 5/2009 | Teague et al. |
| 2009/0156997 A1 | 6/2009 | Trenhaile |
| 2009/0163949 A1 | 6/2009 | Rolnick et al. |
| 2009/0177233 A1 | 7/2009 | Malek |
| 2009/0192468 A1 | 7/2009 | Stone |
| 2009/0198277 A1 | 8/2009 | Gordon et al. |
| 2009/0204146 A1 | 8/2009 | Kaiser et al. |
| 2009/0216325 A1 | 8/2009 | May et al. |
| 2009/0228042 A1 | 9/2009 | Koogle, Jr. et al. |
| 2009/0234357 A1 | 9/2009 | Morales et al. |
| 2009/0234358 A1 | 9/2009 | Morales et al. |
| 2009/0240251 A1 | 9/2009 | Gabele |
| 2009/0240335 A1 | 9/2009 | Arcenio et al. |
| 2009/0248091 A1 | 10/2009 | Teague et al. |
| 2009/0265014 A1 | 10/2009 | May et al. |
| 2009/0265015 A1 | 10/2009 | May et al. |
| 2009/0287215 A1 | 11/2009 | Fisher et al. |
| 2009/0299409 A1 | 12/2009 | Coe et al. |
| 2009/0306711 A1 | 12/2009 | Stone et al. |
| 2009/0312776 A1 | 12/2009 | Kaiser et al. |
| 2009/0312793 A1 | 12/2009 | Huxel et al. |
| 2009/0318960 A1 | 12/2009 | Burkhart |
| 2009/0318961 A1 | 12/2009 | Stone et al. |
| 2010/0016899 A1 | 1/2010 | Gelfand |
| 2010/0042114 A1 | 2/2010 | Schaffhausen |
| 2010/0063541 A1 | 3/2010 | Brunelle et al. |
| 2010/0087857 A1 | 4/2010 | Stone et al. |
| 2010/0094355 A1 | 4/2010 | Trenhaile |
| 2010/0106254 A1 | 4/2010 | Delsignore |
| 2010/0121348 A1 | 5/2010 | Van Der Burg et al. |
| 2010/0145384 A1 | 6/2010 | Stone et al. |
| 2010/0152752 A1 | 6/2010 | Denove et al. |
| 2010/0191342 A1 | 7/2010 | Byrd et al. |
| 2010/0204700 A1 | 8/2010 | Falahee |
| 2010/0211071 A1 | 8/2010 | Lettmann et al. |
| 2010/0211075 A1 | 8/2010 | Stone |
| 2010/0256677 A1 | 10/2010 | Albertorio et al. |
| 2010/0268273 A1 | 10/2010 | Albertorio et al. |
| 2010/0268275 A1 | 10/2010 | Stone et al. |
| 2010/0270306 A1 | 10/2010 | Shiffer |
| 2010/0292792 A1 | 11/2010 | Stone et al. |
| 2010/0305698 A1 | 12/2010 | Metzger et al. |
| 2010/0305709 A1 | 12/2010 | Metzger et al. |
| 2010/0312341 A1 | 12/2010 | Kaiser et al. |
| 2011/0009885 A1 | 1/2011 | Graf et al. |
| 2011/0022083 A1 | 1/2011 | DiMatteo et al. |
| 2011/0026141 A1 | 2/2011 | Barrows |
| 2011/0046733 A1 | 2/2011 | Eggli |
| 2011/0087225 A1 | 4/2011 | Fritzinger |
| 2011/0087284 A1 | 4/2011 | Stone et al. |
| 2011/0098727 A1 | 4/2011 | Kaiser et al. |
| 2011/0106153 A1 | 5/2011 | Stone et al. |
| 2011/0112537 A1 | 5/2011 | Bernstein et al. |
| 2011/0112538 A1 | 5/2011 | Dell'Oca |
| 2011/0160767 A1 | 6/2011 | Stone et al. |
| 2011/0160768 A1 | 6/2011 | Stone et al. |
| 2011/0208239 A1 | 8/2011 | Stone et al. |
| 2011/0208240 A1 | 8/2011 | Stone et al. |
| 2011/0213416 A1 | 9/2011 | Kaiser |
| 2011/0218625 A1 | 9/2011 | Berelsman et al. |
| 2011/0224799 A1 | 9/2011 | Stone |
| 2011/0245868 A1 | 10/2011 | Teeslink et al. |
| 2011/0264141 A1 | 10/2011 | Denham et al. |
| 2011/0270278 A1 | 11/2011 | Overes et al. |
| 2011/0270306 A1 | 11/2011 | Denham et al. |
| 2012/0004669 A1 | 1/2012 | Overes et al. |
| 2012/0041485 A1 | 2/2012 | Kaiser et al. |
| 2012/0041486 A1 | 2/2012 | Stone et al. |
| 2012/0046693 A1 | 2/2012 | Denham et al. |
| 2012/0053630 A1 | 3/2012 | Denham et al. |
| 2012/0059417 A1 | 3/2012 | Norton et al. |
| 2012/0059418 A1 | 3/2012 | Denham et al. |
| 2012/0059468 A1 | 3/2012 | Mattern et al. |
| 2012/0089193 A1 | 4/2012 | Stone et al. |
| 2012/0095470 A1 | 4/2012 | Kaiser et al. |
| 2012/0109156 A1 | 5/2012 | Overes et al. |
| 2012/0116409 A1 | 5/2012 | Stone |
| 2012/0116450 A1 | 5/2012 | McDevitt et al. |
| 2012/0116452 A1 | 5/2012 | Stone et al. |
| 2012/0123447 A1 | 5/2012 | Corrao et al. |
| 2012/0123474 A1 | 5/2012 | Zajac et al. |
| 2012/0123541 A1 | 5/2012 | Albertorio et al. |
| 2012/0143215 A1 | 6/2012 | Corrao et al. |
| 2012/0150223 A1 | 6/2012 | Manos et al. |
| 2012/0150297 A1 | 6/2012 | Denham et al. |
| 2012/0165866 A1 | 6/2012 | Kaiser et al. |
| 2012/0165867 A1 | 6/2012 | Denham et al. |
| 2012/0165938 A1 | 6/2012 | Denham et al. |
| 2012/0197271 A1 | 8/2012 | Astorino et al. |
| 2012/0215257 A1 | 8/2012 | McDevitt et al. |
| 2012/0245585 A1 | 9/2012 | Kaiser et al. |
| 2012/0265219 A1 | 10/2012 | Rushdy et al. |
| 2012/0290003 A1 | 11/2012 | Dreyfuss |
| 2012/0290004 A1 | 11/2012 | Lombardo et al. |
| 2012/0296427 A1 | 11/2012 | Conner et al. |
| 2012/0310245 A1 | 12/2012 | Hoeppner et al. |
| 2013/0018375 A1 | 1/2013 | Dell'Oca |
| 2013/0018416 A1 | 1/2013 | Lombardo et al. |
| 2013/0023928 A1 | 1/2013 | Dreyfuss |
| 2013/0023929 A1 | 1/2013 | Sullivan et al. |
| 2013/0023930 A1 | 1/2013 | Stone et al. |
| 2013/0035698 A1 | 2/2013 | Stone et al. |
| 2013/0035722 A1 | 2/2013 | McDevitt et al. |
| 2013/0046341 A1 | 2/2013 | Stone et al. |
| 2013/0103082 A1 | 4/2013 | Kaiser et al. |
| 2013/0110165 A1 | 5/2013 | Burkhart et al. |
| 2013/0110251 A1 | 5/2013 | Metzger et al. |
| 2013/0116730 A1 | 5/2013 | Denham et al. |
| 2013/0123810 A1 | 5/2013 | Brown et al. |
| 2013/0123813 A1 | 5/2013 | Stone et al. |
| 2013/0131722 A1 | 5/2013 | Marchand et al. |
| 2013/0138123 A1 | 5/2013 | Stone et al. |
| 2013/0144337 A1 | 6/2013 | Stone et al. |
| 2013/0144338 A1 | 6/2013 | Stone et al. |
| 2013/0158601 A1 | 6/2013 | Stone et al. |
| 2013/0190818 A1 | 7/2013 | Norton |

(56) References Cited

U.S. PATENT DOCUMENTS

| | | |
|---|---|---|
| 2013/0190819 A1 | 7/2013 | Norton |
| 2013/0204276 A1 | 8/2013 | Stone et al. |
| 2013/0211452 A1 | 8/2013 | Stone et al. |
| 2013/0237997 A1 | 9/2013 | Arai et al. |
| 2013/0245761 A1 | 9/2013 | Conner et al. |
| 2013/0274812 A1 | 10/2013 | Dell'Oca |
| 2013/0289564 A1 | 10/2013 | Bernstein et al. |
| 2013/0317621 A1 | 11/2013 | Metzger et al. |
| 2013/0331848 A1 | 12/2013 | Kaiser et al. |
| 2014/0046367 A1 | 2/2014 | Stone et al. |
| 2014/0046368 A1 | 2/2014 | Kaiser et al. |
| 2014/0067081 A1 | 3/2014 | Stone |
| 2014/0088655 A1 | 3/2014 | Stone et al. |
| 2014/0094913 A1 | 4/2014 | Berelsman et al. |
| 2014/0135835 A1 | 5/2014 | Stone et al. |
| 2014/0163613 A1 | 6/2014 | Stone et al. |
| 2014/0163614 A1 | 6/2014 | Denham et al. |
| 2014/0194927 A1 | 7/2014 | Kaiser et al. |
| 2014/0200583 A1 | 7/2014 | Stone et al. |
| 2014/0257378 A1 | 9/2014 | Norton et al. |
| 2014/0276992 A1 | 9/2014 | Stone et al. |
| 2014/0277447 A1 | 9/2014 | Berelsman et al. |
| 2014/0324101 A1 | 10/2014 | Denham et al. |
| 2014/0330311 A1 | 11/2014 | Denham et al. |
| 2014/0350674 A1 | 11/2014 | Stone et al. |
| 2015/0012094 A1 | 1/2015 | Denham et al. |
| 2015/0057757 A1 | 2/2015 | Metzger et al. |
| 2015/0119890 A1 | 4/2015 | Kaiser et al. |
| 2015/0127051 A1 | 5/2015 | Kaiser et al. |
| 2015/0134000 A1 | 5/2015 | Denham et al. |
| 2015/0173887 A1 | 6/2015 | Berelsman et al. |
| 2015/0257750 A1 | 9/2015 | Kaiser et al. |
| 2016/0000483 A1 | 1/2016 | Stone |
| 2016/0022261 A1 | 1/2016 | Stone et al. |
| 2016/0058436 A1 | 3/2016 | Stone et al. |

FOREIGN PATENT DOCUMENTS

| | | |
|---|---|---|
| AU | 4381268 A | 4/1970 |
| AU | 5850469 | 1/1971 |
| AU | 5963869 | 2/1971 |
| AU | 1505470 | 11/1971 |
| AU | 2223767 | 5/1973 |
| AU | 3615171 | 5/1973 |
| AU | 5028569 | 9/1973 |
| AU | 7110887 | 10/1987 |
| AU | 639410 | 11/1989 |
| AU | 639410 A | 11/1989 |
| AU | 1713188 A | 11/1989 |
| AU | 651929 | 8/1994 |
| AU | 651929 B2 | 8/1994 |
| CN | 105208970 A | 12/2015 |
| DE | 2529669 | 3/1976 |
| DE | 2747312 | 4/1979 |
| DE | 2818254 | 10/1979 |
| DE | 2919009 | 11/1979 |
| DE | 3027138 | 12/1981 |
| DE | 3225620 | 2/1983 |
| DE | 3136083 | 3/1983 |
| DE | 233303 C | 2/1986 |
| DE | 4127550 | 2/1993 |
| DE | 4302397 | 7/1993 |
| DE | 29621340 | 5/1998 |
| DE | 19841252 | 3/2000 |
| DE | 29922088 U1 | 4/2000 |
| DE | 20207781 U1 | 8/2002 |
| EP | 19062 A1 | 11/1980 |
| EP | 0108912 | 5/1984 |
| EP | 0129422 | 12/1984 |
| EP | 0129442 | 12/1984 |
| EP | 0172130 | 2/1986 |
| EP | 0241240 | 10/1987 |
| EP | 0241792 | 10/1987 |
| EP | 0260970 | 3/1988 |
| EP | 0270704 | 6/1988 |
| EP | 0282789 | 9/1988 |
| EP | 0315371 | 5/1989 |
| EP | 0317406 | 5/1989 |
| EP | 0340159 | 11/1989 |
| EP | 0346183 | 12/1989 |
| EP | 0349173 | 1/1990 |
| EP | 0374088 | 6/1990 |
| EP | 0409364 | 1/1991 |
| EP | 0415915 | 3/1991 |
| EP | 0440991 | 8/1991 |
| EP | 0441065 | 8/1991 |
| EP | 0447065 A2 | 9/1991 |
| EP | 0451932 | 10/1991 |
| EP | 0464480 | 1/1992 |
| EP | 0490417 | 6/1992 |
| EP | 0497079 | 8/1992 |
| EP | 0502509 | 9/1992 |
| EP | 0502698 | 9/1992 |
| EP | 520177 | 12/1992 |
| EP | 0546726 | 6/1993 |
| EP | 0574707 | 12/1993 |
| EP | 0582514 | 2/1994 |
| EP | 0591991 | 4/1994 |
| EP | 0598219 | 5/1994 |
| EP | 0611551 A1 | 8/1994 |
| EP | 0627203 | 12/1994 |
| EP | 0651979 | 5/1995 |
| EP | 0669110 | 8/1995 |
| EP | 0686373 | 12/1995 |
| EP | 0702933 | 3/1996 |
| EP | 0775473 | 5/1997 |
| EP | 0913123 | 5/1999 |
| EP | 0913131 | 5/1999 |
| EP | 99121106 | 10/1999 |
| EP | 991210527 | 10/1999 |
| EP | 0995409 | 4/2000 |
| EP | 1013229 | 6/2000 |
| EP | 1093773 | 4/2001 |
| EP | 1093774 | 4/2001 |
| EP | 1555945 | 7/2005 |
| EP | 1741412 A2 | 1/2007 |
| EP | 1864617 A2 | 12/2007 |
| EP | 2238944 A2 | 10/2010 |
| EP | 2544607 A1 | 1/2013 |
| EP | 2709557 A1 | 3/2014 |
| FR | 2622790 | 5/1989 |
| FR | 2634373 A1 | 1/1990 |
| FR | 2655840 | 6/1991 |
| FR | 2663837 A1 | 1/1992 |
| FR | 2682867 | 4/1993 |
| FR | 2687911 | 9/1993 |
| FR | 2688689 | 9/1993 |
| FR | 2704140 | 10/1994 |
| FR | 2717070 | 9/1995 |
| FR | 2723528 | 2/1996 |
| FR | 2734709 A1 | 12/1996 |
| FR | 2744010 | 8/1997 |
| FR | 2745999 | 9/1997 |
| FR | 2770764 | 5/1999 |
| GB | 401677 | 11/1933 |
| GB | 1413477 | 11/1975 |
| GB | 1485681 | 9/1977 |
| GB | 2083751 | 3/1982 |
| GB | 2118474 | 11/1983 |
| GB | 2129306 A | 5/1984 |
| GB | 2227175 | 7/1990 |
| GB | 2253147 A | 9/1992 |
| GB | 2312376 | 10/1997 |
| GB | 2403416 A | 1/2005 |
| JP | 5362911 | 5/1978 |
| JP | 5362912 | 5/1978 |
| JP | 5374942 | 6/1978 |
| JP | 5378230 | 6/1978 |
| JP | 54166092 U | 11/1979 |
| JP | 54166093 U | 11/1979 |
| JP | 54176284 U | 12/1979 |
| JP | 54178988 U | 12/1979 |
| JP | 62159647 | 7/1987 |

(56) References Cited

FOREIGN PATENT DOCUMENTS

| | | |
|---|---|---|
| JP | 62295657 | 12/1987 |
| JP | 5269160 | 10/1993 |
| JP | 5300917 | 11/1993 |
| JP | 751292 | 2/1995 |
| JP | 10127672 A | 5/1998 |
| JP | 10211213 | 8/1998 |
| RU | 2051647 C1 | 1/1996 |
| RU | 2076667 C1 | 4/1997 |
| WO | WO-8300615 | 3/1983 |
| WO | WO-8603666 | 7/1986 |
| WO | WO-8701270 | 3/1987 |
| WO | WO-8901767 | 3/1989 |
| WO | WO-8909030 | 10/1989 |
| WO | WO-8910096 | 11/1989 |
| WO | WO-9008510 | 8/1990 |
| WO | WO-9203980 | 3/1992 |
| WO | WO-9314705 | 8/1993 |
| WO | WO-9315694 | 8/1993 |
| WO | WO-9502373 | 1/1995 |
| WO | WO-9503003 | 2/1995 |
| WO | WO-9529637 | 11/1995 |
| WO | WO-9532670 | 12/1995 |
| WO | WO-9609797 A1 | 4/1996 |
| WO | WO-9629029 | 9/1996 |
| WO | WO-9737603 | 10/1997 |
| WO | WO-9812991 | 4/1998 |
| WO | WO-9812992 | 4/1998 |
| WO | WO-9822047 | 5/1998 |
| WO | WO-9822048 | 5/1998 |
| WO | WO-9901084 | 1/1999 |
| WO | WO-9912480 | 3/1999 |
| WO | WO-9937219 A1 | 7/1999 |
| WO | WO-9944544 | 9/1999 |
| WO | WO-9952472 A1 | 10/1999 |
| WO | WO-0004159 A1 | 1/2000 |
| WO | WO-0040159 | 7/2000 |
| WO | WO-0139671 | 6/2001 |
| WO | WO-0236020 | 5/2002 |
| WO | WO-03005914 A1 | 1/2003 |
| WO | WO-03071962 | 9/2003 |
| WO | WO-03077772 | 9/2003 |
| WO | WO-03092551 A1 | 11/2003 |
| WO | WO-2004091412 A1 | 10/2004 |
| WO | WO-2005104992 A1 | 11/2005 |
| WO | WO-2005122954 A1 | 12/2005 |
| WO | WO-2006023661 A2 | 3/2006 |
| WO | WO-2006023661 A2 | 3/2006 |
| WO | WO-2006055823 A2 | 5/2006 |
| WO | WO-2007045460 A2 | 4/2007 |
| WO | WO-2007103562 A2 | 9/2007 |
| WO | WO-2007109280 A2 | 9/2007 |
| WO | WO-2007119057 A1 | 10/2007 |
| WO | WO-2008002550 A2 | 1/2008 |
| WO | WO-2008015171 A1 | 2/2008 |
| WO | WO-2008073588 A2 | 6/2008 |
| WO | WO-2009012021 A1 | 1/2009 |
| WO | WO-2009131820 A1 | 10/2009 |
| WO | WO-2010138832 A1 | 12/2010 |
| WO | WO-2011112371 A1 | 9/2011 |
| WO | WO-2011150238 A1 | 12/2011 |
| WO | WO-2012134999 A1 | 10/2012 |
| WO | WO-2012158583 A1 | 11/2012 |
| WO | WO-2013066974 A1 | 5/2013 |
| WO | WO-2013074525 A1 | 5/2013 |
| WO | WO-2014/100109 A1 | 6/2014 |
| WO | WO-2014151766 A1 | 9/2014 |

OTHER PUBLICATIONS

"Arthroscopic Meniscal Repair using the Meniscal Cinch™", Surgical Technique brochure. (2008) Arthrex® 6 sheets.
"Bio-Intrafix (TCP/PLA & Intrafix, Tibial Soft Tissue Fasteners," by DePuy Mitek, 6 sheets, (date unknown).
"Bio-Intrafix Tibial Soft Tissue Fasteners, Building on the Legacy of IntraFix," brochure. DePuy Mitek,(Feb. 2007) 6 sheets.
"Biomechanical Evaluation of the Biomet Sports Medicine JurggerKnot™ Soft Anchor in Porcine Bone," Study completed Jan. 2010. Biomet Sports Medicine Research and Development, Warsaw, Indiana. 2 pages.
"Do your next distal tendon repair with . . . The Lubbers Technique", Teno Fix® brochure, 2003 (2 pages) Ortheon® Medical.
"EZ Loc Femoral Fixation Device," copyright 2005 Arthrotek, Inc. (8 sheets).
"JuggerKnot™ Soft Anchor Midfoot Repair," brochure. Biomet Sports Medicine (Jul. 2011) 12 sheets.
"JuggerKnot™ Soft Anchor. It's Small. It's strong. and it's all suture . . . " Ordering Information brochure. Biomet Sports Medicine (Jun. 2011) 2 sheets.
"JuggerKnot™ Soft Anchor. Labral Repair," brochure. Biomet Sports Medicine (Apr. 2011) 12 sheets.
"Make your next tendon repair an open-and-shut case. The Teno Fix® Tendon Repair System", Teno Fix® brochure, 2003 (2 pages) Ortheon® Medical.
"Panalok Anchor with PDS II and Ethibond Suture", Mitek Products Ethicon, 1997.
"SE Graft Tensioning System Surgical Technique," Linvatec Corporation copyright 2003, 2004.
"Suture Tensioner w/Tensiometer," Arthrex®, Inc. catalog "Next Generation in Knee Ligament Reconstruction & Repair Technology," 2009.
"Technique for ACL Reconstruction with Acufex Director Drill Guide and Endobutton CL," by Thomas D. Roseberg, copyright 1999 Smith & Nephew.
"TriTis™ Tibial Fixation System and Implant" brochure. Scandius Biomedical (2006).
A. Weiler, et al; Biodegradierbare lnterferenzschrauben in der Kreuzbandchirurgie; OP-Journal 14 pp. 278-284; (Mar. 1998).
Arthrotek, A Biomet Company; Knees; Sure fire Hybrid Meniscal Device. (2005).
Arthrotek, A Biomet Company; Sure fire Hybrid Meniscal Device; Launch Date: Fall AANA 2004.
F. Alan Barber, M.D., "Uses and Abuses of Sutures and Anchors," Shoulder Scope, San Diego Shoulder Arthroscopy Library. http://www.shoulder.com/bass_barber.html Printed May 19, 2005.
F. Alan Barber, M.D., "Using Sutures and Anchors," San Diego Shoulder Arthroscopy Course, 17th Annual Meeting. (Jun. 14, 2000).
Flavia Namie Azato, et al. "Traction endurance biomechanical study of metallic suture anchors at different insertion angles," Acta ortop. bras., vol. 11, No. 1, Sao Paulo, Jan./Mar. 2003.
Hecker AT, et al., "Pull-out strength of suture anchors for rotator cuff and Bankart lesion repairs," Am J Sports Med. 1993.
International Preliminary Report on Patentability mailed Dec. 6, 2012 for PCT/US2011/038188 claiming benefit of U.S. Appl. No. 12/788,966, filed May 27, 2010.
International Preliminary Report on Patentability mailed Sep. 20, 2012 for PCT/US2011/026349 which claims benefit of U.S. Appl. No. 12/719,337, filed Mar. 8, 2010.
International Search Report and Written Opinion mailed Feb. 6, 2013 for PCT/US2012/064832 which claims benefit of U.S. Appl. No. 13/295,126, filed Nov. 14, 2011.
International Search Report and Written Opinion mailed Jul. 28, 2011 for PCT/US2011/026349 claiming benefit of U.S. Appl. No. 12/938,902, filed Nov. 3, 2010; and U.S. Appl. No. 12/719,337, filed Mar. 8, 2010.
International Search Report and Written Opinion mailed Mar. 6, 2013 for PCT/US2012/062738 which claims benefit of U.S. Appl. No. 13/288,459, filed Nov. 3, 2011.
International Search Report and Written Opinion mailed Oct. 14, 2011 for PCT/US2011/038188 filed May 26, 2011 claiming benefit of U.S. Appl. No. 12/788,973, filed May 27, 2010 and U.S. Appl. No. 12/788,966, filed May 27, 2010.
International Search Report and Written Opinion mailed Sep. 21, 2012 for PCT/US2012/037703 filed May 14, 2012 claiming benefit of U.S. Appl. No. 13/109,667, filed May 17, 2011 and U.S. Appl. No. 13/109,672, filed May 17, 2011.
Invitation to Pay Additional Fees mailed Aug. 5, 2011 for PCT/US2011/038188 claiming benefit of U.S. Appl. No. 12/788,973, filed May 27, 2010 and U.S. Appl. No. 12/788,966, filed May 27, 2010.

(56) References Cited

OTHER PUBLICATIONS

Invitation to Pay Additional Fees mailed Jul. 19, 2012, for PCT/US2012/037703 claiming benefit of U.S. Appl. No. 13/109,667, filed May 7, 2011.
Invitation to Pay Additional Fees mailed Jun. 9, 2011 for PCT/US2011/026349 claiming benefit of U.S. Appl. No. 12/938,902, filed Nov. 3, 2010; and U.S. Appl. No. 12/719,337, filed Mar. 8, 2010.
Lawhorn, M.D., Keith, MaxFire™ Meniscal Repair Device with Zip Loop™ Technology, Biomet Sports Medicine, Feb. 29, 2008.
Mark D. Miller et al.; "Pitfalls Associated with FasT-Fix Meniscal Repair," Arthroscopy: The Journal of Arthroscopic and Related Surgery, vol. 18, No. 8 Oct. 2002: pp. 939-943.
Opus Medical; The AutoCuff System; www.opusmedical.com; 2003.
Patrick Hunt, et al.; Development of a Perforated Biodegradable Interference Screw; Arthroscopy: The Journal of Arthroscopic and Related Surgery, vol. 21, No. 3; pp. 258-265; Mar. 2005.
Pioneer® Sternal Cable System (2010).
Rapid Sternal Closure (2006) KLS Martin L.P. http://www.rapidsternalclosure.com/medical/demo.php Web accessed Sep. 8, 2008.
Roy Alan Majors, M.D.; "Meniscal repairs: proven techniques and current trends," Lippincott Williams & Wilkins, Inc.; 2002.
Saxena, Pankaj, MCh, DNB et al., "Use of Double Wires in Sternal Closure, A Useful Technique," Texas Heart® Institute. Journal List>Tex Heart Inst J > v.33(4); (2006).
Shoulder Arthroscopy; pp. H-2-H-22. (date unknown).
Smith & Nephew Endoscopy, "Endoscopic Meniscal Repair Using the T-Fix;" 1996.
Smith & Nephew, "Fast-Fix," Meniscal Repair System; 2001.
Stuart E. Fromm, M.D., RapidLoc, Meniscal Repair System, Mitek Products, Ethicon, 2001.
ToggleLoc™ Femoral Fixation Device, Arthrotek, Mar. 31, 2006.
Zeitani, Jacob, M.D., "A New Sternal Reinforcement Device to Prevent and Treat Sternal Dehiscence," CTSNet.org (Jun. 30, 2008).
"JuggerKnot™ Soft Anchor: Arthroscopic and Mini-Open Rotator Cuff Repair Using JuggerKnot™ Soft Anchor—2.9mm with ALLthread™ Knotless Anchor Surgical Technique" brochure, Biomet® Sports Medicine. (2013) 16 pages.
International Search Report and Written Opinion mailed Mar. 6, 2014 for PCT/US2013/075989 which claims benefit of U.S. Appl. No. 13/720,648, filed Dec. 19, 2012.
"ToggleLoc™ Fixation Device with ZipLoop™ Technology: ACL Reconstruction Bone-Tendon-Bone," by James R. Andrews, M.D., of Biomet Sports Medicine, a Biomet Company Brochure (2013), pp. 1-20.
International Preliminary Report on Patentability and Written Opinion mailed May 30, 2014 for PCT/US2012/064832 which claims benefit of U.S. Appl. No. 13/295,126, filed Nov. 14, 2011.
International Search Report and Written Opinion mailed Jun. 6, 2014 for PCT/US2014/026413 which claims benefit of U.S. Appl. No. 14/095,614, filed Dec. 3, 2013 and U.S. Appl. No. 14/095,639, filed Dec. 3, 2013.
ToggleLoc Fixation Device with ZipLoop Technology: Biceps Tendon Reattachment by Mark J. Albritton, M.D. And Daniel Worrel, M.D. of Biomet Sports Medicine, a Biomet Company Brochure (2099, 2011), pp. 1-12.
International Preliminary Report on Patentability and Written Opinion mailed Nov. 28, 2013 for PCT/US2012/037703, which claims benefit of U.S. Appl. No. 13/109,672, filed May 17, 2011,and U.S. Appl. No. 13/109,667, filed May 17, 2011.
Ziptight™ Fixation System Featuring Zip Loop™ Technology. Ankle Syndesmosis. Surgical Protocol by Timothy Charlton, M.D. Biomet Sports® Medicine brochure. (Jun. 15, 2011) 8 pages.
U.S. Appl. No. 10/984,624, Final Office Action mailed Jan. 5, 2009, 9 pgs.
U.S. Appl. No. 10/984,624, Non Final Office Action mailed Jun. 12, 2009, 9 pgs.
U.S. Appl. No. 10/984,624, Notice of Allowance mailed Jun. 12, 2009, 9 pgs.
U.S. Appl. No. 10/984,624, Response filed Apr. 1, 2009 to Final Office Action mailed Jan. 5, 2009, 16 pgs.
U.S. Appl. No. 10/984,624, Response filed Apr. 15, 2008 to Restriction Requirement mailed Mar. 24, 2008, 1 pg.
U.S. Appl. No. 10/984,624, Response filed Oct. 10, 2008 to Non Final Office Action mailed Jun. 12, 2009, 12 pgs.
U.S. Appl. No. 10/984,624, Restriction Requirement mailed Mar. 24, 2008, 5 pgs.
U.S. Appl. No. 11/294,694, Final Office Action mailed Sep. 1, 2010, 14 pgs.
U.S. Appl. No. 11/294,694, Non Final Office Action mailed Mar. 16, 2010, 19 pgs.
U.S. Appl. No. 11/294,694, Notice of Allowance mailed Nov. 17, 2010, 4 pgs.
U.S. Appl. No. 11/294,694, Preliminary Amendment filed Jan. 13, 2010, 9 pgs.
U.S. Appl. No. 11/294,694, Response filed Jun. 16, 2010 to Non Final Office Action mailed Mar. 16, 2010, 16 pgs.
U.S. Appl. No. 11/294,694, Response filed Nov. 1, 2010 to Final Office Action mailed Sep. 1, 2010, 10 pgs.
U.S. Appl. No. 11/294,694, Response filed Dec. 22, 2009 to Restriction Requirement mailed Nov. 25, 2009, 1 pg.
U.S. Appl. No. 11/294,694, Restriction Requirement mailed Nov. 25, 2009, 9 pgs.
U.S. Appl. No. 11/347,661, Examiner Interview Summary mailed Sep. 11, 2009, 2 pgs.
U.S. Appl. No. 11/347,661, Final Office Action mailed Mar. 3, 2009, 15 pgs.
U.S. Appl. No. 11/347,661, Non Final Office Action mailed Aug. 13, 2009, 19 pgs.
U.S. Appl. No. 11/347,661, Non Final Office Action mailed Aug. 21, 2008, 11 pgs.
U.S. Appl. No. 11/347,661, Notice of Allowance mailed Feb. 24, 2010, 8 pgs.
U.S. Appl. No. 11/347,661, Notice of Allowance mailed May 5, 2010, 8 pgs.
U.S. Appl. No. 11/347,661, Response filed May 29, 2008 to Restriction Requirement mailed Apr. 30, 2008, 1 pg.
U.S. Appl. No. 11/347,661, Response filed Jun. 3, 2009 to Final Office Action mailed Mar. 3, 2009, 19 pgs.
U.S. Appl. No. 11/347,661, Response filed Nov. 6, 2009 to Non Final Office Action mailed Aug. 13, 2009, 16 pgs.
U.S. Appl. No. 11/347,661, Response filed Nov. 19, 2008 to Non Final Office Action mailed Aug. 21, 2008, 12 pgs.
U.S. Appl. No. 11/347,661, Restriction Requirement mailed Apr. 30, 2008, 6 pgs.
U.S. Appl. No. 11/347,662, Examiner Interview Summary mailed Jun. 24, 2010, 3 pgs.
U.S. Appl. No. 11/347,662, Examiner interview Summary mailed Nov. 9, 2009, 3 pgs.
U.S. Appl. No. 11/347,662, Final Office Action mailed Sep. 16, 2009, 13 pgs.
U.S. Appl. No. 11/347,662, Final Office Action mailed Oct. 26, 2010, 10 pgs.
U.S. Appl. No. 11/347,662, Non Final Office Action mailed Mar. 9, 2009, 11 pgs.
U.S. Appl. No. 11/347,662, Non Final Office Action mailed May 21, 2010, 19 pgs.
U.S. Appl. No. 11/347,662, Non Final Office Action mailed Oct. 28, 2008, 13 pgs.
U.S. Appl. No. 11/347,662, Response filed Jan. 16, 2009 to Non Final Office Action mailed Oct. 28, 2008, 16 pgs.
U.S. Appl. No. 11/347,662, Response filed Feb. 12, 2010 to Final Office Action mailed Sep. 16, 2009, 21 pgs.
U.S. Appl. No. 11/347,662, Response filed Jun. 5, 2009 to Non Final Office Action mailed Mar. 9, 2009, 13 pgs.
U.S. Appl. No. 11/347,662, Response filed Aug. 20, 2010 to Non Final Office Action mailed May 21, 2010, 13 pgs.
U.S. Appl. No. 11/386,071, Advisory Action mailed Dec. 23, 2010, 3 pgs.
U.S. Appl. No. 11/386,071, Examiner Interview Summary mailed Jan. 31, 2011, 3 pgs.

(56) References Cited

OTHER PUBLICATIONS

U.S. Appl. No. 11/386,071, Examiner Interview Summary mailed Jul. 21, 2010, 3 pgs.
U.S. Appl. No. 11/386,071, Final Office Action mailed Oct. 27, 2010, 10 pgs.
U.S. Appl. No. 11/386,071, Non Final Office Action mailed May 12, 2010, 13 pgs.
U.S. Appl. No. 11/386,071, Notice of Allowance mailed Jun. 6, 2011, 6 pgs.
U.S. Appl. No. 11/386,071, Response filed Jan. 26, 2011 to Advisory Action mailed Dec. 23, 2010, 13 pgs.
U.S. Appl. No. 11/386,071, Response filed Aug. 12, 2010 to Non Final Office Action mailed May 12, 2010, 14 pgs.
U.S. Appl. No. 11/386,071, Response filed Dec. 15, 2010 to Final Office Action mailed Oct. 27, 2010, 14 pgs.
U.S. Appl. No. 11/408,282, Final Office Action mailed Dec. 15, 2008, 8 pgs.
U.S. Appl. No. 11/408,282, Non Final Office Action mailed May 23, 2008, 12 pgs.
U.S. Appl. No. 11/408,282, Response filed Aug. 21, 2008 to Non Final Office Action mailed May 23, 2008, 10 pgs.
U.S. Appl. No. 11/504,882, Examiner Interview Summary mailed Sep. 2, 2010, 3 pgs.
U.S. Appl. No. 11/504,882, Final Office Action mailed Dec. 21, 2010, 7 pgs.
U.S. Appl. No. 11/504,882, Non Final Office Action mailed Jun. 19, 2014, 11 pgs.
U.S. Appl. No. 11/504,882, Non Final Office Action mailed Jun. 23, 2010, 8 pgs.
U.S. Appl. No. 11/504,882, Non Final Office Action mailed Nov. 13, 2013, 13 pgs.
U.S. Appl. No. 11/504,882, Notice of Allowance mailed Dec. 1, 2014, 9 pgs.
U.S. Appl. No. 11/504,882, Response filed Feb. 10, 2014 to Non Final Office Action mailed Nov. 13, 2013, 11 pgs.
U.S. Appl. No. 11/504,882, Response filed Mar. 18, 2011 to Final Office Action mailed Dec. 21, 2010, 11 pgs.
U.S. Appl. No. 11/504,882, Response filed Sep. 17, 2014 to Non Final Office Action mailed Jun. 19, 2014, 14 pgs.
U.S. Appl. No. 11/504,882, Response filed Sep. 23, 2010 to Non Final Office Action mailed Jun. 23, 2010, 12 pgs.
U.S. Appl. No. 11/504,882, Supplemental Notice of Allowability mailed Mar. 12, 2015, 5 pgs.
U.S. Appl. No. 11/541,505, Non Final Office Action mailed May 19, 2009, 7 pgs.
U.S. Appl. No. 11/541,505, Notice of Allowance mailed Sep. 18, 2009, 8 pgs.
U.S. Appl. No. 11/541,505, Response filed Apr. 9, 2009 to Restriction Requirement mailed Mar. 9, 2009, 1 pg.
U.S. Appl. No. 11/541,505, Response filed Jun. 18, 2009 to Non Final Office Action mailed May 19, 2009, 5 pgs.
U.S. Appl. No. 11/541,505, Restriction Requirement mailed Mar. 9, 2009, 9 pgs.
U.S. Appl. No. 11/541,506, Notice of Allowance mailed Jun. 1, 2009, 10 pgs.
U.S. Appl. No. 11/541,506, Notice of Allowance mailed Jun. 29, 2009, 8 pgs.
U.S. Appl. No. 11/541,506, Response filed Apr. 9, 2009 to Restriction Requirement mailed Mar. 9, 2009, 1 pg.
U.S. Appl. No. 11/541,506, Restriction Requirement mailed Mar. 9, 2009, 6 pgs.
U.S. Appl. No. 11/739,768, Examiner Interview Summary mailed May 11, 2011, 3 pgs.
U.S. Appl. No. 11/739,768, Examiner Interview Summary mailed Oct. 4, 2011, 3 pgs.
U.S. Appl. No. 11/739,768, Final Office Action mailed Aug. 22, 2011, 14 pgs.
U.S. Appl. No. 11/739,768, Non Final Office Action mailed Mar. 4, 2011, 11 pgs.
U.S. Appl. No. 11/739,768, Notice of Allowance mailed Nov. 15, 2011, 5 pgs.
U.S. Appl. No. 11/739,768, Response filed Jun. 6, 2011 to Non Final Office Action mailed Mar. 4, 2011, 15 pgs.
U.S. Appl. No. 11/739,768, Response filed Oct. 26, 2011 to Final Office Action mailed Aug. 22, 2011, 14 pgs.
U.S. Appl. No. 11/740,035, Final Office Action mailed Aug. 7, 2008, 9 pgs.
U.S. Appl. No. 11/740,035, Non Final Office Action mailed Jan. 3, 2008, 9 pgs.
U.S. Appl. No. 11/740,035, Response filed Apr. 3, 2008 to Non Final Office Action mailed Jan. 3, 2008, 6 pgs.
U.S. Appl. No. 11/784,821, Corrected Notice of Allowance mailed Dec. 24, 2014, 4 pgs.
U.S. Appl. No. 11/784,821, Examiner Interview Summary mailed Jun. 26, 2014, 3 pgs.
U.S. Appl. No. 11/784,821, Examiner Interview Summary mailed Nov. 17, 2009, 3 pgs.
U.S. Appl. No. 11/784,821, Final Office Action mailed Mar. 10, 2010, 11 pgs.
U.S. Appl. No. 11/784,821, Non Final Office Action mailed Mar. 28, 2014, 14 pgs.
U.S. Appl. No. 11/784,821, Non Final Office Action mailed Sep. 4, 2009, 12 pgs.
U.S. Appl. No. 11/784,821, Notice of Allowance mailed Oct. 21, 2014, 10 pgs.
U.S. Appl. No. 11/784,821, Response filed Jun. 10, 2010 to Final Office Action mailed Mar. 10, 2010, 20 pgs.
U.S. Appl. No. 11/784,821, Response filed Jun. 15, 2009 to Restriction Requirement mailed May 13, 2009, 2 pgs.
U.S. Appl. No. 11/784,821, Response filed Jun. 26, 2014 to Non Final Office Action mailed Mar. 28, 2014, 16 pgs.
U.S. Appl. No. 11/784,821, Response filed Nov. 23, 2009 to Non Final Office Action mailed Sep. 4, 2009, 17 pgs.
U.S. Appl. No. 11/784,821, Restriction Requirement mailed May 13, 2009, 6 pgs.
U.S. Appl. No. 11/869,440, Examiner Interview Summary mailed Mar. 25, 2010, 3 pgs.
U.S. Appl. No. 11/869,440, Non Final Office Action mailed Mar. 1, 2010, 13 pgs.
U.S. Appl. No. 11/869,440, Notice of Allowance mailed Aug. 19, 2010, 10 pgs.
U.S. Appl. No. 11/869,440, Response filed Jun. 1, 2010 to Non Final Office Action mailed Mar. 1, 2010, 14 pgs.
U.S. Appl. No. 11/935,681, Examiner Interview Summary mailed Jul. 19, 2010, 3 pgs.
U.S. Appl. No. 11/935,681, Non Final Office Action mailed May 24, 2010, 12 pgs.
U.S. Appl. No. 11/935,681, Notice of Allowance mailed Nov. 8, 2010, 10 pgs.
U.S. Appl. No. 11/935,681, Response filed Apr. 19, 2010 to Restriction Requirement mailed Mar. 17, 2010, 4 pgs.
U.S. Appl. No. 11/935,681, Response filed Aug. 24, 2010 to Non Final Office Action mailed May 24, 2010, 13 pgs.
U.S. Appl. No. 11/935,681, Restriction Requirement mailed Mar. 17, 2010, 6 pgs.
U.S. Appl. No. 12/014,340, Examiner Interview Summary mailed Jun. 22, 2010, 3 pgs.
U.S. Appl. No. 12/014,340, Non Final Office Action mailed May 25, 2010, 12 pgs.
U.S. Appl. No. 12/014,340, Notice of Allowance mailed Nov. 8, 2010, 9 pgs.
U.S. Appl. No. 12/014,340, Preliminary Amendment filed May 21, 2010, 11 pgs.
U.S. Appl. No. 12/014,340, Response filed Apr. 26, 2010 to Restriction Requirement mailed Mar. 25, 2010, 2 pgs.
U.S. Appl. No. 12/014,340, Response filed Aug. 25, 2010 to Non Final Office Action mailed May 25, 2010, 16 pgs.
U.S. Appl. No. 12/014,340, Restriction Requirement mailed Mar. 25, 2010, 9 pgs.
U.S. Appl. No. 12/014,399, Examiner Interview Summary mailed Jun. 23, 2010, 3 pgs.

(56) References Cited

OTHER PUBLICATIONS

U.S. Appl. No. 12/014,399, Non Final Office Action mailed May 26, 2010, 13 pgs.
U.S. Appl. No. 12/014,399, Notice of Allowance mailed Nov. 12, 2010, 11 pgs.
U.S. Appl. No. 12/014,399, Preliminary Amendment filed May 25, 2010, 10 pgs.
U.S. Appl. No. 12/014,399, Response filed May 5, 2010 to Restriction Requirement mailed Apr. 6, 2010, 2 pgs.
U.S. Appl. No. 12/014,399, Response filed Aug. 25, 2010 to Non Final Office Action mailed May 26, 2010, 14 pgs.
U.S. Appl. No. 12/014,399, Restriction Requirement mailed Apr. 6, 2010, 9 pgs.
U.S. Appl. No. 12/029,861, Examiner Interview Summary mailed Jan. 27, 2012, 3 pgs.
U.S. Appl. No. 12/029,861, Final Office Action mailed Dec. 8, 2011, 11 pgs.
U.S. Appl. No. 12/029,861, Non Final Office Action mailed Jul. 26, 2011, 11 pgs.
U.S. Appl. No. 12/029,861, Notice of Allowance mailed Apr. 26, 2012, 5 pgs.
U.S. Appl. No. 12/029,861, Response filed Jan. 26, 2012 to Final Office Action mailed Dec. 8, 2011, 15 pgs.
U.S. Appl. No. 12/029,861, Response filed May 6, 2011 to Restriction Requirement mailed Apr. 7, 2011, 10 pgs.
U.S. Appl. No. 12/029,861, Response filed Jun. 23, 2011 to Restriction Requirement mailed May 24, 2011, 1 pgs.
U.S. Appl. No. 12/029,861, Response filed Oct. 14, 2011 to Non Final Office Action mailed Jul. 26, 2011, 11 pgs.
U.S. Appl. No. 12/029,861, Restriction Requirement mailed Apr. 7, 2011, 8 pgs.
U.S. Appl. No. 12/029,861, Restriction Requirement mailed May 24, 2011, 6 pgs.
U.S. Appl. No. 12/107,437, Examiner Interview Summary mailed May 10, 2010, 4 pgs.
U.S. Appl. No. 12/107,437, Non Final Office Action mailed Mar. 17, 2010, 9 pgs.
U.S. Appl. No. 12/107,437, Preliminary Amendment filed Feb. 23, 2010, 9 pgs.
U.S. Appl. No. 12/107,437, Response filed Jan. 29, 2010 to Restriction Requirement mailed Jan. 13, 2010, 1 pgs.
U.S. Appl. No. 12/107,437, Restriction Requirement mailed Jan. 13, 2010, 7 pgs.
U.S. Appl. No. 12/196,398, Examiner interview Summary mailed Nov. 8, 2010, 3 pgs.
U.S. Appl. No. 12/196,398, Notice of Allowance mailed Feb. 3, 2011, 12 pgs.
U.S. Appl. No. 12/196,398, Preliminary Amendment filed Nov. 10, 2008, 3 pgs.
U.S. Appl. No. 12/196,398, Preliminary Amendment filed Dec. 1, 2010, 12 pgs.
U.S. Appl. No. 12/196,398, Preliminary Amendment filed Dec. 9, 2008, 46 pgs.
U.S. Appl. No. 12/196,398, Response filed Oct. 29, 2010 to Restriction Requirement mailed Sep. 29, 2010, 2 pgs.
U.S. Appl. No. 12/196,398, Restriction Requirement mailed Sep. 29, 2010, 6 pgs.
U.S. Appl. No. 12/196,398, Supplemental Notice of Allowability mailed Mar. 9, 2011, 4 pgs.
U.S. Appl. No. 12/196,398, Supplemental Notice of Allowability mailed Apr. 15, 2011, 4 pgs.
U.S. Appl. No. 12/196,405, Examiner interview Summary mailed Jun. 20, 2011, 3 pgs.
U.S. Appl. No. 12/196,405, Non Final Office Action mailed Apr. 11, 2011, 13 pgs.
U.S. Appl. No. 12/196,405, Notice of Allowance mailed Oct. 26, 2011, 11 pgs.
U.S. Appl. No. 12/196,405, Preliminary Amendment filed Nov. 10, 2008, 3 pgs.
U.S. Appl. No. 12/196,405, Response filed Mar. 16, 2011 to Restriction Requirement mailed Feb. 14, 2011, 1 pgs.
U.S. Appl. No. 12/196,405, Response filed Jul. 12, 2011 to Non Final Office Action mailed Apr. 11, 2011, 19 pgs.
U.S. Appl. No. 12/196,405, Restriction Requirement mailed Feb. 14, 2011, 6 pgs.
U.S. Appl. No. 12/196,405, Supplemental Amendment filed Oct. 3, 2011, 12 pgs.
U.S. Appl. No. 12/196,407, Examiner Interview Summary mailed Jul. 14, 2011, 3 pgs.
U.S. Appl. No. 12/196,407, Non Final Office Action mailed May 4, 2011, 11 pgs.
U.S. Appl. No. 12/196,407, Notice of Allowance mailed Oct. 26, 2011, 10 pgs.
U.S. Appl. No. 12/196,407, Preliminary Amendment filed Nov. 8, 2008, 3 pgs.
U.S. Appl. No. 12/196,407, Response filed Apr. 20, 2011 to Restriction Requirement mailed Mar. 22, 2011, 12 pgs.
U.S. Appl. No. 12/196,407, Response filed Aug. 2, 2011 to Non Final Office Action mailed May 4, 2011, 27 pgs.
U.S. Appl. No. 12/196,407, Restriction Requirement mailed Mar. 22, 2011, 6 pgs.
U.S. Appl. No. 12/196,407, Supplemental Response to Non Final Office Action filed Oct. 3, 2011, 18 pgs.
U.S. Appl. No. 12/196,410, Examiner Interview Summary mailed Jul. 14, 2011, 3 pgs.
U.S. Appl. No. 12/196,410, Non Final Office Action mailed May 9, 2011, 9 pgs.
U.S. Appl. No. 12/196,410, Notice of Allowance mailed Oct. 13, 2011, 8 pgs.
U.S. Appl. No. 12/196,410, Response filed Apr. 20, 2011 to Restriction Requirement mailed Mar. 22, 2011, 13 pgs.
U.S. Appl. No. 12/196,410, Response filed Aug. 1, 2011 to Non Final Office Action mailed May 9, 2011, 23 pgs.
U.S. Appl. No. 12/196,410, Restriction Requirement mailed Mar. 22, 2011, 6 pgs.
U.S. Appl. No. 12/196,410, Supplemental Amendment filed Oct. 3, 2011, 15 pgs.
U.S. Appl. No. 12/398,548, Examiner Interview Summary mailed Jul. 12, 2011, 3 pgs.
U.S. Appl. No. 12/398,548, Non Final Office Action mailed Apr. 12, 2011, 7 pgs.
U.S. Appl. No. 12/398,548, Notice of Allowance mailed Oct. 18, 2011, 7 pgs.
U.S. Appl. No. 12/398,548, Response filed Jul. 12, 2011 to Non Final Office Action mailed Apr. 12, 2011, 15 pgs.
U.S. Appl. No. 12/398,548, Supplemental Preliminary Amendment filed Sep. 7, 2010, 11 pgs.
U.S. Appl. No. 12/419,491, Examiner Interview Summary mailed May 30, 2012, 3 pgs.
U.S. Appl. No. 12/419,491, Examiner Interview Summary mailed Nov. 29, 2011, 3 pgs.
U.S. Appl. No. 12/419,491, Final Office Action mailed Apr. 12, 2012, 12 pgs.
U.S. Appl. No. 12/419,491, Non Final Office Action mailed Sep. 22, 2011, 12 pgs.
U.S. Appl. No. 12/419,491, Notice of Allowance mailed Jul. 13, 2012, 10 pgs.
U.S. Appl. No. 12/419,491, Response filed May 30, 2012 to Final Office Action mailed Apr. 12, 2012, 12 pgs.
U.S. Appl. No. 12/419,491, Response filed Dec. 9, 2011 to Non Final Office Action.mailed Sep. 22, 2011, 17 pgs.
U.S. Appl. No. 12/474,802, Notice of Allowance mailed Aug. 31, 2011, 13 pgs.
U.S. Appl. No. 12/474,802, Notice of Allowance mailed Oct. 26, 2011, 4 pgs.
U.S. Appl. No. 12/474,802, Response filed Mar. 28, 2011 to Restriction Requirement mailed Feb. 24, 2011, 12 pgs.
U.S. Appl. No. 12/474,802, Restriction Requirement mailed Feb. 24, 2011, 6 pgs.
U.S. Appl. No. 12/489,168, Examiner Interview Summary mailed Feb. 21, 2012, 3 pgs.

(56) References Cited

OTHER PUBLICATIONS

U.S. Appl. No. 12/489,168, Non Final Office Action mailed Dec. 7, 2011, 10 pgs.
U.S. Appl. No. 12/489,168, Notice of Allowance mailed Apr. 26, 2012, 8 pgs.
U.S. Appl. No. 12/489,168, Notice of Allowance mailed Sep. 5, 2012, 8 pgs.
U.S. Appl. No. 12/489,168, Preliminary Amendment filed Oct. 22, 2009, 3 pgs.
U.S. Appl. No. 12/489,168, Response filed Feb. 27, 2012 to Non Final Office Action mailed Dec. 7, 2011, 15 pgs.
U.S. Appl. No. 12/489,168, Response filed Nov. 11, 2011 to Restriction Requirement mailed Oct. 20, 2011, 1 pg.
U.S. Appl. No. 12/489,168, Restriction Requirement mailed Oct. 20, 2011, 8 pgs.
U.S. Appl. No. 12/489,181, Examiner interview Summary mailed Feb. 13, 2012, 3 pgs.
U.S. Appl. No. 12/489,181, Non Final Office Action mailed Jan. 3, 2012, 9 pgs.
U.S. Appl. No. 12/489,181, Notice of Allowance mailed May 23, 2012, 9 pgs.
U.S. Appl. No. 12/489,181, Preliminary Amendment filed Mar. 31, 2011, 10 pgs.
U.S. Appl. No. 12/489,181, Preliminary Amendment filed Oct. 22, 2009, 3 pgs.
U.S. Appl. No. 12/489,181, Response filed Mar. 27, 2012 to Non Final Office Action mailed Jan. 3, 2012, 12 pgs.
U.S. Appl. No. 12/489,181, Response filed Dec. 5, 2011 to Restriction Requirement mailed Nov. 4, 2011, 1 pg.
U.S. Appl. No. 12/489,181, Restriction Requirement mailed Nov. 4, 2011, 7 pgs.
U.S. Appl. No. 12/570,854, Examiner Interview Summary mailed Apr. 16, 2012, 3 pgs.
U.S. Appl. No. 12/570,854, Non Final Office Action mailed Feb. 10, 2012, 8 pgs.
U.S. Appl. No. 12/570,854, Notice of Allowance mailed Jun. 29, 2012, 10 pgs.
U.S. Appl. No. 12/570,854, Notice of Allowance mailed Sep. 19, 2012, 6 pgs.
U.S. Appl. No. 12/570,854, Response filed May 10, 2012 to Non Final Office Action mailed Feb. 10, 2012, 27 pgs.
U.S. Appl. No. 12/570,854, Response filed Dec. 20, 2011 to Restriction Requirement mailed Dec. 14, 2011, 1 pg.
U.S. Appl. No. 12/570,854, Restriction Requirement mailed Dec. 14, 2011, 6 pgs.
U.S. Appl. No. 12/702,067, Non Final Office Action mailed Mar. 5, 2013, 8 pgs.
U.S. Appl. No. 12/702,067, Notice of Allowance mailed Oct. 7, 2013, 11 pgs.
U.S. Appl. No. 12/702,067, Preliminary Amendment filed Jan. 11, 2011, 13 pgs.
U.S. Appl. No. 12/702,067, Response filed Jun. 5, 2013 to Non Final Office Action mailed Mar. 5, 2013, 17 pgs.
U.S. Appl. No. 12/702,067, Response filed Oct. 2, 2012 to Restriction Requirement mailed Sep. 4, 2012, 1 pg.
U.S. Appl. No. 12/702,067, Restriction Requirement mailed Sep. 4, 2012, 9 pgs.
U.S. Appl. No. 12/719,337, Advisory Action mailed Sep. 30, 2014, 4 pgs.
U.S. Appl. No. 12/719,337, Examiner Interview Summary mailed Apr. 4, 2014, 4 pgs.
U.S. Appl. No. 12/719,337, Examiner Interview Summary mailed May 14, 2013, 3 pgs.
U.S. Appl. No. 12/719,337, Examiner Interview Summary mailed Sep. 18, 2014, 3 pgs.
U.S. Appl. No. 12/719,337, Final Office Action mailed Mar. 12, 2013, 8 pgs.
U.S. Appl. No. 12/719,337, Final Office Action mailed Jul. 18, 2014, 15 pgs.
U.S. Appl. No. 12/719,337, Non Final Office Action mailed Jan. 10, 2014, 14 pgs.
U.S. Appl. No. 12/719,337, Non Final Office Action mailed Sep. 5, 2012, 7 pgs.
U.S. Appl. No. 12/719,337, Notice of Allowance mailed Mar. 11, 2015, 10 pgs.
U.S. Appl. No. 12/719,337, Notice of Non-Compliant Amendment mailed May 2, 2014, 3 pgs.
U.S. Appl. No. 12/719,337, Response filed Apr. 10, 2014 to Non Final Office Action mailed Jan. 10, 2014, 16 pgs.
U.S. Appl. No. 12/719,337, Response filed May 25, 2012 to Restriction Requirement mailed Apr. 26, 2012, 9 pgs.
U.S. Appl. No. 12/719,337, Response filed Jun. 5, 2013 to Final Office Action mailed Mar. 12, 2013, 16 pgs.
U.S. Appl. No. 12/719,337, Response filed Jun. 25, 2014 to Notice of Non-Compliant Amendment mailed May 2, 2014, 10 pgs.
U.S. Appl. No. 12/719,337, Response filed Sep. 18, 2014 to Final Office Action mailed Jul. 18, 2014, 13 pgs.
U.S. Appl. No. 12/719,337, Response filed Nov. 28, 2012 to Non Final Office Action mailed Sep. 5, 2012, 14 pgs.
U.S. Appl. No. 12/719,337, Restriction Requirement mailed Apr. 26, 2012, 8 pgs.
U.S. Appl. No. 12/788,973, Advisory Action mailed Jan. 23, 2013, 3 pgs.
U.S. Appl. No. 12/788,973, Advisory Action mailed Dec. 27, 2012, 8 pgs.
U.S. Appl. No. 12/788,973, Final Office Action mailed Sep. 18, 2012, 16 pgs.
U.S. Appl. No. 12/788,973, Non Final Office Action mailed May 8, 2012, 12 pgs.
U.S. Appl. No. 12/788,973, Notice of Allowance mailed Mar. 21, 2013, 6 pgs.
U.S. Appl. No. 12/788,973, Response filed Jan. 16, 2013 to Advisory Action mailed Dec. 27, 2012, 9 pgs.
U.S. Appl. No. 12/788,973, Response filed Jul. 19, 2012 to Non Final Office Action mailed May 8, 2012, 21 pgs.
U.S. Appl. No. 12/788,973, Response filed Dec. 16, 2011 to Restriction Requirement mailed Dec. 6, 2011, 11 pgs.
U.S. Appl. No. 12/788,973, Response filed Dec. 17, 2012 to Final Office Action mailed Sep. 18, 2012, 15 pgs.
U.S. Appl. No. 12/788,973, Restriction Requirement mailed Dec. 6, 2011, 9 pgs.
U.S. Appl. No. 12/788,973, Supplemental Notice of Allowance mailed May 24, 2013, 2 pgs.
U.S. Appl. No. 12/788,978, Advisory Action mailed Dec. 24, 2013, 4 pgs.
U.S. Appl. No. 12/788,978, Applicant's Summary of Examiner Interview filed Dec. 12, 2013, 2 pgs.
U.S. Appl. No. 12/788,978, Corrected Notice of Allowance mailed Apr. 30, 2014, 2 pgs.
U.S. Appl. No. 12/788,978, Examiner Interview Summary mailed Jan. 28, 2014, 3 pgs.
U.S. Appl. No. 12/788,978, Examiner Interview Summary mailed Mar. 22, 2013, 3 pgs.
U.S. Appl. No. 12/788,978, Examiner Interview Summary mailed Sep. 11, 2012, 3 pgs.
U.S. Appl. No. 12/788,978, Examiner Interview Summary mailed Oct. 29, 2013, 4 pgs.
U.S. Appl. No. 12/788,978, Examiner Interview Summary mailed Dec. 16, 2013, 3 pgs.
U.S. Appl. No. 12/788,978, Examiner Interview Summary mailed Dec. 27, 2012, 3 pgs.
U.S. Appl. No. 12/788,978, Final Office Action mailed Aug. 20, 2013, 17 pgs.
U.S. Appl. No. 12/788,978, Final Office Action mailed Nov. 2, 2012, 14 pgs.
U.S. Appl. No. 12/788,978, Non Final Office Action mailed Jan. 11, 2013, 16 pgs.
U.S. Appl. No. 12/788,978, Non Final Office Action mailed Jul. 13, 2012, 17 pgs.
U.S. Appl. No. 12/788,978, Notice of Allowance mailed Jan. 24, 2014, 9 pgs.

(56) References Cited

OTHER PUBLICATIONS

U.S. Appl. No. 12/788,978, Notice of Non-Compliant Amendment mailed Jun. 6, 2013, 3 pgs.
U.S. Appl. No. 12/788,978, Response filed Jan. 2, 2013 to Final Office Action mailed Nov. 2, 2012, 13 pgs.
U.S. Appl. No. 12/788,978, Response filed Jan. 20, 2014 to Advisory Action mailed Dec. 24, 2013, 4 pgs.
U.S. Appl. No. 12/788,978, Response filed Apr. 8, 2013 to Non Final Office Action mailed Jan. 11, 2013, 16 pgs.
U.S. Appl. No. 12/788,978, Response filed May 21, 2012 to Restriction Requirement mailed Apr. 20, 2012, 12 pgs.
U.S. Appl. No. 12/788,978, Response filed Jul. 3, 2013 to Notice of Non-Compliant Amendment mailed Jun. 6, 2013, 17 pgs.
U.S. Appl. No. 12/788,978, Response filed Oct. 5, 2012 to Non Final Office Action mailed Jul. 13, 2012, 20 pgs.
U.S. Appl. No. 12/788,978, Response filed Nov. 20, 2013 to Final Office Action mailed Aug. 20, 2013, 15 pgs.
U.S. Appl. No. 12/788,978, Restriction Requirement mailed Apr. 20, 2012, 8 pgs.
U.S. Appl. No. 12/828,977, Examiner Interview Summary mailed Jul. 9, 2012, 3 pgs.
U.S. Appl. No. 12/828,977, Non Final Office Action mailed May 3, 2012, 9 pgs.
U.S. Appl. No. 12/828,977, Notice of Allowance mailed Sep. 5, 2012, 9 pgs.
U.S. Appl. No. 12/828,977, Preliminary Amendment filed Jul. 19, 2011, 10 pgs.
U.S. Appl. No. 12/828,977, Response filed Mar. 14, 2012 to Restriction Requirement mailed Feb. 13, 2012, 9 pgs.
U.S. Appl. No. 12/828,977, Response filed Jul. 25, 2012 to Non Final Office Action mailed May 3, 2012, 11 pgs.
U.S. Appl. No. 12/828,977, Restriction Requirement mailed Feb. 13, 2012, 7 pgs.
U.S. Appl. No. 12/915,962, Examiner Interview Summary mailed Jul. 25, 2012, 3 pgs.
U.S. Appl. No. 12/915,962, Non Final Office Action mailed May 7, 2012, 11 pgs.
U.S. Appl. No. 12/915,962, Non Final Office Action mailed Oct. 15, 2012, 9 pgs.
U.S. Appl. No. 12/915,962, Notice of Allowance mailed Jun. 10, 2013, 12 pgs.
U.S. Appl. No. 12/915,962, Response filed Jan. 10, 2013 to Non Final Office Action mailed Oct. 15, 2012, 21 pgs.
U.S. Appl. No. 12/915,962, Response filed Mar. 16, 2012 to Restriction Requirement mailed Feb. 15, 2012, 15 pgs.
U.S. Appl. No. 12/915,962, Response filed Aug. 7, 2012 to Non Final Office Action mailed May 7, 2012, 26 pgs.
U.S. Appl. No. 12/915,962, Restriction Requirement mailed Feb. 15, 2012, 8 pgs.
U.S. Appl. No. 12/976,328, Examiner Interview Summary mailed Feb. 13, 2012, 3 pgs.
U.S. Appl. No. 12/976,328, Non Final Office Action mailed Dec. 15, 2011, 13 pgs.
U.S. Appl. No. 12/976,328, Notice of Allowance mailed Apr. 30, 2012, 9 pgs.
U.S. Appl. No. 12/976,328, Response filed Mar. 2, 2012 to Non Final Office Action mailed Dec. 15, 2011, 15 pgs.
U.S. Appl. No. 13/045,689, Examiner Interview Summary mailed May 14, 2012, 3 pgs.
U.S. Appl. No. 13/045,689, Non Final Office Action mailed Mar. 20, 2012, 11 pgs.
U.S. Appl. No. 13/045,689, Notice of Allowance mailed Aug. 10, 2012, 10 pgs.
U.S. Appl. No. 13/045,689, Notice of Allowance mailed Sep. 24, 2012, 7 pgs.
U.S. Appl. No. 13/045,689, Response filed Jan. 30, 2012 to Restriction Requirement mailed Dec. 29, 2011, 13 pgs.
U.S. Appl. No. 13/045,689, Response filed Jun. 8, 2012 to Non Final Office Action mailed Mar. 20, 2012, 15 pgs.
U.S. Appl. No. 13/045,689, Restriction Requirement mailed Dec. 29, 2011, 6 pgs.
U.S. Appl. No. 13/045,691, Examiner Interview Summary mailed May 14, 2012, 3 pgs.
U.S. Appl. No. 13/045,691, Non Final Office Action mailed Mar. 20, 2012, 12 pgs.
U.S. Appl. No. 13/045,691, Notice of Allowance mailed Jun. 19, 2012, 10 pgs.
U.S. Appl. No. 13/045,691, Response filed Feb. 9, 2012 to Restriction Requirement mailed Jan. 9, 2012, 1 pg.
U.S. Appl. No. 13/045,691, Response filed Jun. 8, 2012 to Non Final Office Action mailed Mar. 20, 2012, 17 pgs.
U.S. Appl. No. 13/045,691, Restriction Requirement mailed Jan. 9, 2012, 6 pgs.
U.S. Appl. No. 13/071,563, Final Office Action mailed May 23, 2014, 13 pgs.
U.S. Appl. No. 13/071,563, Non Final Office Action mailed Oct. 23, 2013, 18 pgs.
U.S. Appl. No. 13/071,563, Notice of Allowance mailed Aug. 15, 2014, 7 pgs.
U.S. Appl. No. 13/071,563, Preliminary Amendment filed May 1, 2012, 8 pgs.
U.S. Appl. No. 13/071,563, Preliminary Amendment filed Dec. 6, 2011, 7 pgs.
U.S. Appl. No. 13/071,563, Response filed Jan. 21, 2014 to Non Final Office Action mailed Oct. 23, 2013, 13 pgs.
U.S. Appl. No. 13/071,563, Response filed Jul. 23, 2014 to Final Office Action mailed May 23, 2014, 14 pgs.
U.S. Appl. No. 13/071,563, Response filed Sep. 19, 2013 to Restriction Requirement mailed Aug. 19, 2013, 11 pgs.
U.S. Appl. No. 13/071,563, Restriction Requirement mailed Aug. 19, 2013, 7 pgs.
U.S. Appl. No. 13/098,897, Examiner Interview Summary mailed Nov. 27, 2012, 3 pgs.
U.S. Appl. No. 13/098,897, Non Final Office Action mailed Sep. 21, 2012, 9 pgs.
U.S. Appl. No. 13/098,897, Notice of Allowance mailed Jun. 11, 2013, 13 pgs.
U.S. Appl. No. 13/098,897, Response filed Aug. 30, 2012 to Restriction Requirement mailed Jul. 30, 2012, 16 pgs.
U.S. Appl. No. 13/098,897, Response filed Dec. 18, 2012 to Non Final Office Action mailed Sep. 21, 2012, 21 pgs.
U.S. Appl. No. 13/098,897, Restriction Requirement mailed Jul. 30, 2012, 8 pgs.
U.S. Appl. No. 13/098,927, Advisory Action mailed Aug. 8, 2013, 3 pgs.
U.S. Appl. No. 13/098,927, Applicant's Summary of Examiner Interview filed Sep. 23, 2013, 12 pgs.
U.S. Appl. No. 13/098,927, Examiner Interview Summary mailed Jun. 28, 2013, 3 pgs.
U.S. Appl. No. 13/098,927, Examiner Interview Summary mailed Sep. 20, 2013, 3 pgs.
U.S. Appl. No. 13/098,927, Final Office Action mailed May 22, 2013, 10 pgs.
U.S. Appl. No. 13/098,927, Non Final Office Action mailed Sep. 24, 2012, 12 pgs.
U.S. Appl. No. 13/098,927, Notice of Allowance mailed Jan. 8, 2014, 5 pgs.
U.S. Appl. No. 13/098,927, Notice of Allowance mailed Sep. 26, 2013, 14 pgs.
U.S. Appl. No. 13/098,927, Response filed Jul. 22, 2015 to Final Office Action mailed May 22, 2013, 17 pgs.
U.S. Appl. No. 13/098,927, Response filed Aug. 27, 2012 to Restriction Requirement mailed Jul. 25, 2012, 14 pgs.
U.S. Appl. No. 13/098,927, Response filed Dec. 21, 2012 to Non Final Office Action mailed Sep. 24, 2012, 21 pgs.
U.S. Appl. No. 13/098,927, Restriction Requirement mailed Jul. 25, 2012, 8 pgs.
U.S. Appl. No. 13/102,182, Notice of Allowance mailed Mar. 22, 2012, 10 pgs.
U.S. Appl. No. 13/109,667, Advisory Action mailed Feb. 4, 2014, 4 pgs.

(56) References Cited

OTHER PUBLICATIONS

U.S. Appl. No. 13/109,667, Examiner Interview Summary mailed Dec. 20, 2013, 3 pgs.
U.S. Appl. No. 13/109,667, Final Office Action mailed Oct. 11, 2013, 19 pgs.
U.S. Appl. No. 13/109,667, Non Final Office Action mailed May 21, 2013, 21 pgs.
U.S. Appl. No. 13/109,667, Notice of Allowance mailed Feb. 18, 2014, 10 pgs.
U.S. Appl. No. 13/109,667, Response filed Jan. 13, 2014 to Final Office Action mailed Oct. 11, 2013, 20 pgs.
U.S. Appl. No. 13/109,667, Response filed May 2, 2013 to Restriction Requirement mailed Apr. 2, 2013, 1 pg.
U.S. Appl. No. 13/109,667, Response filed Aug. 21, 2013 to Non Final Office Action mailed May 21, 2013, 27 pgs.
U.S. Appl. No. 13/109,667, Restriction Requirement mailed Apr. 2, 2013, 8 pgs.
U.S. Appl. No. 13/109,667, Supplemental Notice of Allowabilfty mailed Jun. 12, 2014, 3 pgs.
U.S. Appl. No. 13/109,667, Supplemental Notice of Allowance mailed May 28, 2014, 2 pgs.
U.S. Appl. No. 13/109,667, Supplemental Preliminary Amendment filed Feb. 4, 2014, 16 pgs.
U.S. Appl. No. 13/111,564, Corrected Notice of Allowance mailed Oct. 9, 2013, 2 pgs.
U.S. Appl. No. 13/111,564, Examiner Interview Summary mailed Jun. 18, 2013, 3 pgs.
U.S. Appl. No. 13/111,564, Non Final Office Action mailed Mar. 18, 2013, 8 pgs.
U.S. Appl. No. 13/111,564, Notice of Allowance mailed Jun. 28, 2013, 12 pgs.
U.S. Appl. No. 13/111,564, Response filed Feb. 4, 2013 to Restriction Requirement mailed Jan. 3, 2013, 20 pgs.
U.S. Appl. No. 13/111,564, Response filed Jun. 18, 2013 to Non Final Office Action mailed Mar. 18, 2013, 25 pgs.
U.S. Appl. No. 13/111,564, Restriction Requirement mailed Jan. 3, 2013, 5 pgs.
U.s. Appl. No. 13/181,729, Examiner Interview Summary mailed May 9, 2013, 3 pgs.
U.S. Appl. No. 13/181,729, Final Office Action mailed Mar. 13, 2013, 14 pgs.
U.S. Appl. No. 13/181,729, Non Final Office Action mailed Oct. 2, 2012, 7 pgs.
U.S. Appl. No. 13/181,729, Notice of Allowance mailed May 23, 2013, 9 pgs.
U.S. Appl. No. 13/181,729, Response filed May 13, 2013 to Final Office Action mailed Mar. 13, 2013, 13 pgs.
U.S. Appl. No. 13/181,729, Response filed Dec. 20, 2012 to Non Final Office Action mailed Oct. 2, 2012, 15 pgs.
U.S. Appl. No. 13/269,097, Final Office Action mailed Aug. 8, 2013, 7 pgs.
U.S. Appl. No. 13/269,097, Non Final Office Action mailed Feb. 12, 2013, 10 pgs.
U.S. Appl. No. 13/269,097, Notice of Allowance mailed Feb. 3, 2014, 5 pgs.
U.S. Appl. No. 13/269,097, Notice of Allowance mailed Oct. 21, 2013, 9 pgs.
U.S. Appl. No. 13/269,097, Response filed May 13, 2013 to Non Final Office Action mailed Feb. 12, 2013, 17 pgs.
U.S. Appl. No. 13/269,097, Response filed Oct. 8, 2013 to Final Office Action mailed Aug. 8, 2013, 12 pgs.
U.S. Appl. No. 13/269,097, Response filed Nov. 13, 2012 to Restriction Requirement mailed Oct. 17, 2012, 1 pg.
U.S. Appl. No. 13/269,097, Restriction Requirement mailed Oct. 17, 2012, 8 pgs.
U.S. Appl. No. 13/278,341, Notice of Allowance mailed Jun. 18, 2013, 10 pgs.
U.S. Appl. No. 13/278,341, Response filed Mar. 8, 2013 to Restriction Requirement mailed Feb. 11, 2013, 1 pg.
U.S. Appl. No. 13/278,341, Restriction Requirement mailed Feb. 11, 2013, 6 pgs.
U.S. Appl. No. 13/281,009, Non Final Office Action mailed Jun. 2, 2015, 9 pgs.
U.S. Appl. No. 13/281,009, Notice of Allowance mailed Feb. 24, 2016, 9 pgs.
U.S. Appl. No. 13/281,009, Notice of Allowance mailed Oct. 29, 2015, 8 pgs.
U.S. Appl. No. 13/281,009, Response filed Sep. 2, 2015 to Non Final Office Action mailed Jun. 2, 2015, 13 pgs.
U.S. Appl. No. 13/281,009, Restriction Requirement mailed Feb. 11, 2015, 6 pgs.
U.S. Appl. No. 13/288,459, Examiner Interview Summary mailed Feb. 6, 2015, 3 pgs.
U.S. Appl. No. 13/288,459, Non Final Office Action mailed Jun. 24, 2015, 10 pgs.
U.S. Appl. No. 13/288,459, Non Final Office Action mailed Nov. 4, 2014, 15 pgs.
U.S. Appl. No. 13/288,459, Notice of Allowance mailed Jan. 11, 2016, 13 pgs.
U.S. Appl. No. 13/288,459, Response filed Mar. 3, 2015 to Non Final Office Action mailed Nov. 4, 2014, 16 pgs.
U.S. Appl. No. 13/288,459, Response filed Oct. 13, 2014 to Restriction Requirement mailed Aug. 11, 2014, 15 pgs.
U.S. Appl. No. 13/288,459, Response filed Oct. 23, 2015 to Non Final Office Action mailed Jun. 24, 2015, 14 pgs.
U.S. Appl. No. 13/288,459, Restriction Requirement mailed Aug. 11, 2014, 9 pgs.
U.S. Appl. No. 13/288,463, Examiner Interview Summary mailed Jun. 3, 2014, 3 pgs.
U.S. Appl. No. 13/288,463, Non Final Office Action mailed Feb. 24, 2014, 13 pgs.
U.S. Appl. No. 13/288,463, Notice of Allowance mailed Aug. 27, 2014, 9 pgs.
U.S. Appl. No. 13/288,463, Response filed May 27, 2014 to Non Final Office Action mailed Feb. 24, 2014, 15 pgs.
U.S. Appl. No. 13/288,463, Supplemental Notice of Allowability mailed Dec. 8, 2014, 5 pgs.
U.S. Appl. No. 13/288,463, Supplemental Notice of Allowability mailed Dec. 19, 2014, 5 pgs.
U.S. Appl. No. 13/293,825, Notice of Allowability mailed Jun. 22, 2015, 7 pgs.
U.S. Appl. No. 13/293,825, Notice of Allowance mailed May 19, 2015, 9 pgs.
U.S. Appl. No. 13/293,825, Response filed Apr. 15, 2015 to Restriction Requirement mailed Feb. 12, 2015, 17 pgs.
U.S. Appl. No. 13/293,825, Restriction Requirement mailed Feb. 12, 2015, 9 pgs.
U.S. Appl. No. 13/295,126, Non Final Office Action mailed May 19, 2015, 9 pgs.
U.S. Appl. No. 13/295,126, Notice of Allowance mailed Oct. 22, 2015, 9 pgs.
U.S. Appl. No. 13/295,126, Response filed Apr. 13, 2015 to Restriction Requirement mailed Feb. 12, 2015, 1 pgs.
U.S. Appl. No. 13/295,126, Response filed Aug. 17, 2015 to Non Final Office Action mailed May 19, 2015, 21 pgs.
U.S. Appl. No. 13/295,126, Restriction Requirement mailed Feb. 12, 2015, 9 pgs.
U.S. Appl. No. 13/311,936, Examiner Interview Summary mailed Feb. 12, 2015, 2 pgs.
U.S. Appl. No. 13/311,936, Non Final Office Action mailed Feb. 9, 2015, 13 pgs.
U.S. Appl. No. 13/311,936, Non Final Office Action mailed Oct. 19, 2015, 8 pgs.
U.S. Appl. No. 13/311,936, Response filed Jan. 18, 2016 to Non Final Office Action mailed Oct. 19, 2015, 8 pgs.
U.S. Appl. No. 13/311,936, Response filed Jun. 9, 2015 to Non Final Office Action mailed Feb. 9, 2015, 12 pgs.
U.S. Appl. No. 13/311,936, Response filed Oct. 3, 2014 to Restriction Requirement mailed Aug. 5, 2014, 10 pgs.
U.S. Appl. No. 13/311,936, Restriction Requirement mailed Aug. 5, 2014, 7 pgs.

(56) References Cited

OTHER PUBLICATIONS

U.S. Appl. No. 13/350,985, Final Office Action mailed Apr. 16, 2015, 8 pgs.
U.S. Appl. No. 13/350,985, Non Final Office Action mailed Dec. 15, 2014, 8 pgs.
U.S. Appl. No. 13/350,985, Notice of Allowance mailed Jul. 27, 2015, 5 pgs.
U.S. Appl. No. 13/350,985, Response filed Mar. 13, 2015 to Non Final Office Action mailed Dec. 15, 2014, 10 pgs.
U.S. Appl. No. 13/350,985, Response filed Jul. 9, 2015 to Final Office Action mailed Apr. 16, 2015, 8 pgs.
U.S. Appl. No. 13/350,985, Response filed Dec. 2, 2014 to Restriction Requirement mailed Oct. 2, 2014, 9 pgs.
U.S. Appl. No. 13/350,985, Restriction Requirement mailed Oct. 2, 2014, 6 pgs.
U.S. Appl. No. 13/399,125, Corrected Notice of Allowance mailed Aug. 28, 2014, 2 pgs.
U.S. Appl. No. 13/399,125, Examiner Interview Summary mailed May 17, 2013, 3 pgs.
U.S. Appl. No. 13/399,125, Final Office Action mailed Mar. 20, 2013, 12 pgs.
U.S. Appl. No. 13/399,125, Non Final Office Action mailed Oct. 24, 2012, 12 pgs.
U.S. Appl. No. 13/399,125, Notice of Allowance mailed May 16, 2014, 8 pgs.
U.S. Appl. No. 13/399,125, Response filed Jan. 10, 2013 to Non Final Office Action mailed Oct. 24, 2012, 15 pgs.
U.S. Appl. No. 13/399,125, Response filed May 20, 2013 to Final Office Action mailed Mar. 20, 2013, 14 pgs.
U.S. Appl. No. 13/412,105, Advisory Action mailed Feb. 24, 2014, 3 pgs.
U.S. Appl. No. 13/412,105, Examiner Interview Summary mailed Feb. 6, 2014, 3 pgs.
U.S. Appl. No. 13/412,105, Examiner Interview Summary mailed Oct. 11, 2013, 3 pgs.
U.S. Appl. No. 13/412,105, Final Office Action mailed Dec. 13, 2013, 9 pgs.
U.S. Appl. No. 13/412,105, Non Final Office Action mailed Jul. 15, 2013, 10 pgs.
U.S. Appl. No. 13/412,105, Notice of Allowance mailed Aug. 18, 2014, 9 pgs.
U.S. Appl. No. 13/412,105, Response filed Feb. 10, 2014 to Final Office Action mailed Dec. 13, 2013, 14 pgs.
U.S. Appl. No. 13/412,105, Response filed Mar. 13, 2014 to Advisory Action mailed Feb. 24, 2014, 19 pgs.
U.S. Appl. No. 13/412,105, Response filed May 6, 2013 to Restriction Requirement mailed Apr. 5, 2013, 9 pgs.
U.S. Appl. No. 13/412,105, Response filed Oct. 14, 2013 to Non Final Office Action mailed Jul. 15, 2013, 13 pgs.
U.S. Appl. No. 13/412,105, Restriction Requirement mailed Apr. 5, 2013, 9 pgs.
U.S. Appl. No. 13/412,116, Corrected Notice of Allowance mailed Jun. 2, 2014, 2 pgs.
U.S. Appl. No. 13/412,116, Examiner Interview Summary mailed Dec. 13, 2013, 3 pgs.
U.S. Appl. No. 13/412,116, Non Final Office Action mailed Sep. 11, 2013, 9 pgs.
U.S. Appl. No. 13/412,116, Notice of Allowance mailed Feb. 19, 2014, 9 pgs.
U.S. Appl. No. 13/412,116, Response filed Jul. 3, 2013 to Restriction Requirement mailed Jun. 19, 2013, 1 pg.
U.S. Appl. No. 13/412,116, Response filed Dec. 11, 2013 to Non Final Office Action mailed Sep. 11, 2013, 11 pgs.
U.S. Appl. No. 13/412,116, Restriction Requirement mailed Jun. 19, 2013, 9 pgs.
U.S. Appl. No. 13/412,127, Examiner Interview Summary mailed Nov. 5, 2013, 3 pgs.
U.S. Appl. No. 13/412,127, Non Final Office Action mailed Aug. 7, 2013, 15 pgs.
U.S. Appl. No. 13/412,127, Notice of Allowance mailed Dec. 24, 2013, 10 pgs.
U.S. Appl. No. 13/412,127, Response filed May 23, 2013 to Restriction Requirement mailed Apr. 24, 2013, 2 pgs.
U.S. Appl. No. 13/412,127, Response filed Nov. 5, 2013 to Non Final Office Action mailed Aug. 7, 2013, 16 pgs.
U.S. Appl. No. 13/412,127, Restriction Requirement mailed Apr. 24, 2013, 10 pgs.
U.S. Appl. No. 13/587,374, Final Office Action mailed Nov. 6, 2013, 9 pgs.
U.S. Appl. No. 13/587,374, Non Final Office Action mailed Jul. 17, 2013, 8 pgs.
U.S. Appl. No. 13/587,374, Notice of Allowance mailed Feb. 28, 2014, 5 pgs.
U.S. Appl. No. 13/587,374, Preliminary Amendment filed Jun. 21, 2013, 9 pgs.
U.S. Appl. No. 13/587,374, Response filed Jan. 24, 2014 to Final Office Action mailed Nov. 6, 2013, 15 pgs.
U.S. Appl. No. 13/587,374, Response filed Oct. 14, 2013 to Non Final Office Action mailed Jul. 17, 2013, 14 pgs.
U.S. Appl. No. 13/645,964, Advisory Action mailed Feb. 4, 2016, 2 pgs.
U.S. Appl. No. 13/645,964, Final Office Action mailed Oct. 6, 2015, 17 pgs.
U.S. Appl. No. 13/645,964, Non Final Office Action mailed Mar. 17, 2015, 15 pgs.
U.S. Appl. No. 13/645,964, Response filed Jul. 17, 2015 to Non Final Office Action mailed Mar. 17, 2015, 17 pgs.
U.S. Appl. No. 13/645,964, Response filed Dec. 4, 2015 to Final Office Action mailed Oct. 6, 2015, 14 pgs.
U.S. Appl. No. 13/656,821, Notice of Allowance mailed Jun. 18, 2015, 11 pgs.
U.S. Appl. No. 13/656,821, Response filed May 11, 2015 to Restriction Requirement mailed Mar. 10, 2015, 1 pg.
U.S. Appl. No. 13/656,821, Restriction Requirement mailed Mar. 10, 2015, 6 pgs.
U.S. Appl. No. 13/720,648, Final Office Action mailed Nov. 16, 2015, 7 pgs.
U.S. Appl. No. 13/720,648, Non Final Office Action mailed Jun. 10, 2015, 11 pgs.
U.S. Appl. No. 13/720,648, Notice of Allowance mailed Feb. 5, 2016, 11 pgs.
U.S. Appl. No. 13/720,648, Response filed Jan. 13, 2016 to Final Office Action mailed Nov. 16, 2015, 9 pgs.
U.S. Appl. No. 13/720,648, Response filed May 11, 2015 to Restriction Requirement mailed Mar. 10, 2015, 8 pgs.
U.S. Appl. No. 13/720,648, Response filed Oct. 9, 2015 to Non Final Office Action mailed Jun. 10, 2015, 12 pgs.
U.S. Appl. No. 13/720,648, Restriction Requirement mailed Mar. 10, 2015, 8 pgs.
U.S. Appl. No. 13/721,970, Notice of Allowance mailed Aug. 12, 2013, 13 pgs.
U.S. Appl. No. 13/721,970, Preliminary Amendment filed Mar. 15, 2013, 13 pgs.
U.S. Appl. No. 13/721,970, Response filed May 8, 2013 to Restriction Requirement mailed Apr. 11, 2013, 1 pg.
U.S. Appl. No. 13/721,970, Restriction Requirement mailed Apr. 11, 2013, 6 pgs.
U.S. Appl. No. 13/751,846, Final Office Action mailed Nov. 17, 2015, 9 pgs.
U.S. Appl. No. 13/751,846, Non Final Office Action mailed Jun. 15, 2015, 10 pgs.
U.S. Appl. No. 13/751,846, Response filed Feb. 5, 2016 to Final Office Action mailed Nov. 17, 2015, 14 pgs.
U.S. Appl. No. 13/751,846, Response filed May 11, 2015 to Restriction Requirement mailed Mar. 10, 2015, 15 pgs.
U.S. Appl. No. 13/751,846, Response filed Oct. 9, 2015 to Non Final Office Action mailed Jun. 15, 2015, 20 pgs.
U.S. Appl. No. 13/751,846, Restriction Requirement mailed Mar. 10, 2015, 7 pgs.
U.S. Appl. No. 13/757,003, Non Final Office Action mailed Jun. 25, 2015, 8 pgs.

(56) References Cited

OTHER PUBLICATIONS

U.S. Appl. No. 13/757,003, Notice of Allowance mailed Feb. 8, 2016, 10 pgs.
U.S. Appl. No. 13/757,003, Response filed May 12, 2015 to Restriction Requirement mailed Mar. 12, 2015, 9 pgs.
U.S. Appl. No. 13/757,003, Response filed Oct. 26, 2015 to Non Final Office Action mailed Jul. 25, 2015, 8 pgs.
U.S. Appl. No. 13/757,003, Restriction Requirement mailed Mar. 12, 2015, 6 pgs.
U.S. Appl. No. 13/757,019, Non Final Office Action mailed Jun. 25, 2015, 11 pgs.
U.S. Appl. No. 13/757,019, Notice of Allowance mailed Dec. 10, 2015, 10 pgs.
U.S. Appl. No. 13/757,019, Response filed May 11, 2015 to Restriction Requirement mailed Mar. 11, 2015, 9 pgs.
U.S. Appl. No. 13/757,019, Response filed Oct. 26, 2015 to Non Final Office Action mailed Jun. 25, 2015, 9 pgs.
U.S. Appl. No. 13/757,019, Restriction Requirement mailed Mar. 11, 2015, 10 pgs.
U.S. Appl. No. 13/767,401, Non Final Office Action mailed Aug. 26, 2015, 9 pgs.
U.S. Appl. No. 13/767,401, Notice of Allowance mailed Dec. 30, 2015, 9 pgs.
U.S. Appl. No. 13/767,401, Response filed May 18, 2015 to Restriction Requirement mailed Mar. 17, 2015, 15 pgs.
U.S. Appl. No. 13/767,401, Response filed Nov. 6, 2015 to Non Final Office Action mailed Aug. 26, 2015, 12 pgs.
U.S. Appl. No. 13/767,401, Restriction Requirement mailed Mar. 17, 2015, 8 pgs.
U.S. Appl. No. 13/790,982, Examiner Interview Summary mailed Jun. 9, 2015, 3 pgs.
U.S. Appl. No. 13/790,982, Non Final Office Action mailed Sep. 16, 2015, 11 pgs.
U.S. Appl. No. 13/790,982, Notice of Allowance mailed Feb. 24, 2016, 10 pgs.
U.S. Appl. No. 13/790,982, Response filed Jun. 2, 2015 to Restriction Requirement mailed Apr. 2, 2015, 11 pgs.
U.S. Appl. No. 13/790,982, Response filed Dec. 16, 2015 to Non Final Office Action mailed Sep. 16, 2015, 10 pgs.
U.S. Appl. No. 13/790,982, Restriction Requirement mailed Apr. 2, 2015, 10 pgs.
U.S. Appl. No. 13/790,997, Examiner Interview Summary mailed Jun. 8, 2015, 3 pgs.
U.S. Appl. No. 13/790,997, Non Final Office Action mailed Sep. 21, 2015, 8 pgs.
U.S. Appl. No. 13/790,997, Notice of Allowance mailed Mar. 2, 2016, 9 pgs.
U.S. Appl. No. 13/790,997, Response filed Jun. 2, 2015 to Restriction Requirement mailed Apr. 2, 2015, 12 pgs.
U.S. Appl. No. 13/790,997, Response filed Dec. 18, 2015 to Non Final Office Action mailed Sep. 21, 2015, 9 pgs.
U.S. Appl. No. 13/790,997, Restriction Requirement mailed Apr. 2, 2015, 8 pgs.
U.S. Appl. No. 13/833,567, Final Office Action mailed Mar 9, 2016, 9 pgs.
U.S. Appl. No. 13/833,567, Non Final Office Action mailed Oct. 23, 2015, 10 pgs.
U.S. Appl. No. 13/833,567, Response filed Jan. 22, 2016 to Non Final Office Action mailed Oct. 23, 2015, 11 pgs.
U.S. Appl. No. 13/833,567, Response filed Jun. 25, 2015 to Restriction Requirement mailed Apr. 3, 2015, 10 pgs.
U.S. Appl. No. 13/833,567, Restriction Requirement mailed Apr. 3, 2015, 6 pgs.
U.S. Appl. No. 13/838,755, Final Office Action mailed Feb. 22, 2016, 9 pgs.
U.S. Appl. No. 13/838,755, Non Final Office Action mailed Sep. 17, 2015, 11 pgs.
U.S. Appl. No. 13/838,755, Response filed Jun. 8, 2015 to Restriction Requirement mailed Apr. 6, 2015, 1 pg.
U.S. Appl. No. 13/838,755, Response filed Dec. 1, 2015 to Non Final Office Action mailed Sep. 17, 2015, 13 pgs.
U.S. Appl. No. 13/838,755, Restriction Requirement mailed Apr. 6, 2015, 6 pgs.
U.S. Appl. No. 13/889,851, Non Final Office Action mailed Apr. 6, 2015, 10 pgs.
U.S. Appl. No. 13/889,851, Notice of Allowance mailed Aug. 12, 2015, 8 pgs.
U.S. Appl. No. 13/889,851, Response filed Feb. 26, 2015 to Restriction Requirement mailed Jan. 21, 2015, 12 pgs.
U.S. Appl. No. 13/889,851, Response filed Jul. 6, 2015 to Non Final Office Action mailed Apr. 6, 2015, 14 pgs.
U.S. Appl. No. 13/889,851, Restriction Requirement mailed Jan. 21, 2015, 6 pgs.
U.S. Appl. No. 13/889,851, Supplemental Amendment and Response filed Jul. 6, 2015 to Non Final Office Action mailed Apr. 6, 2015, 8 pgs.
U.S. Appl. No. 13/959,145, Final Office Action mailed Jan. 29, 2016, 16 pgs.
U.S. Appl. No. 13/959,145, Final Office Action mailed Feb. 5, 2015, 22 pgs.
U.S. Appl. No. 13/959,145, Non Final Office Action mailed Jul. 31, 2015, 21 pgs.
U.S. Appl. No. 13/959,145, Non Final Office Action mailed Sep. 15, 2014, 20 pgs.
U.S. Appl. No. 13/959,145, Response filed Jul. 6, 2015 to Final Office Action mailed Feb. 5, 2015, 18 pgs.
U.S. Appl. No. 13/959,145, Response filed Oct. 30, 2015 to Non Final Office Action mailed Jul. 31, 2015, 14 pgs.
U.S. Appl. No. 13/959,145, Response filed Dec. 15, 2014 to Non Final Office Action mailed Sep. 15, 2014, 21 pgs.
U.S. Appl. No. 14/055,172, Restriction Requirement mailed Mar. 4, 2016, 6 pgs.
U.S. Appl. No. 14/055,191, Restriction Requirement mailed Mar. 7, 2016, 6 pgs.
Application Serial No, 14/071,295, Non Final Office Action mailed Aug. 15, 2014, 6 pgs.
U.S. Appl. No. 14/071,295, Notice of Allowance mailed Dec. 10, 2014, 8 pgs.
U.S. Appl. No. 14/071,295, Response filed Nov. 17, 2014 to Non Final Office Action mailed Aug. 15, 2014, 14 pgs.
U.S. Appl. No. 14/071,295, Supplemental Notice of Allowability mailed Jan. 26, 2015, 2 pgs.
U.S. Appl. No. 14/095,614, Preliminary Amendment filed Apr. 15, 2014, 17 pgs.
U.S. Appl. No. 14/107,350, Notice of Allowance mailed Feb. 26, 2016, 11 pgs.
U.S. Appl. No. 14/107,350, Preliminary Amendment filed Feb. 28, 2014, 4 pgs.
U.S. Appl. No. 14/211,977, Preliminary Amendment filed Mar. 2, 2016, 7 pgs.
U.S. Appl. No. 14/275,548, Non Final Office Action mailed Feb. 19, 2016, 14 pgs.
U.S. Appl. No. 14/324,688, Non Final Office Action mailed Jan. 8, 2016, 18 pgs.
U.S. Appl. No. 14/456,286, Non Final Office Action mailed Dec. 30, 2015, 16 pgs.
U.S. Appl. No. 14/456,286, Response filed Dec. 11, 2015 to Restriction Requirement mailed Oct. 29, 2015, 6 pgs.
U.S. Appl. No. 14/456,286, Restriction Requirement mailed Oct. 29, 2015, 9 pgs.
U.S. Appl. No. 14/589,101, Final Office Action mailed Oct. 2, 2015, 10 pgs.
U.S. Appl. No. 14/589,101, Non Final Office Action mailed Feb. 12, 2015, 10 pgs.
U.S. Appl. No. 14/589,101, Response filed Jun. 12, 2015 to Non Final Office Action mailed Feb. 12, 2015, 11 pgs.
U.S. Appl. No. 14/589,101, Response filed Dec. 29, 2015 to Final Office Action mailed Oct. 2, 2015, 15 pgs.
U.S. Appl. No. 14/794,309, Preliminary Amendment filed Sep. 22, 2015, 6 pgs.
U.S. Appl. No. 14/794,309, Supplemental Preliminary Amendment filed Mar. 3, 2016, 8 pgs.

(56) References Cited

OTHER PUBLICATIONS

U.S. Appl. No. 14/876,167, Preliminary Amendment filed Oct. 27, 2015, 8 pgs.
U.S. Appl. No. 14/936,831, Preliminary Amendment filed Nov. 11, 2015, 6 pgs.
U.S. Appl. No. 14/956,724, Preliminary Amendment filed Dec. 7, 2015, 8 pgs.
U.S. Appl. No. 14/956,724, Supplemental Preliminary Amendment filed Feb. 11, 2016, 7 pgs.
U.S. Appl. No. 14/983,108, Preliminary Amendment filed Dec. 30, 2015, 7 pgs.
U.S. Appl. No. 14/983,747, Preliminary Amendment filed Jan. 4, 2016, 5 pgs.
U.S. Appl. No. 15/061,352, Preliminary Amendment filed Mar. 7, 2016, 8 pgs.
U.S. Appl. No. 12/938,902, Non Final Office Action mailed Sep. 17, 2012, 11 pgs.
U.S. Appl. No. 12/938,902, Notice of Allowance mailed Jun. 21, 2013, 13 pgs.
U.S. Appl. No. 12/938,902, Notice of Allowance mailed Oct. 1, 2013, 9 pgs.
U.S. Appl. No. 12/938,902, Response filed Aug. 6, 2012 to Restriction Requirement mailed Jul. 6, 2012, 14 pgs.
U.S. Appl. No. 12/938,902, Response filed Dec. 10, 2012 to Non Final Office Action mailed Sep. 17, 2012, 20 pgs.
U.S. Appl. No. 12/938,902, Restriction Requirement mailed Jul. 6, 2012, 8 pgs.
European Application Serial No. 10727548.9, Examination Notification Art. 94(3) mailed Sep. 18, 2014, 6 pgs.
European Application Serial No. 10727548.9, Office Action mailed Jan. 19, 2012, 2 pgs.
European Application Serial No. 10727548.9, Response filed Mar. 19, 2015 to Examination Notification Art. 94(3) mailed Sep. 18, 2014, 23 pgs.
European Application Serial No. 11707316.3, Examination Notification Art. 94(3) mailed Feb. 4, 2014, 3 pgs.
European Application Serial No. 11707316.3, Examination Notification Art. 94(3) mailed Dec. 17, 2014, 5 pgs.
European Application Serial No. 11707316.3, Office Action mailed Nov. 10, 2015, 6 pgs.
European Application Serial No. 11707316.3, Response filed Jun. 5, 2014 to Examination Notification Art. 94(3) mailed Feb. 4, 2014, 7 pgs.
European Application Serial No. 11707316.3, Response filed Jun. 29, 2015 to Examination Notification Art. 94(3) mailed Dec. 17, 2014, 25 pgs.
European Application Serial No. 12721676.0, Office Action mailed Jan. 3, 2014, 2 pgs.
European Application Serial No. 12721676.0, Preliminary Amendment filed Nov. 19, 2013, 9 pgs.
European Application Serial No. 12721676.0, Response filed Jul. 10, 2014 to Office Action mailed Jan. 3, 2014, 2 pgs.
European Application Serial No. 12791902.5, Examination Notification Art. 94(3) mailed Aug. 14, 2015, 4 pgs.
European Application Serial No. 12791902.5, Office Action mailed Jul. 15, 2014, 2 pgs.
European Application Serial No. 12806211.4, Examination Notification Art. 94(3) mailed Aug. 13, 2015, 5 pgs.
European Application Serial No. 12806211.4, Office Action mailed Jul. 18, 2014, 2 pgs.
European Application Serial No. 13818131.8, Office Action mailed Jul. 28, 2015, 2 pgs.
European Application Serial No. 13818131.8, Response filed Feb. 8, 2016 to Office Action mailed Jul. 28, 2015, 14 pgs.
European Application Serial No. 14716173.1, Office Action mailed Nov. 5, 2015, 2 pgs.
International Application Serial No. PCT/US2009/039580, International Preliminary Report on Patentability mailed Nov. 4, 2010, 9 pgs.
International Application Serial No. PCT/US2009/039580, International Search Report mailed Jul. 30, 2009, 4 pgs.
International Application Serial No. PCT/US2009/039580, Written Opinion mailed Jul. 30, 2009, 7 pgs.
International Application Serial No. PCT/US2010/036602, International Preliminary Report on Patentability mailed Dec. 8, 2011, 9 pgs.
International Application Serial No. PCT/US2010/036602, International Search Report mailed Nov. 8, 2010, 6 pgs.
International Application Serial No. PCT/US2010/036602, Written Opinion mailed Nov. 8, 2010, 7 pgs.
International Application Serial No. PCT/US2012/030294, International Preliminary Report on Patentability mailed Oct. 10, 2013, 9 pgs.
International Application Serial No. PCT/US2012/030294, International Search Report mailed May 23, 2012, 6 pgs.
International Application Serial No. PCT/US2012/030294, Written Opinion mailed May 23, 2012, 7 pgs.
International Application Serial No. PCT/US2012/062738, International Preliminary Report on Patentability mailed May 15, 2014, 9 pgs.
International Application Serial No. PCT/US2012/062738, International Search Report mailed Mar. 6, 2013, 6 pgs.
International Application Serial No. PCT/US2012/062738, Written Opinion mailed Mar. 6, 2013, 7 pgs.
International Application Serial No. PCT/US2013/075989, International Preliminary Report on Patentability mailed Jul. 2, 2015, 10 pgs.
International Application Serial No. PCT/US2014/026413, International Preliminary Report on Patentability mailed Sep. 24, 2015, 10 pgs.
"PANALOK Anchor with PDS II and ETHIBOND Suture", Mitek Products ETHICON, (1997), 2 pgs.
"SportMesh™ Soft Tissue Reinforcement, Made from . . . Artelon® optimal tissue repair", Biomet® Sports Medicine, Inc., (2007), 8 pgs.
Alford, J Winslow, et al., "Cartilage Restoration, Part 1. Basic Science, Historical Perspective, Patient Evaluation, and Treatment Options", The American Journal of Sports Medicine, 33(2), (2005), 295-306.
Anitua, Eduardo, et al., "Autologous platelets as a source of proteins for healing and tissue regeneration", Thromb Haemost, vol. 91, (2004), 4-15.
Arthrotek, "A Biomet Company; Sure fire Hybrid Meniscal Device", Fall AANA, (2004), 37 pgs.
Depuy, Mitek, "Bio-Intrafix Tibial Soft Tissue Fastener, Building on the Legacy of IntraFix", brochure, (Feb. 2007), 6 pgs.
Edwards, Andrew, et al., "The Attachments of the Fiber Bundles of the Posterior Cruciate ligament: An Anatomic Study", Arthroscopy: The Journal of Arthroscopic and Related Surgery, vol. 23, No. 3, (Mar. 2008), 284-290.
Floryan, K. et al., "Intraoperative use of Autologous Platelet-Rich and Platelet-Poor Plasma for Orthopedic Surgery Patients", AORN Journal: Home Study Program, 80(4), (Oct. 2004), 667-674.
Haynesworth, S E, et al., "Mitogenic Stimulation of Human Mesenchymal Stem Cells by Platelet Releasate Suggests a Mechanism for Enhancement of Bone Repair by Platelet Concentrate", 48th Annual Meeting of the Orthopaedic Research Society Poster No. 0462, (2002), 1 pg.
Mithoefer, Kai MD, et al., "The Microfracture Technique for the Treatment of Articular Cartilage Lesions in the Knee. A Prospective Cohort Study", The Journal of Bone and Joint Surgery 87(9), (Sep. 2005), 1911-1920.
Nixon, A J, "Platelet Enriched Plasma Provides an Intensely Anabolic Vehicle for Sustained Chondrocyte Function After Implantation", 52nd Annual Meeting of the Orthopedic Research Society: Paper No. 1416, (2005), 2 pgs.
Roseberg, MD, Thomas D, "ACL Reconstruction with Acufex Director Drill Guide and Endobutton CL Fixation System", Smith & Nephew: Knee Series, Technique Guide, (2005), 12 pgs.
Steadman, et al., "Microfracture: Surgical Technique and Rehabilitation to Treat Chondral Defects", Clinical Orthopaedics and Related Research 391, (2001), S362-S369.
U.S. Appl. No. 12/938,902, Examiner Interview Summary mailed Dec. 3, 2012, 3 pgs.

(56) References Cited

OTHER PUBLICATIONS

U.S. Appl. No. 13/109,672, 312 Amendment filed Jan. 15, 2015, 3 pgs.
U.S. Appl. No. 13/109,672, Non Final Office Action mailed May 15, 2014, 10 pgs.
U.S. Appl. No. 13/109,672, Notice of Allowance mailed Feb. 3, 2015, 2 pgs.
U.S. Appl. No. 13/109,672, Notice of Allowance mailed Sep. 29, 2014, 9 pgs.
U.S. Appl. No. 13/109,672, PTO Response to Rule 312 Communication mailed Jan. 27, 2015, 2 pgs.
U.S. Appl. No. 13/109,672, Response filed Apr. 14, 2014 to Restriction Requirement mailed Feb. 14, 2014, 15 pgs.
U.S. Appl. No. 13/109,672, Response filed Aug. 15, 2014 to Non Final Office Action mailed May 15, 2014, 20 pgs.
U.S. Appl. No. 13/109,672, Response filed Nov. 4, 2013 to Restriction Requirement mailed Oct. 2, 2013, 10 pgs.
U.S. Appl. No. 13/109,672, Restriction Requirement mailed Feb. 14, 2014, 7 pgs.
U.S. Appl. No. 13/109,672, Restriction Requirement mailed Oct. 2, 2013, 7 pgs.
U.S. Appl. No. 13/177,153, Final Office Action mailed May 28, 2013, 11 pgs.
U.S. Appl. No. 13/177,153, Non Final Office Action mailed Oct. 2, 2012, 11 pgs.
U.S. Appl. No. 13/177,153, Notice of Allowance mailed Jan. 7, 2014, 4 pgs.
U.S. Appl. No. 13/177,153, Notice of Allowance mailed Sep. 17, 2013, 13 pgs.
U.S. Appl. No. 13/177,153, Response filed Aug. 28, 2013 to Final Office Action mailed May 28, 2013, 19 pgs.
U.S. Appl. No. 13/177,153, Response filed Sep. 4, 2012 to Restriction Requirement mailed Aug. 2, 2012, 15 pgs.
U.S. Appl. No. 13/177,153, Response filed Dec. 20, 2012 to Non Final Office Action mailed Oct. 2, 2012, 16 pgs.
U.S. Appl. No. 13/177,153, Restriction Requirement mailed Aug. 2, 2012, 9 pgs.
U.S. Appl. No. 13/645,964, Non Final Office Action mailed Mar. 15, 2016, 15 pgs.
U.S. Appl. No. 13/751,846, Notice of Allowance mailed Mar. 16, 2016, 11 pgs.
U.S. Appl. No. 14/211,977, Restriction Requirement mailed Mar. 11, 2016, 6 pgs.
U.S. Appl. No. 15/060,007, Preliminary Amendment filed Mar. 9, 2016, 9 pgs.
International Application Serial No. PCT/US2012/037703, Written Opinion mailed Nov. 28, 2013.
US 6,238,418, 05/2001, Schwartz et al. (withdrawn)

* cited by examiner

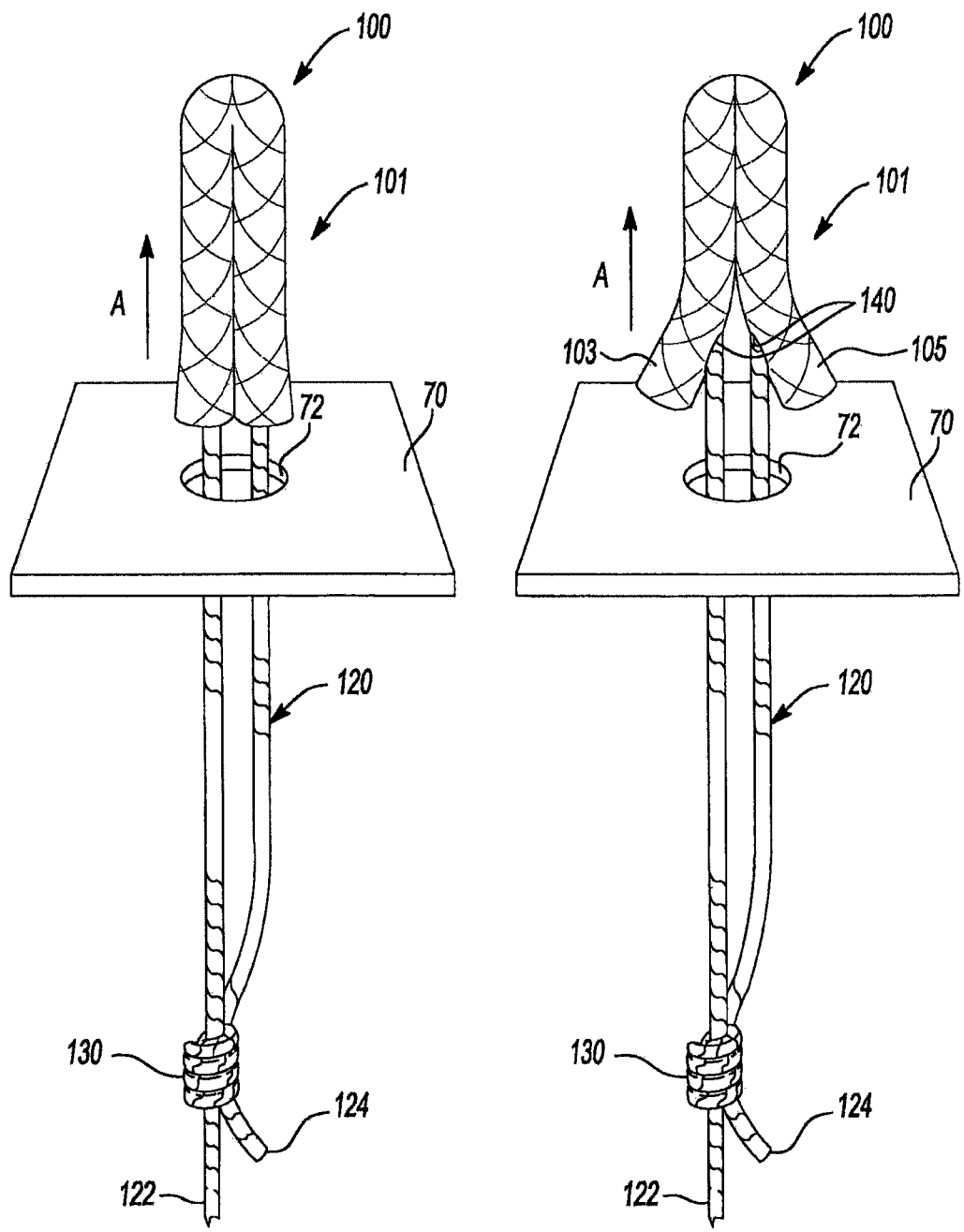

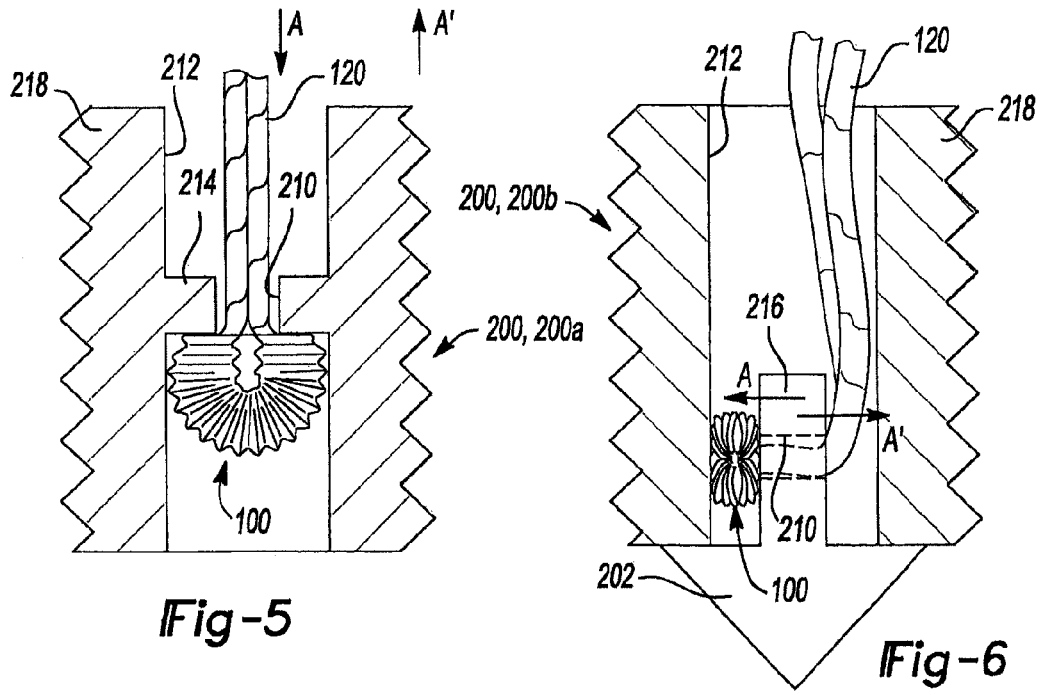
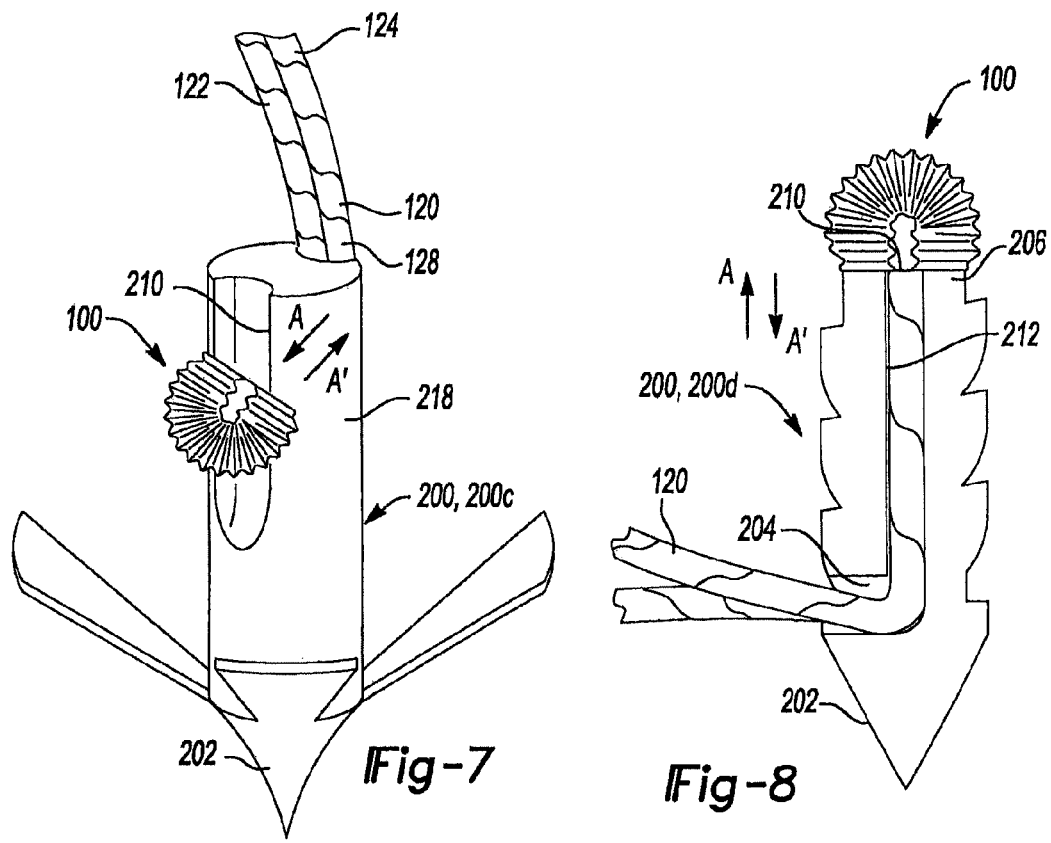

METHOD FOR TISSUE FIXATION

CROSS-REFERENCE TO RELATED APPLICATIONS

This application is a divisional of U.S. patent application Ser. No. 12/489,181 filed Jun. 22, 2009, now U.S. Pat. No. 8,298,262 which is a continuation-in-part application of: (1.) U.S. patent application Ser. No. 12/474,802 filed on May 29, 2009, now U.S. Pat. No. 8,088,130 issued on Jan. 3, 2012, (2.) U.S. patent application Ser. No. 11/541,506 filed on Sep. 29, 2006, now U.S. Pat. No. 7,601,165 issued on Oct. 13, 2009, (3.) U.S. patent application Ser. No. 11/541,505 filed on Sep. 29, 2006, now U.S. Pat. No. 7,658,751 issued on Feb. 9, 2010, (4.) U.S. patent application Ser. No. 12/014,399 filed on Jan. 15, 2008, now U.S. Pat. No. 7,909,851 issued on Mar. 22, 2011, (5.) U.S. patent application Ser. No. 12/014,340 filed on Jan. 15, 2008, now U.S. Pat. No. 7,905,904 issued on Mar. 15, 2011, (6.) U.S. patent application Ser. No. 11/935,681 filed on Nov. 6, 2007, now U.S. Pat. No. 7,905,903 issued on Mar. 15, 2011, (7.) U.S. patent application Ser. No. 11/869,440 filed on Oct. 9, 2007, now U.S. Pat. No. 7,857,830 issued on Dec. 28, 2010, (8.) U.S. patent application Ser. No. 11/784,821 filed on Apr. 10, 2007, (9.) U.S. patent application Ser. No. 11/347,661 filed on Feb. 3, 2006, now U.S. Pat. No. 7,749,250 issued on Jul. 6, 2010, and (10.) U.S. patent application Ser. No. 11/347,662 filed on Feb. 3, 2006, which is now abandoned.

This application is also a divisional of U.S. patent application Ser. No. 13/412,116 filed on Mar. 5, 2012, now U.S. Pat. No. 8,771,316 which is a continuation-in-part of: (1.) U.S. patent application Ser. No. 12/196,405 filed on Aug. 22, 2008, now U.S. Pat. No. 8,128,658 issued on Mar. 6, 2012, (2.) U.S. patent application Ser. No. 12/196,407 filed on Aug. 22, 2008, now U.S. Pat. No. 8,137,382 issued on Mar. 20, 2012, and (3.) U.S. patent application Ser. No. 12/196,410 filed on Aug. 22, 2008, now U.S. Pat. No. 8,118,836 issued on Feb. 21, 2012.

The disclosures of the above applications are incorporated herein by reference.

INTRODUCTION

Trauma or disease in soft tissue, such as cartilage, ligament, or muscle can cause tears or detachment from bone or other defects that can be repaired by reattaching or securing the soft tissue to the bone. Various devices and methods are known for attaching and securing soft tissue to bone.

The present teachings provide a versatile tissue fixation method that can be used with various bone anchors or other implantable fixation members to attach soft tissue to bone or any tissue to other tissue.

SUMMARY

The present teachings provide a method for securing a strand to at least one fixation member for a surgical procedure, wherein the fixation member includes an aperture therethrough. The method includes passing a strand having first and second ends through a flexible sleeve, passing the sleeve through the aperture of the fixation member in a first direction, tensioning the strand, and moving the sleeve in a second direction different than the first direction to secure the sleeve to the fixation member without tying the strand on the fixation member.

The present teachings provide a method for securing a strand to a plurality of anchors for a surgical procedure. The method includes inserting a plurality of anchors into the bone, passing a flexible strand having first and second ends through a plurality of flexible sleeves serially coupled on the strand, passing each sleeve in a first configuration into and through an aperture of a corresponding anchor in a first direction, deforming each sleeve to a second configuration, and tying a single knot at the first and second ends of the strand.

The present teachings provide a method for securing a strand to a plurality of bone anchors for a surgical procedure. The method includes passing a flexible strand slidably through a plurality of flexible sleeves, forming a single slipknot on a portion of the strand outside all the sleeves, the slipknot the defining a closed loop, knotlessly securing each sleeve into a corresponding bone anchor, and reducing a length of the loop.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein:

FIG. 2 is a perspective view of the connector device of FIG. 1, shown prior to engagement with a representative aperture;

FIG. 2A is a perspective view of the connector device of FIG. 1C, shown prior to engagement with a representative aperture;

FIG. 5 is a side view of the connector device of FIG. 1, shown with a first anchor;

FIG. 6 is a side view of the connector device of FIG. 1, shown with a second anchor;

FIG. 7 is a side view of the connector device of FIG. 1, shown with a third anchor;

FIG. 8 is a side view of the connector device of FIG. 1, shown with a fourth anchor.

DESCRIPTION OF VARIOUS ASPECTS

The following description is merely exemplary in nature and is in no way intended to limit the scope of the present teachings, applications, or uses. The present teachings can be used for various orthopedic applications including coupling bone to bone, bone to soft tissue, soft tissue repair, and generally attaching soft tissue to bone, or attaching suture or other anchors to bone, or any other tissue repair procedure. The present teachings can also be used for repairing any fibrous tissue, such as muscle, ligament or tendon in an arthroscopic or other open procedure, including rotator cuff reconstruction, acromioclavicular (AC) reconstruction, anterior cruciate ligament reconstruction (ACL) and generally for fastening tendons, grafts, or strands to fibrous tissue and bone. Additionally, the present teachings can be used for repairing tissue in cardiological, laparoscopic, urological, plastic, blood vessels, annulus of spine or other procedures.

Figure 1:
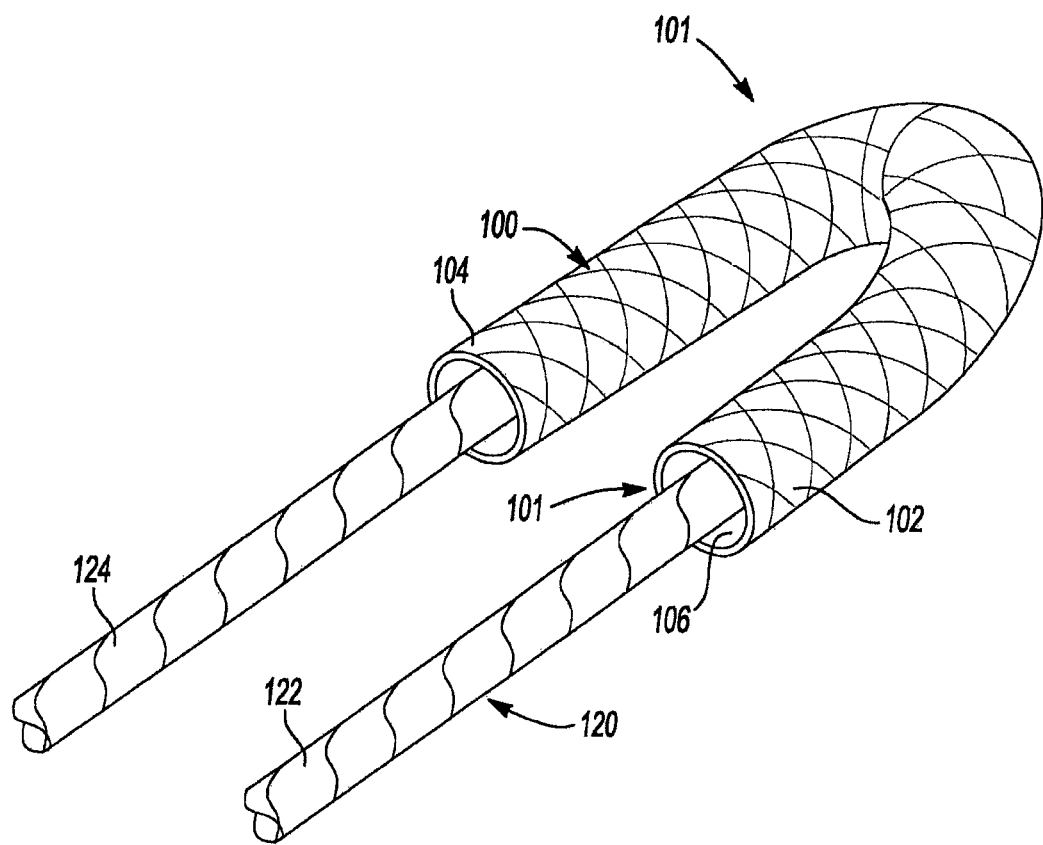
FIG. 1 is a perspective view of a connector device according to the present teachings.

Referring to FIG. 1, an exemplary connector device 101 that can be used for attaching soft tissue to bone is illustrated. The connector device 101 can include a flexible tubular sleeve or tube 100 having an inner bore 106 that extends between first and second open ends 102, 104. The sleeve 100 can be made of resorbable or non-resorbable materials, including braided suture, sponges and sponge-like, perforated materials, woven/braided from biocompatible materials or fibers, such as, for example, polymer, polyester, polyethylene, cotton, silk, or other natural or synthetic materials. The sleeve 100 can be made of suture material braided from thin filaments into a form that does not include a core filament. The sleeve 100 can have a generally flaccid shape that can be manipulated in different configurations like a piece of string or shoelace, for example. Accordingly, the sleeve 100 can be bent, folded or otherwise manipulated or deformed into various configurations, such as a bent or U-shape configuration shown in FIGS. 1, 1A and 1B, or a substantially straight configuration shown in FIG. 4, or a deformed or bunched-up, puckered configuration, such as the ball-like configuration shown in FIG. 3, or the bell-like shaped shown in FIG. 3A, as discussed below.

Figure 1A:
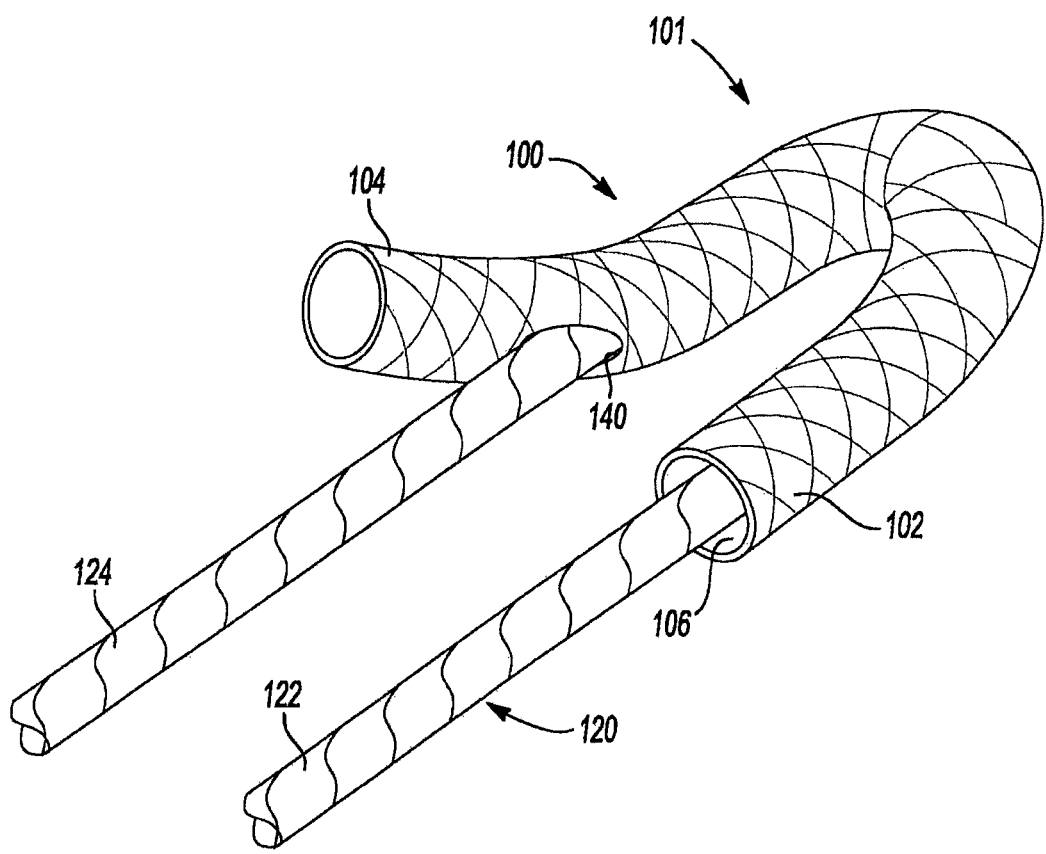
FIG. 1A is a perspective view of a connector device according to the present teachings.
Figure 1B:
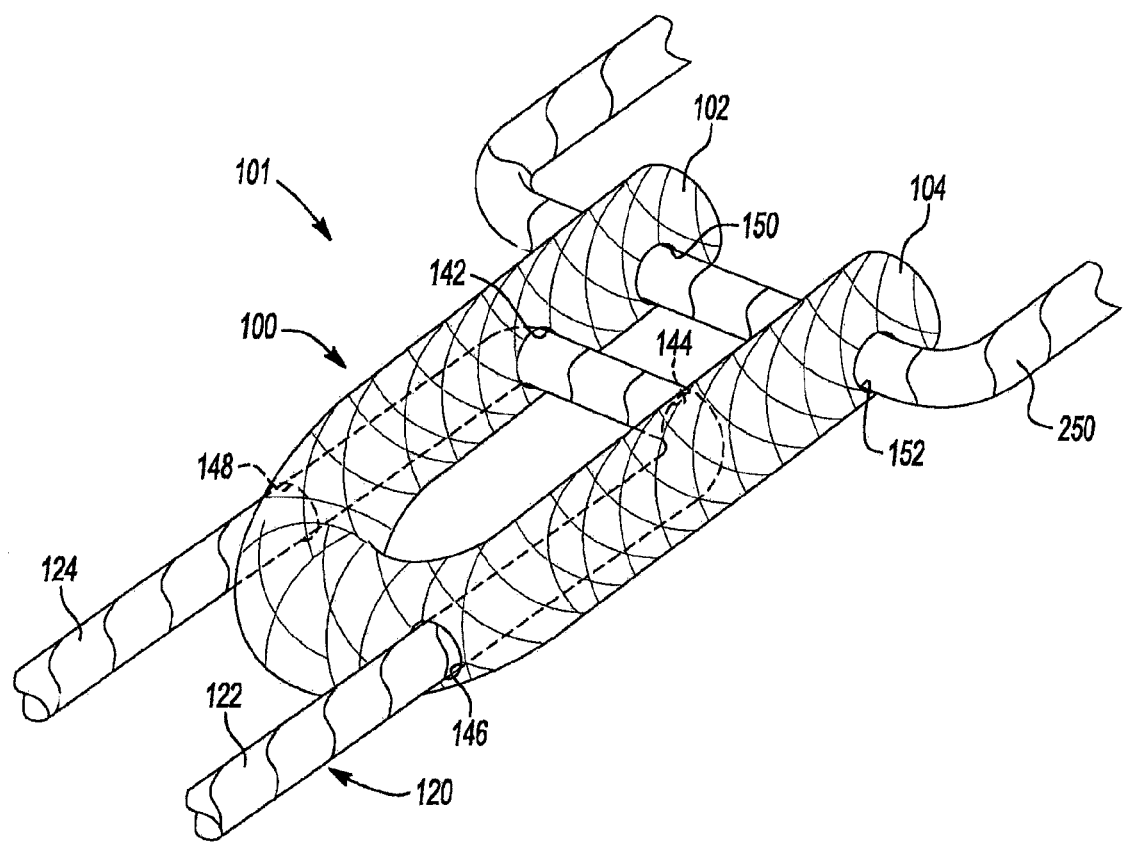
FIG. 1B is a perspective view of another connector device according to the present teachings.
Figure 1C:
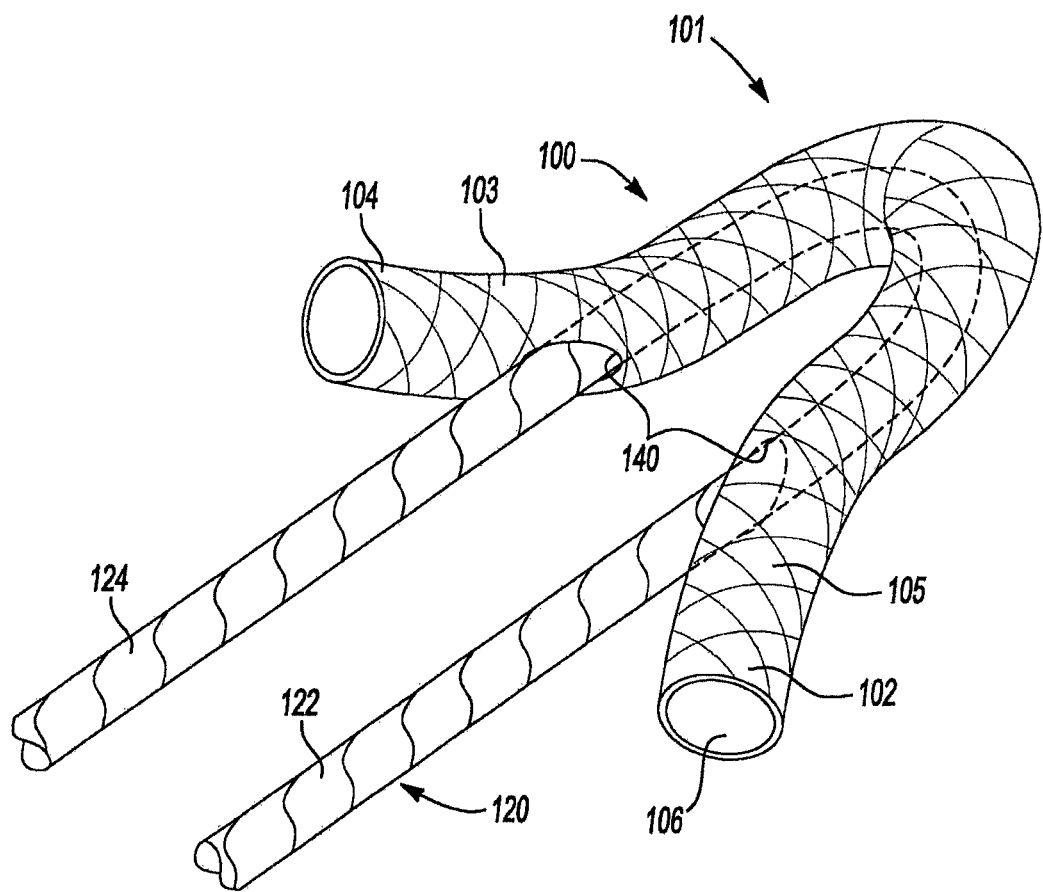
FIG. 1C is a perspective view of another connector device according to the present teachings.

Referring to FIGS. 1, 1A, 1B, and 1C the connector device 101 can also include an elongated flexible strand 120 having first and second ends 122, 124. The strand 120 can pass axially through the bore 106 of the sleeve 100, such that the first and second strand ends 122, 124 exit the corresponding first and second ends 102, 104 of the sleeve 100, as illustrated in FIG. 1. In one aspect, the strand 120 can exit the bore 106 through at least one opening 140 of the sleeve 100 intermediate the first and second ends 102, 104 of the sleeve, as shown in FIG. 1A. In another aspect, the strand 120 can exit the bore 106 through two openings 140 of the sleeve 100 intermediate the first and second ends 102, 104 of the sleeve 100, as shown in FIG. 1C. First and second end portions or sleeve legs 103, 105, are defined between each end 104, 102 and the corresponding opening 140. In another aspect, the strand 120 can pass through openings 142, 144, 146, 148, such that an intermediate portion of the strand 120 is outside the bore 106, as shown in FIG. 1B.

The strand 120 can also be made of materials similar to the sleeve 100, such as braided filaments or fibers of biocompatible material, including natural and synthetic fibers, such as cotton, silk, polymer, polyester, polyethylene, thin wire, suture, and other materials. The strand 120 can also be in the form of a flat tubular suture or a braided suture with or without a core. The connector device 101 with the sleeve 100 and strand 120 are implantable in soft tissue or bone.

Referring to FIGS. 1-3A, a general procedure for using the connector device 101 is illustrated. The sleeve 100 with the strand 120 therethrough can be folded and pushed through on orifice 72 or other aperture defined through a support 70 in the direction of arrow "A", as shown in FIGS. 2 and 2A. The strand ends of 122, 124 can be connected with a knot 130, such as slipknot, forming a strand loop 128 passing through the bore 106 of the sleeve 100.

Figures 3, 3A:
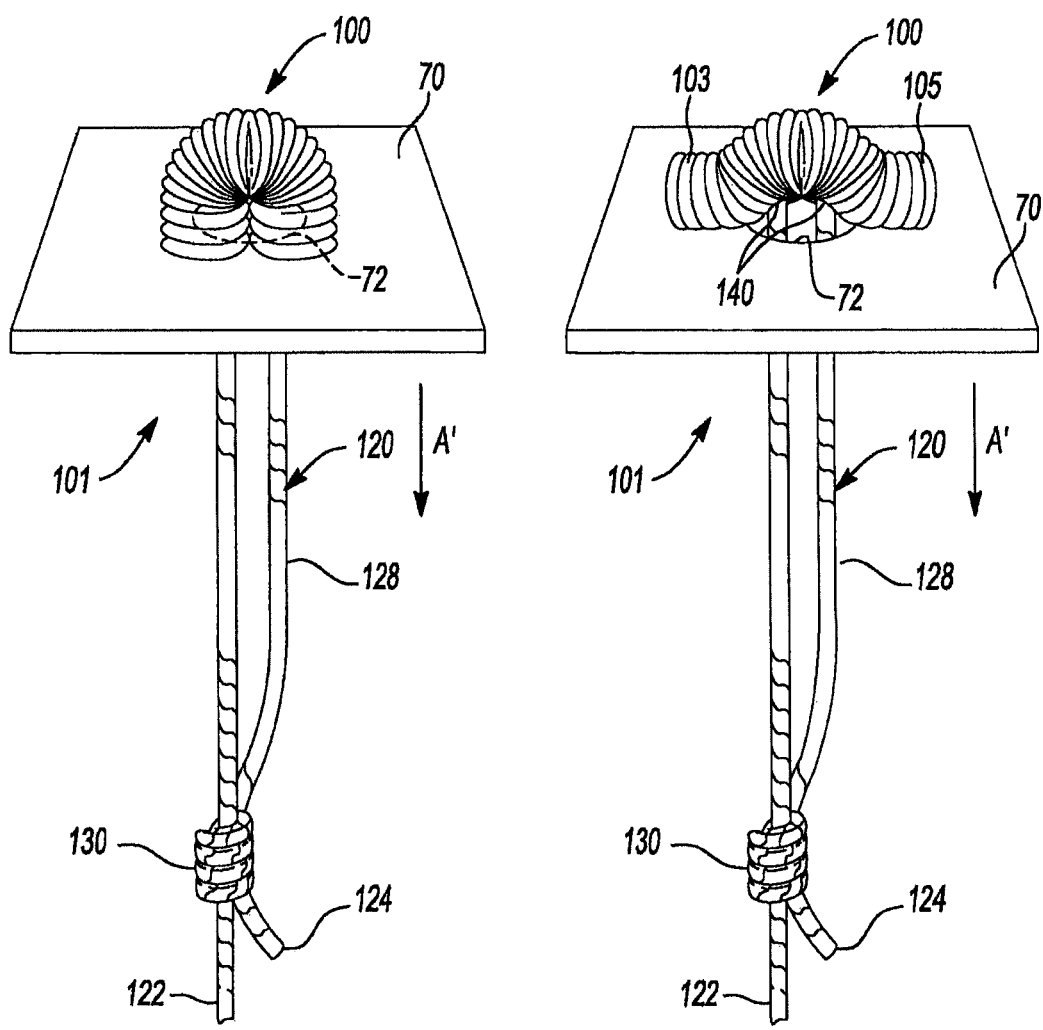
FIG. 3 is a perspective view of the connector device of FIG. 1, shown in engagement with a representative aperture.
FIG. 3A is a perspective view of the connector device of FIG. 1C, shown in engagement with a representative aperture.

Referring to FIGS. 2 and 3, pulling on one of the strand ends 122, 124, shortens the length of the strand loop 128 and the tension causes the sleeve 100 to change configuration, bunching up from a folded and/or flaccid configuration to a bunched-up, ball-like configuration that cannot pass through the orifice 72, such that the strand 120 can be secured on the support 70. In this configuration, the strand ends 122, 124 and the sleeve 100 remain on opposite sides of the orifice 72.

Similarly, and referring to FIGS. 2A and 3A, pulling on one of the strand ends 122, 124, shortens the length of the strand loop 128 and the tension causes the sleeve 100 to change configuration, bunching up from a folded and/or flaccid configuration to a bunched-up bell-like shape with the legs 103, 105 extended outward and pressed against the support 70. In this configuration, the sleeve 100 cannot pass through the orifice 72 in the direction of the arrow A'. The strand ends 122, 124 and the sleeve 100 remain on opposite sides of the orifice 72, and the legs 103, 105 provide additional resistance for securing the strand 120 to the support 70.

The orifice 72 can be of any shape, including any regular or irregular closed curves or polygons, or combination thereof, including circular elliptical, oval, triangular, tetragonal, hexagonal, lobed, or other shapes. The shape and size of the orifice 72 is such that the sleeve 100 in its bent shape deforms sufficiently to slide through the orifice 72 when introduced along one direction A. Once the sleeve 100 passes through and out of the orifice 72 and returns to its undeformed flaccid configuration, the sleeve 100 will bunch up against the orifice 72 when directed or pulled in the opposite direction A', as the ends 102, 104 of the sleeve 100, or the sleeve legs 103, 105, and/or deformed shape are caught against the support 70. It is noted that the strand 120 can still slide relative to the sleeve 100 and the orifice 72, therefore the orifice 72 can act effectively as an anchor eyelet.

The support 70 can be soft tissue, bone, implant, anchor or other threaded or unthreaded implantable fixation member such as those illustrated in FIGS. 5-8 at 200. The fixation members are generically referenced with numeral 200 or specifically with reference numerals 200a-200d. The connector device 101 and the fixation member 200 can form an implantable fixation assembly that can be used for securing soft tissue to bone, as further discussed below in connection with FIG. 9.

It will be appreciated that the connector device 101 can be used as a versatile suture lock that is easy to use, avoids knot-tying, and saves time during the surgical procedure. Further, as the flexible strand 120 is held against the support 70, the flexible strand 120 is prevented from pulling through without being knot-tied to the support 70. It is estimated that the flexible strand 120 can withstand a pulling force greater than that in a knot tied in the same-sized strand.

Any of the connector devices 101 illustrated in FIGS. 1, 1A, 1B, 1C, or combinations thereof, can be used with a fixation member 200 for fastening any type of ligaments, grafts or sutures, and can be used, for example, for rotator cuff repair for the shoulder, for acromioclavicular (AC) joint reconstruction, for tibial graft fixation, for ACL reconstruction, and generally for fastening tendons or grafts and sutures to tissue, including soft tissue and bone. In many of such shoulder repair procedures, a tendon is secured to the bone with many suture anchors requiring repeated knot-tying. Such knot-tying is cumbersome and time consuming during an arthroscopic procedure, as it is generally performed through an insertion cannula that is used to deliver the suture anchor. As discussed below, the connector device 101 illustrated in FIGS. 4 and 9 can be used to secure multiple suture anchors or other fixation members 200 without individual knots for each fixation member 200, and with only one final knot 130 for the entire series of fixation members 200 outside the cannula. Moreover, the knot 130 that forms the single loop 128 of the flexible strand 120 can be pre-tied.

Figure 4:
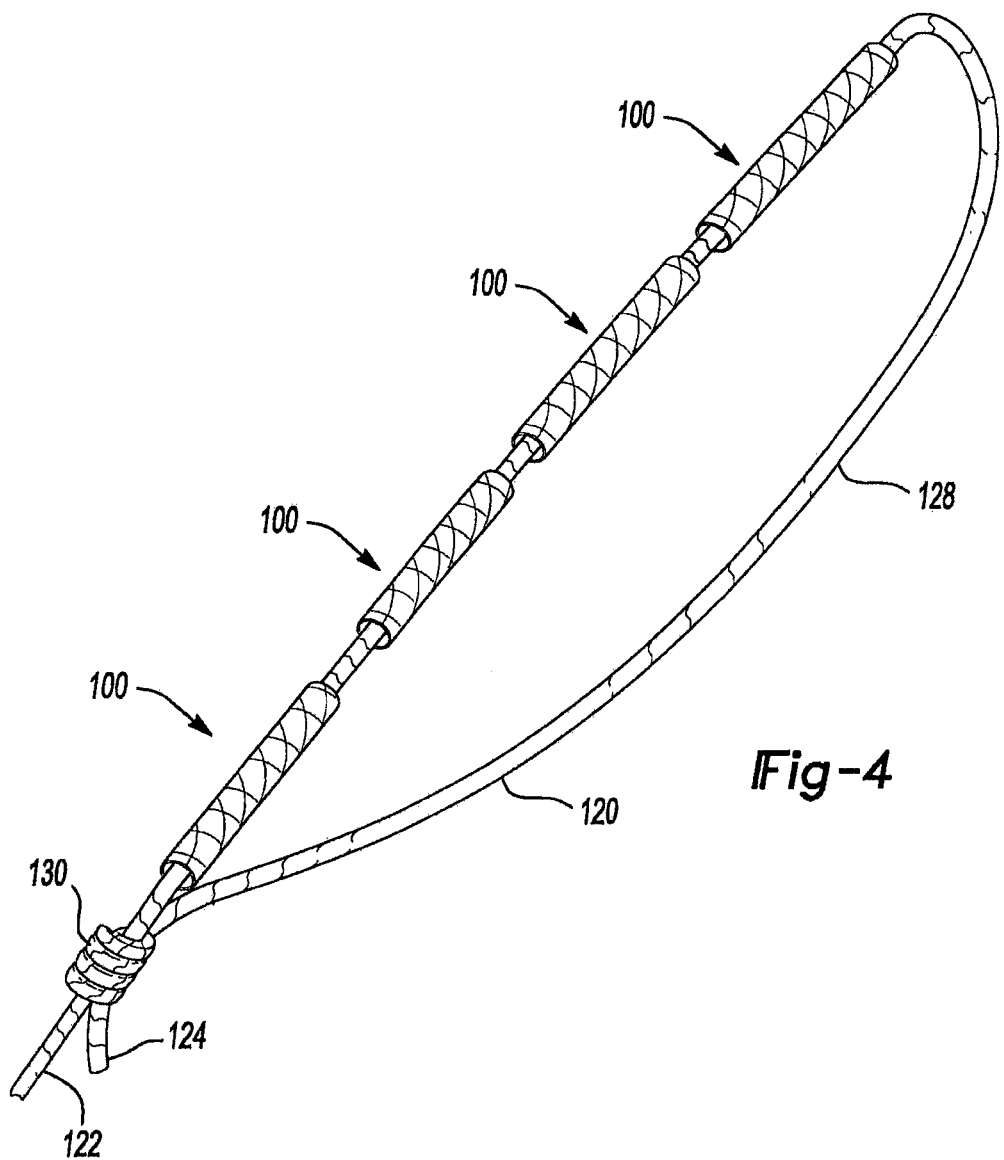
FIG. 4 is a perspective view of a series of interconnected connector devices according to the present teachings.
Figure 9:
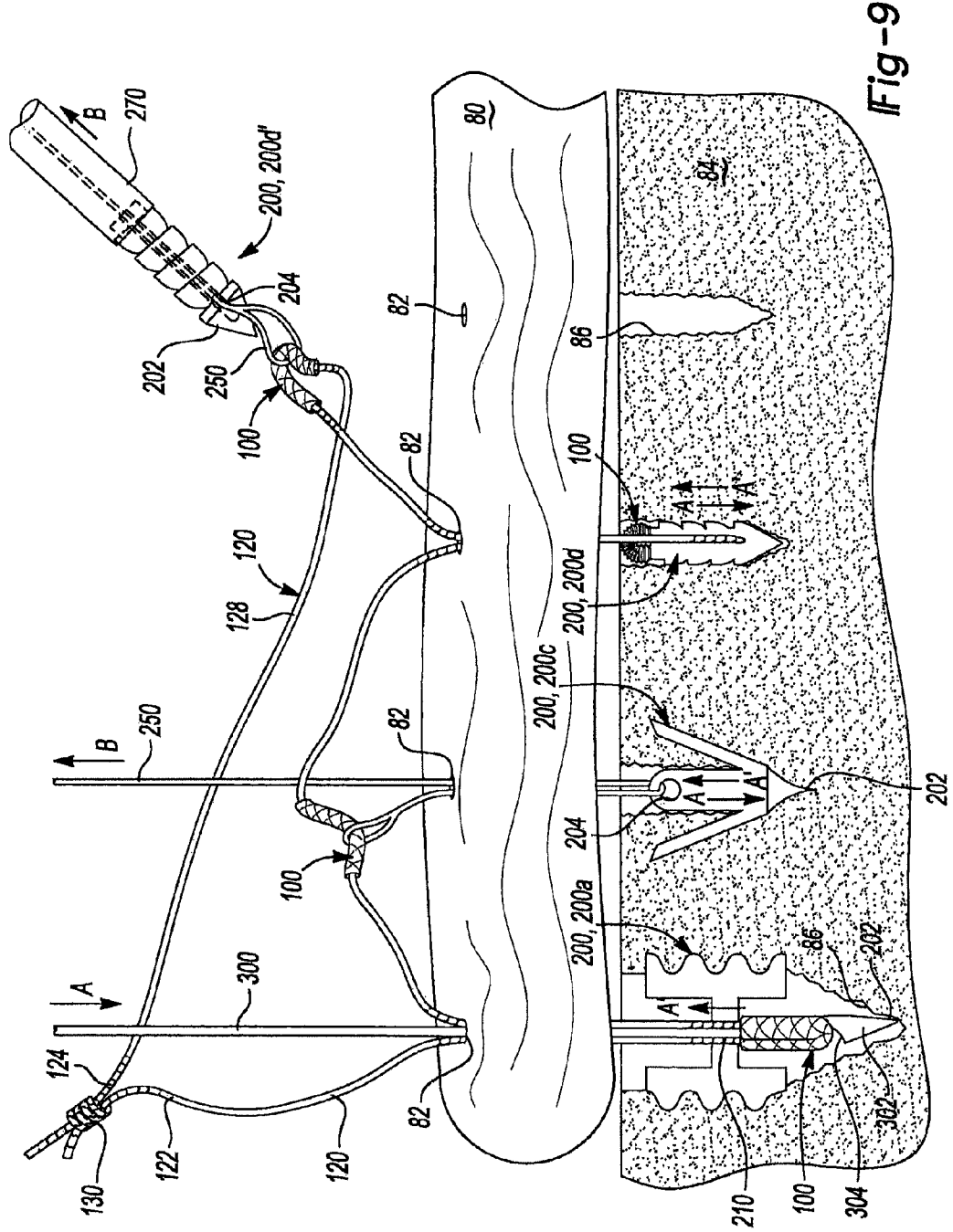
FIG. 9 is an exemplary method of using a series of interconnected connector devices for securing soft tissues to bone.
Figure 10A:
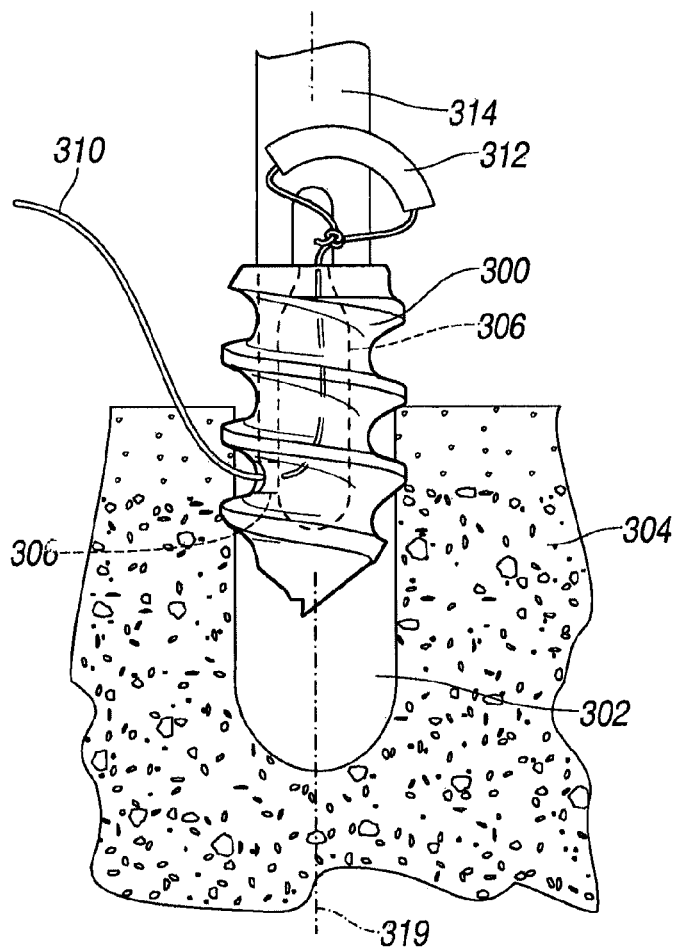
FIGS. 10A-15 represent various suture constructions coupled to a hollow fixation element.
Figure 10B:
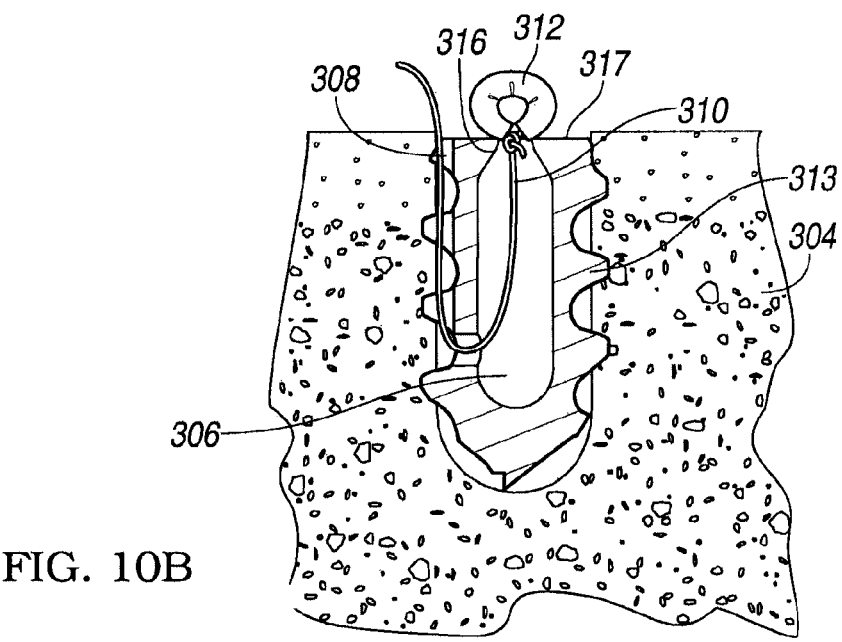
Figure 11A:
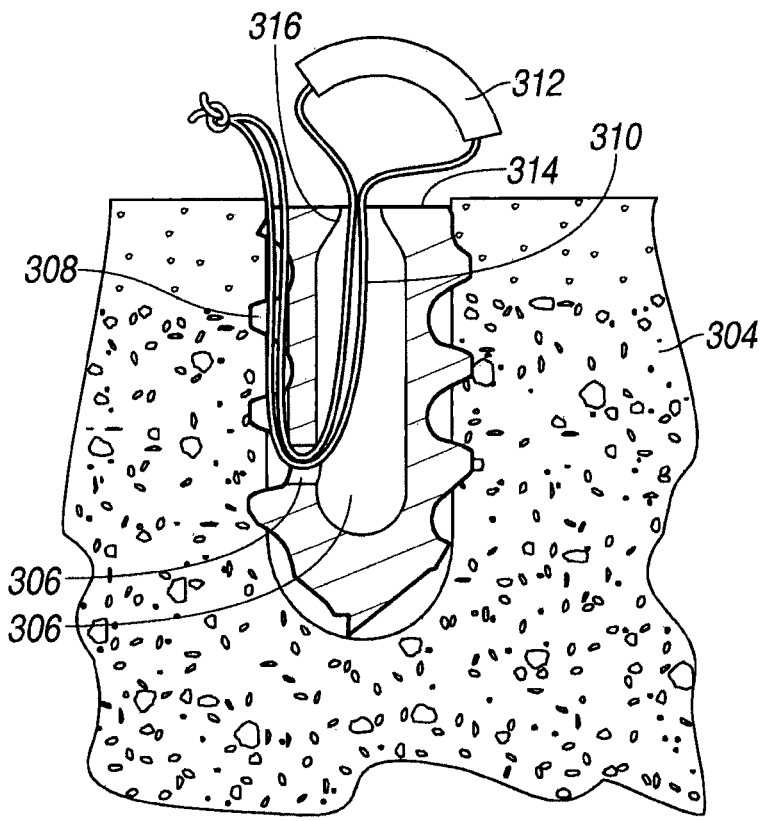
Figure 11B:
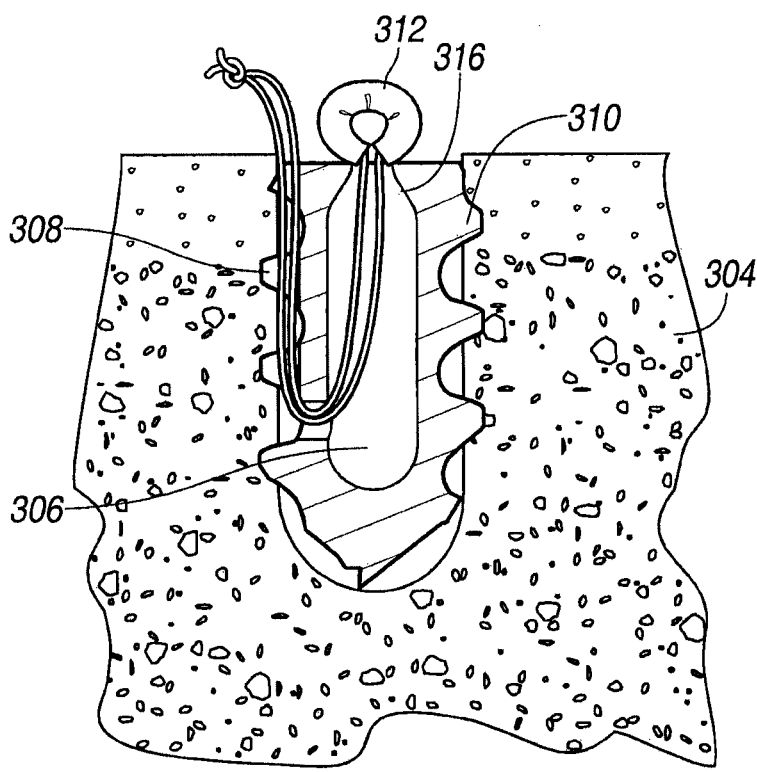
Figure 12A:
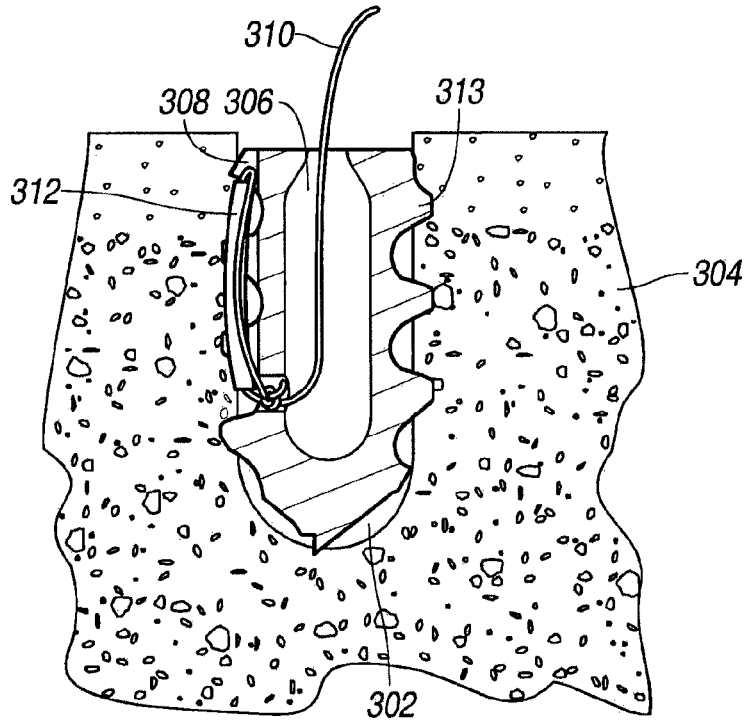
Figure 12B:
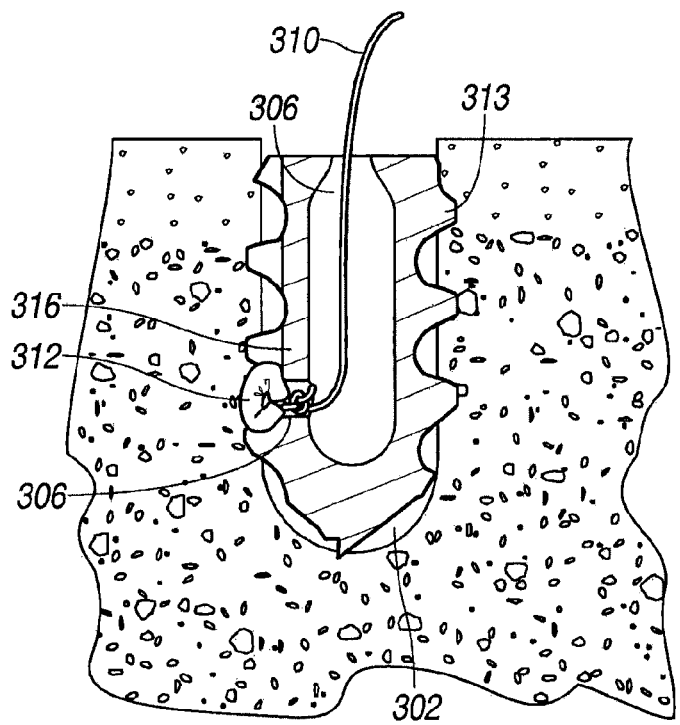
Figure 13:
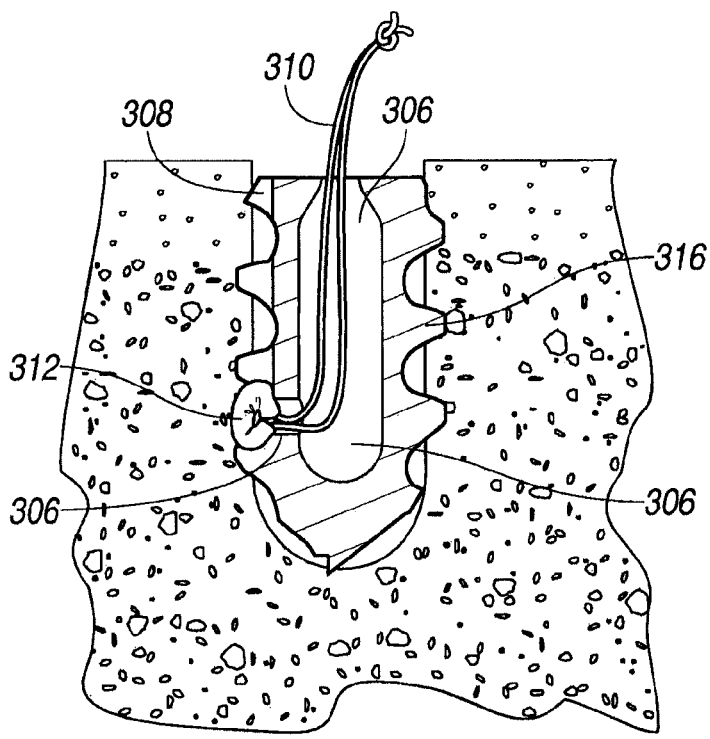

Referring to FIG. 5, the fixation member 200 can be in the form of an externally threaded open-ended tubular member 200a and can include a body 218 having an open-ended longitudinal bore 212 interrupted by a cross-wall 214. The wall 214 defines a through-slot or other aperture 210 substantially coaxial with the bore 212. The sleeve 100 can pass through the aperture 210 in a folded configuration in the direction of arrow A, while the strand ends 122, 124 of the strand 120 remaining outside the fixation member 200. The sleeve 100 can be held against the wall 214 in a bunched-up (ball or bell-like) configuration when pulled by the strand 120 in the direction A'. In the same manner, a plurality of sleeves 100 strung together in a single loop 128 of a single strand 120, as shown in FIG. 4, can be secured to a corresponding plurality of fixation members 200, without requiring individual knots, as shown in FIG. 9 and discussed below. Using a plurality of sleeves 100 in a single loop 128 allows a fast and efficient procedure of creating a suture mat for attaching soft tissue 80 to bone 84 in multiple locations without having to tie knots arthroscopically through a cannula for each individual fixation member 200.

Referring to FIG. 6, the fixation member 200 can be an implant in the form of a tubular anchor 200b having a body 218 and include a longitudinal bore 212 closed at one end with a pointed anchoring tip 202. The anchoring tip 202 can be integrally or removably coupled to the body 218. The anchoring tip 202 can include a longitudinal extension 216 received in the bore 212. The extension 216 can define an aperture 210 substantially parallel with the bore 212. The sleeve 100 can be passed through the aperture 210 in the direction of arrow A, such that the strand 120 passes through the aperture 210, through the bore 212 and exits the fixation member 200. The sleeve 100 can be held between a wall of the bore 212 and the extension 216 in a bunched-up (ball or bell-like) configuration after the strand 120 is pulled away from the fixation member 200 in another direction, such as the direction of arrow A'. It should be appreciated that the directions A and A' need not be opposite. Pulling in any direction A' that will cause the strand 120 to tension can suffice. Although FIGS. 5 and 6 illustrate examples of an aperture 210 that is respectively coaxially or perpendicularly oriented relative to the bore 212 of the fixation member 200, it will be appreciated that the aperture 210 is not limited to these orientations. The fixation member 200b can also be used in a single loop 128 with multiple similar or different fixation members 200 for attaching soft tissue 80 to bone 84 in multiple locations, as illustrated in FIG. 9.

Referring to FIG. 7, the fixation member 200 can be an implant in the form of harpoon-type anchor 200c having a pointed anchoring tip 202. The fixation member 200 can include a central body 218 defining an aperture 210. The sleeve 100 can be passed through the aperture 210 in the direction of arrow A. The strand 120 can form a loop 128 passing through the aperture 210 in the direction of arrow A. The strand ends 122, 124 can be pulled away from the fixation member 200 in the direction of arrow A', such that the sleeve 100 is held against the body 218 in a bunched-up (ball or bell-like) configuration. The fixation member 200c can also be used in a single loop 128 with multiple similar or different fixation members 200 for attaching soft tissue 80 to bone 84 in multiple locations, as illustrated in FIG. 9.

Referring to FIG. 8, the fixation member 200 can be an implant in the form of an externally threaded suture anchor 200d having a body 218 with an anchoring tip 202 and including a longitudinal bore 212 extending from a proximal end 206 to a distal eyelet 204. The sleeve 100 can be passed through the eyelet 204, the bore 212 and the aperture 210 defined at proximal end 206 of the bore 212 in the direction of arrow A. The strand 120 can form a loop 128 passing through the bore 212 and exiting the eyelet 204. The strand ends 122, 124 can be pulled away from the fixation member 200 in the direction of arrow A', such that the sleeve 200 can be secured against the proximal end 206 in a bunched-up (ball or bell-like) configuration. The fixation member 200d can also be used in a single loop 128 with multiple similar or different fixation members 200 for attaching soft tissue 80 to bone 84 in multiple locations, as illustrated in FIG. 9.

The connector device 101 can be pushed through the aperture in the fixation member 200 using an inserter, such as the inserter 300 shown in FIG. 9 and the inserter described and shown in FIGS. 8A-9B and 13-15 of the cross-referenced patent application Ser. No. 11/347,661 filed on Feb. 3, 2006, although other inserters can also be used. The sleeves 100 of the connector device 101 can be coupled to corresponding fixation members 200, either before or after the fixation members 200 are secured in the bone 84.

Referring to FIGS. 4 and 9, a series of sleeves 100 can be strung along a single loop or chain 128 of the strand 120 without other knots except a single slipknot 130 coupling the strand ends 122, 1224. Each sleeve 100 can be inserted in a corresponding prepared bone bore 84 or in a corresponding fixation member 200 to attach soft tissue 80 to a bone 84. It will be appreciated that identical or different fixation members 200, such as, for example, fixation members 200a-200d, can be used for securing the corresponding sleeves 100, and one or more fixation members 200 can be omitted, such that the sleeve 100 is secured directly in a bone bore 86 without using a fixation member 200. Some exemplary options are illustrated in a single illustration in FIG. 9.

It will be appreciated that the sleeve 100 can be inserted or secured to the fixation member 200 either before or after the fixation member 200 has been implanted into the bone 84. For example, the sleeve 100 can be secured to the fixation member 200 prior to bone implantation, either manually or by using an inserter, such as the inserter 300 that includes a tip 302 and a hook 304 in which the sleeve can be supported in a folded, U-shape configuration with the strand 120 therethrough. Alternatively, and as illustrated in FIG. 9 in connection with the fixation member 200a, the fixation member 200a can first be implanted into bone 84. The tip 302 of the inserter 300 with the sleeve 100 thereon can be pushed through the aperture 210 of the fixation member 200a in the direction of arrow A.

Referring to FIG. 9 and in connection with the exemplary fixation member 200c, another method of securing the sleeve 100 to the fixation member 200c, after the fixation member 200c is implanted, is illustrated. Specifically, an auxiliary flexible member or string 250 in the form of a monofilament made of polyethylene, polyester, silk, or other biocompatible fiber or thin string-like material can be looped around the sleeve 100 and passed through the aperture 210 of the fixation member 200c. Pulling the auxiliary member 250 in the direction of arrow "B" causes the sleeve 100 and portion of the strand 120 to pass through the aperture 210 in a folded configuration. The auxiliary member 250 can be then pulled out and completely removed from the sleeve 100 and fixation member 200c. The sleeve 100 can be secured to the fixation member 200c in a bunched-up (ball or bell-like) configuration by pulling on the ends 122, 124 of the strand loop 128 to shorten the loop 128, as described above. In another aspect, the auxiliary flexible member 250 can be looped through openings 150, 152 of the sleeve 100, as shown in FIG. 1B.

With continued reference to FIG. 9, fixation member 200d is shown implanted in bone bore 86 with the sleeve 100 shown in a bunched-up (ball or bell-like) configuration. Another fixation member 200d' is illustrated before implantation into the bone bore 86. The fixation member 200d' can be coupled to a cannulated or other fixation-member inserter 270 for insertion through an incision or other opening 82 in soft tissue 80 and into a bone bore 86. The opening 82 can be pre-formed with another surgical instrument or by the pointed tip 202 of the fixation member 200d' as it is pushed through the soft tissue 80. Similarly, the bone bore 86 can be pre-formed, or created by the threaded fixation member 200d' as it is threadably inserted into the bone 84. An auxiliary member 250 can be used to manipulate the sleeve 100 and secure the sleeve 100 into the fixation member 200d', as described above in connection with fixation member 200c. The auxiliary member 250 can be looped around the sleeve 100 and passed through the eyelet 204 into the bore 212 and out of the aperture 210 at the proximal end 206. The sleeve 100 can be pulled through the eyelet 204, the bore 212 and aperture 210 by pulling the auxiliary member 250 in the direction of the arrow B either before or after implantation of the fixation member 200d' into the bone 84.

After all the sleeves 100 have been secured to the corresponding fixation members 200, the single loop 128 is tightened by pulling one of the strand ends 122, 124 relative to slipknot 130. In this manner, tissue to tissue attachment in multiple locations without the need of individual knots for each location is conveniently performed, thus avoiding the need of tying individual knots through cannulas for each fixation member 200. The procedure can be used for any tissue to tissue attachment, including, but not limited to, various arthroscopic procedures, such as, for example, rotator cuff repair, acromioclavicular reconstruction, and other procedures for which multiple anchor fixation can be beneficial. The procedure can be performed efficiently by simply passing by pulling or pushing the connector device 101 through an aperture or eyelet of the anchor or other fixation member 200 in one direction and then tensioning or pulling the strand 120 of the connector device 101 in the another direction for a knotless attachment of the strand 120 to the fixation member 200. The pull-out strength of the attachment can be a function of the strand size, but greater than using a mere strand with a knot.

Generally, and described above, the connector device 101 including one or more sleeves 100 can be to secure a strand 120, such as a suture to soft tissue 80 or bone, and to attach soft tissue to bone. Any of the connector devices 101 illustrated in FIGS. 1, 1A, 1B and 1C, can be used with or without a fixation member 200 and with or without an inserter 300 and with or without an auxiliary member 250 for manipulation the sleeve 100, although only the connector 101 of FIG. 1 is shown in the exemplary illustrations of FIGS. 4-9. Accordingly, a fixation assembly kit can be provided that includes, for example, a plurality of sleeves 100, a cartridge of continuous stand 120 or separate pieces of strand 120, a cartridge or separate pieces of auxiliary member material, one or more inserters, various fixation members 200, and one or more fixation member inserters 270. The sleeves 100 and strand 120 can be provided preloaded on one or more inserters 300. When a fixation member 200 is used, the fixation member 200 can be provided preloaded on a fixation member inserter 270. The connector device 101 allows tissue to tissue attachment in multiple locations without the need of individual knots for each location. After multiple-location attachment is performed, the single loop 128 is tightened by pulling one of the strand ends 122, 124 relative to slipknot 130.

With general reference to FIGS. 10A-15, shown is a fastener 300 which is coupled to a bore 302 defined within a bone 304. The fastener 300 defines a suture accepting aperture 306 and a suture accepting channel 308. In this regard, the suture accepting channel 308 is defined on an exterior surface of the fastener 300 and can intersect the aperture 306. Coupled to the fastener 300 is a suture construction 310 as previously described.

The fastener 300 has an exterior surface having a bone engaging flange 313. This bone engaging flange 313 can be a helical thread which circumscribes a central axis 319 defining the fastener 300. The suture construction 310 is fed in a first direction through the suture accepting aperture 306. Optionally, defined adjacent a suture bearing surface 317 of the fastener 300, is a portion of the suture accepting aperture having a restricted diameter 316. As will be described further below, the restricted diameter 316 and bearing surface 317 are configured to engage first and second ends of the flexible sleeve 312 to facilitate the collapsing or change in cross-section of the flexible sleeve 312 when the flexible sleeve 312 is pulled in a second direction. This allows the locking engagement of the suture construction 310 to the fastener 300.

Shown in FIGS. 10A-11B are fasteners 300 engaged within the bore 302 in bone 304. Shown are sutures 310 fed through the suture accepting aperture 306 and then through the channel 308 which is defined in the exterior surface of the fastener 300 and/or within the bone engaging flange 313. As shown in FIGS. 12A-15, the flexible sleeve can be positioned within the suture accepting channel 308 prior to the insertion of the fastener 300 within the bore 302 defined in the bone 304. Upon application of tension to the single or multiple suture strands 310, the suture can be translated in the second direction through the aperture 306 having a restricted diameter 316 to cause engagement of and subsequent collapsing of the flexible sleeve 312. This collapsed sleeve 312 has a second cross-section which allows for the interference of the threads within the bore 302 defined in the bone 304, thus restricting the rotation of the fastener 300 within the bore 302. Further, the collapsing of the tube 312 allows for the fixing of the suture 310 to the fastener 300.

Figure 14:
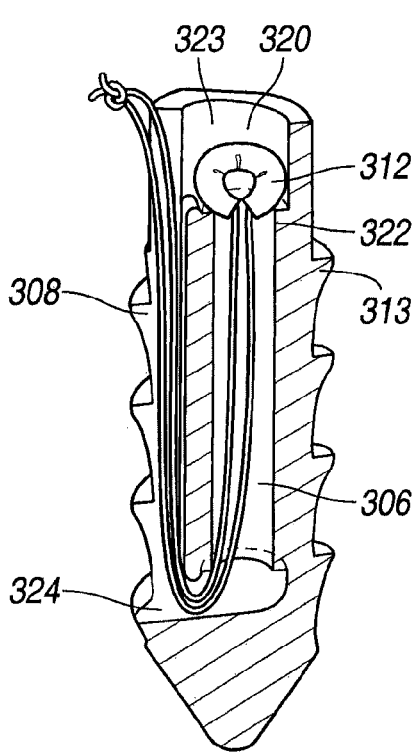
Figure 15:
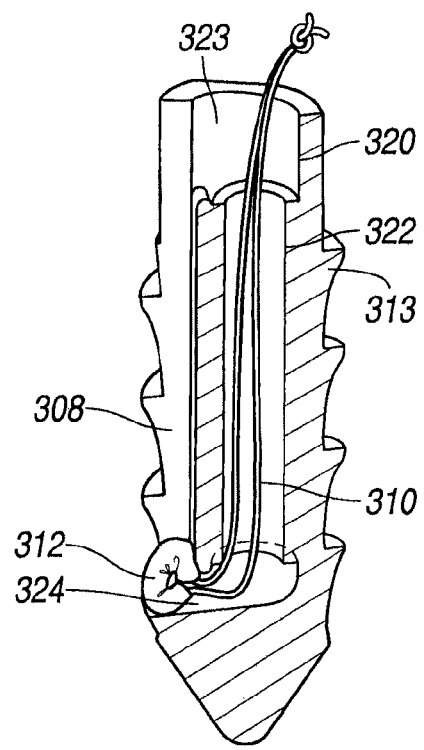
Figure 16A:
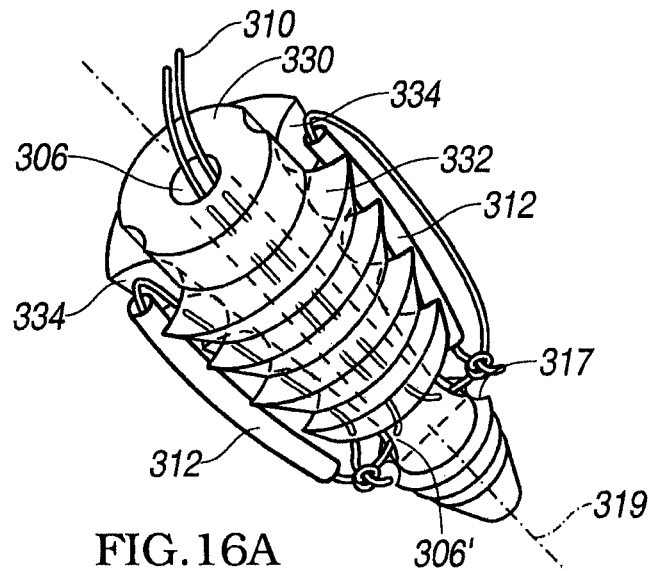
FIGS. 16A-18C represent alternate fasteners and suture constructions according to the teachings of one embodiment.
Figure 16B:
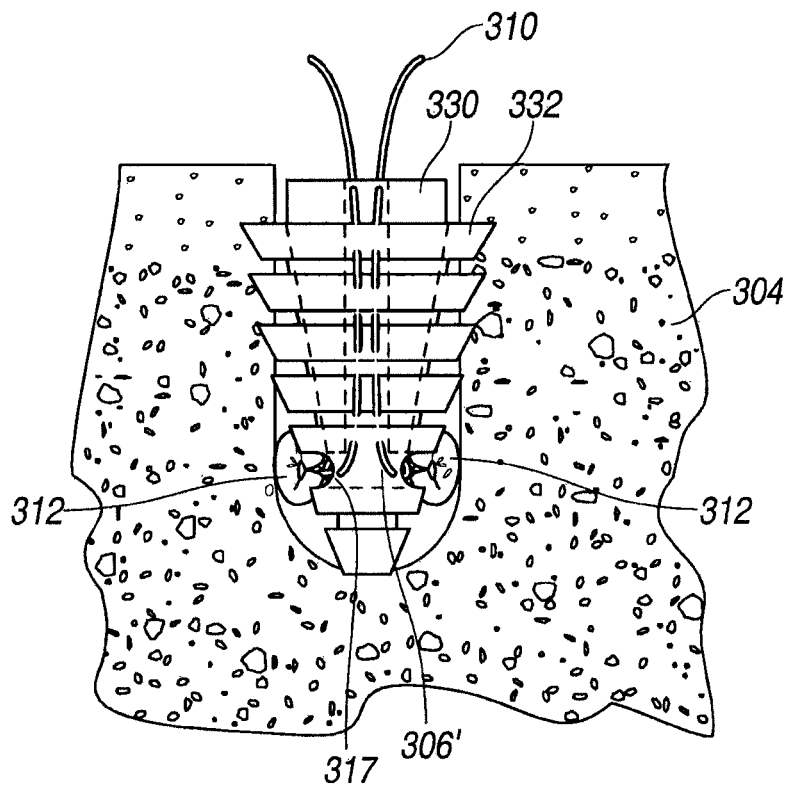
Figure 17:
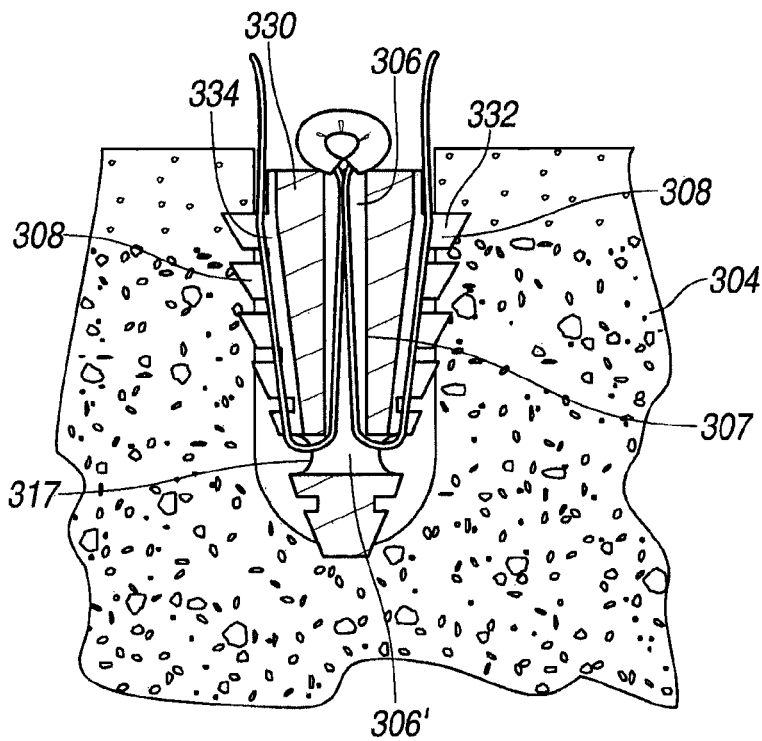
Figure 18A:
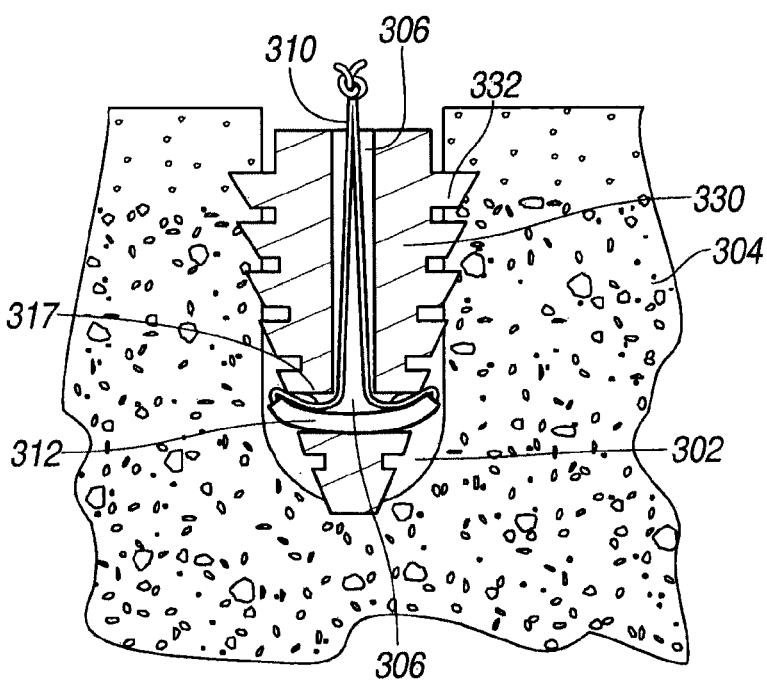
Figure 18B:
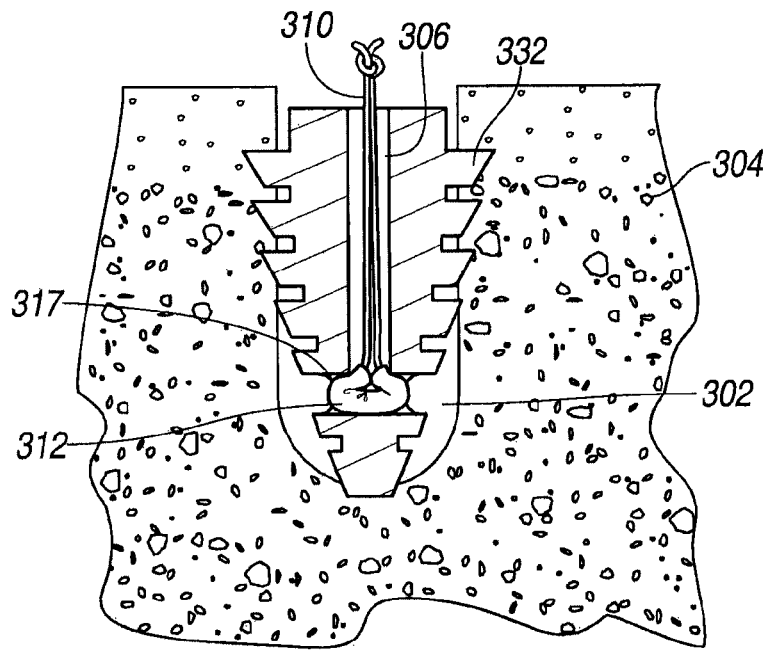
Figure 18C:
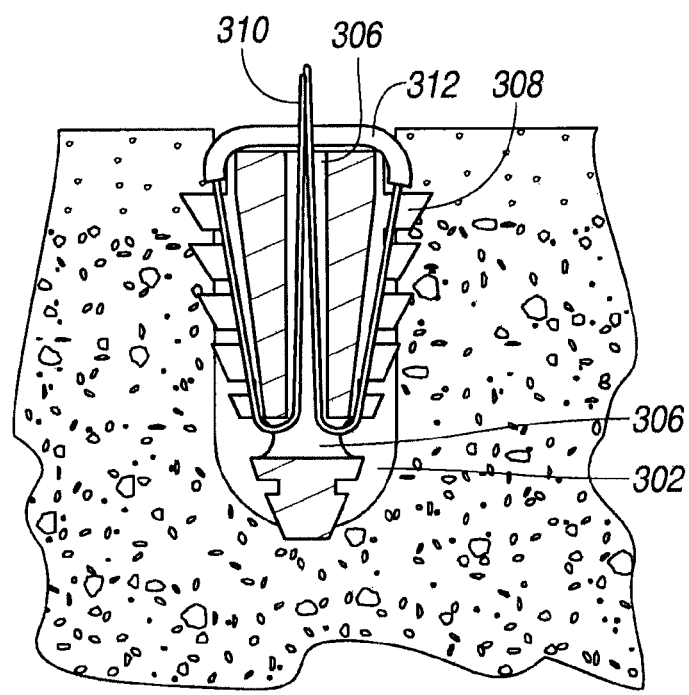

As best seen in FIGS. 14 and 15, the suture accepting aperture 306 can have various profiles. In this regard, the suture accepting aperture 306 can have a first portion having a first diameter 320 and a second portion 322 having a second diameter smaller than the first portion. This first portion 320 can define a chamber 323 which functions to accept the collapsed flexible sleeve. Additionally, the channel 308 can be sized so as to allow the collapse of the flexible sleeve 312 in a manner which would not restrict the rotation of the fastener 300 within the bore 302 defined within the bone. Drive surfaces can additionally be formed within the chamber 323.

With general reference to FIGS. 16A-18C, shown are an alternate fastener 330 which is used to couple suture 310 to a bone 304. The fastener 330 has a central suture accepting aperture 306 which is generally defined along a central axis 319 of the fastener 330. Additionally, defined generally perpendicular to the center line of the fastener is a second suture accepting aperture 306'. The fastener 330 has a plurality of bone engaging flanges 332 which are radially disposed about the central axis 319. The bone engaging flanges 332 can be formed generally perpendicular to the central axis 319.

As best seen in FIGS. 16B-18B, the fastener 330 can have a generally conical shape to facilitate the insertion of the fastener 330 within the bore 302. This conical shape can also be defined on the exterior surface of the bone engaging flanges 332. Defined within the bone engaging flanges 332 or an exterior surface of the fastener 330 can be a pair of suture or flexible sleeve accepting channels 334. Prior to insertion of the fastener 330 into the bore 302, either of the suture and/or a non-compressed flexible sleeve 312 can be positioned within the channels 334.

The fastener 330 can be liner or rotatably inserted into the bore 302. After insertion of the fastener 330 within the bore 302, tension is applied to one or more of the suture strands 310 to cause the movement of the flexible sleeve 312 in a first direction. This causes the flexible sleeve 312 to engage a bearing surface 317 of the fastener 330. The engagement of the flexible sleeve 312 with the bearing surface 317 causes the collapse of the flexible sleeve as been previously described. This functions to lock the suture 310 to fastener 330 and to increase retention forces between the fastener 330 and the bore 302.

Figure 19A:
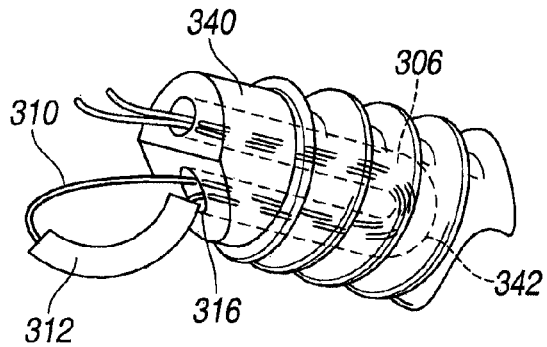
FIGS. 19A-20 represent an alternate fastener and suture construction.
Figure 19B:
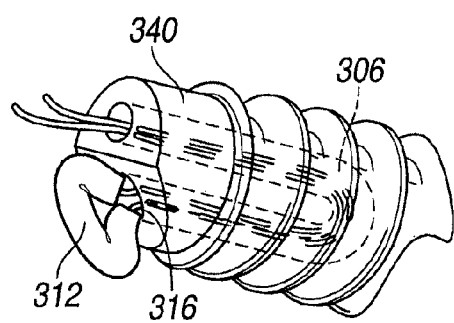
Figure 19C:
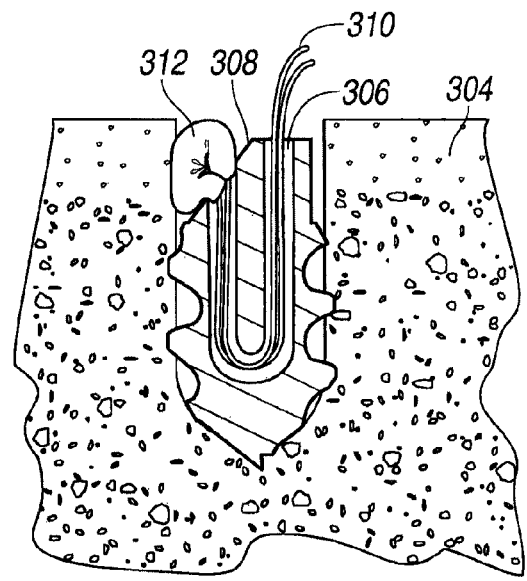
Figure 20:
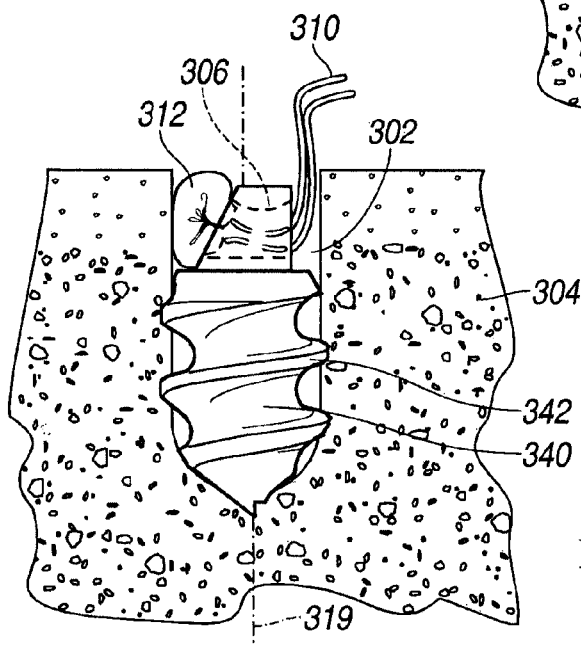
Figure 21:
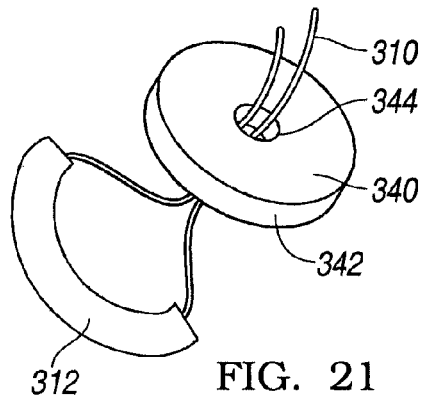
FIGS. 21-24 represent an alternate fastener and suture construction according to the present teachings.
Figure 22:
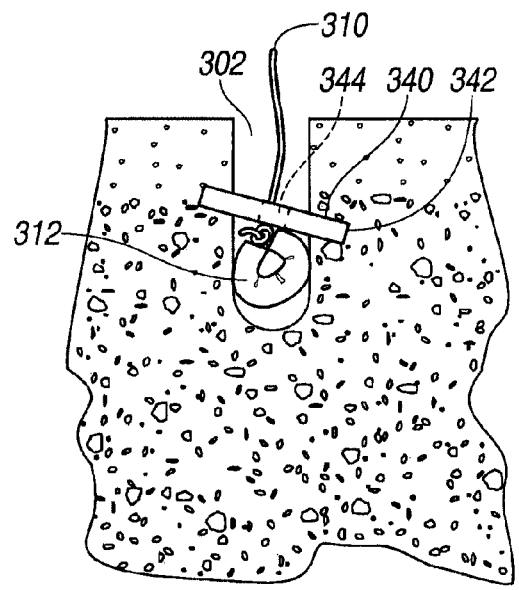
Figure 23:
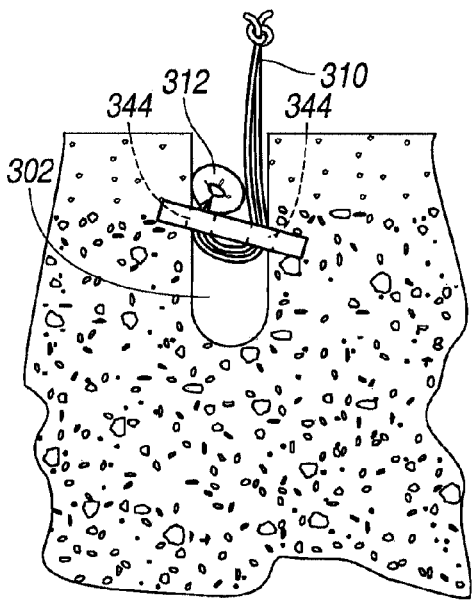
Figure 24:
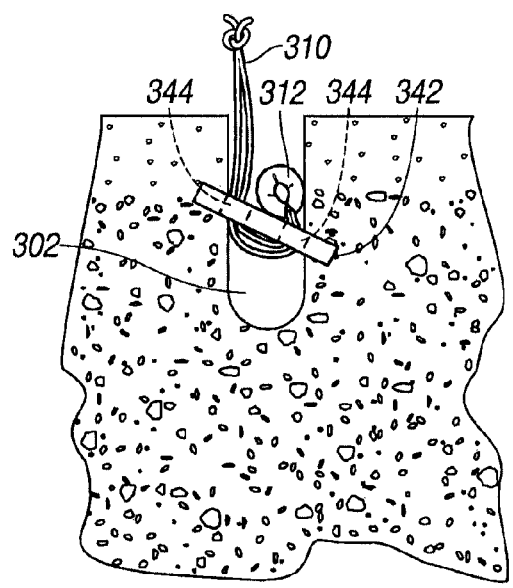

FIGS. 19A-20 represent an alternate fastener 340 coupled to a suture 310. The fastener 340 has a suture accepting bore 306 defined therein. This bore 306 can have portions which are parallel to and/or perpendicular to a central axis 319 defining the fastener body. The exterior of the fastener defines a channel or cutout 308 which functions to accept the collapsible sleeve 312 threaded onto the suture 310. This cutout 308 can be accessible through the bore 302 once the fastener 340 is inserted.

FIGS. 19C and 20 depict cross-sectional and side views of the fastener 340 inserted within a bore 302 defined within bone 304. Once tension is applied to the collapsible sleeve 312 and suture 310, the sleeve 312 is pulled into a pocket defined by the channel or cutout 308. This collapsible sleeve 312 can bear upon an interior surface of the bore 302 as well as the channel or cutout 308 to lock a suture 310 to the fastener 340, as well as aid in the fixation of construct in bone. Also shown are bone engaging flanges 342 which couple the fastener to bone 304.

As seen in FIGS. 21-24, an alternate anchor 340 is positioned within an aperture 302. The anchor 340 is rotated within the aperture 302 to engage the bone. Application of tension to an end or ends of the suture 310 can cause the anchor 340 to rotate and engage the bone. The alternate suture anchor 340 is coupled to a suture 310 and a collapsible sleeve 312. Optionally, the anchor 340 can take the form a generally flat cylinder or tube having a bone engaging surface 342 and a suture accepting bore 344 therethrough. While shown as a disk, it is envisioned the anchor 340 can have an elongated profile.

Application of tension to an end or ends of the suture construction 310 can cause the anchor 340 to rotate and engage the bone and to cause the collapse of the flexible sleeve 312. This fixably couples the suture 310 to the anchor 340 as well as the bone 304.

Figure 25A:
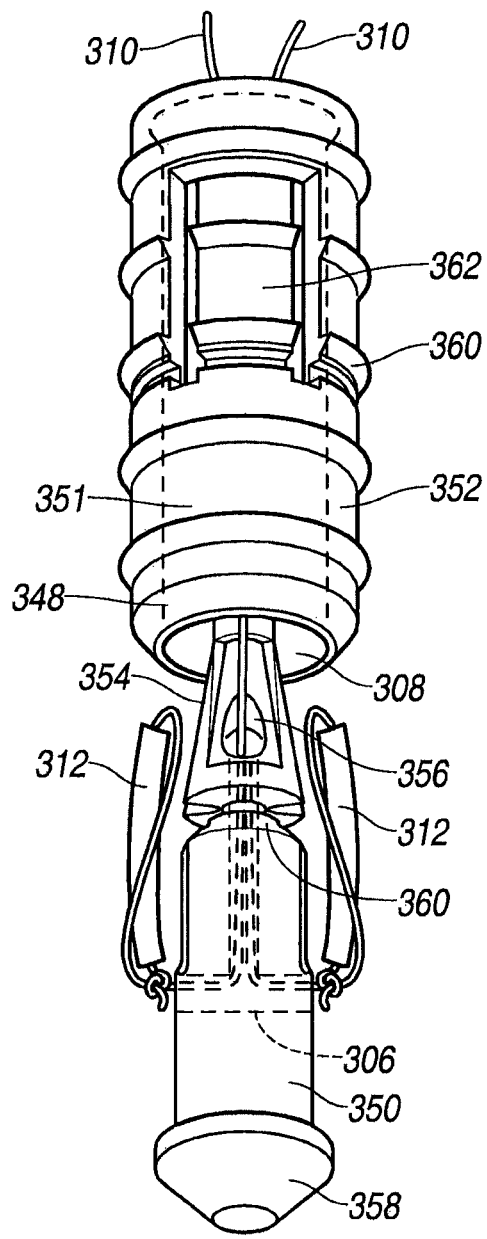
FIGS. 25A and 25B represent two-part fasteners and suture construction.
Figure 25B:
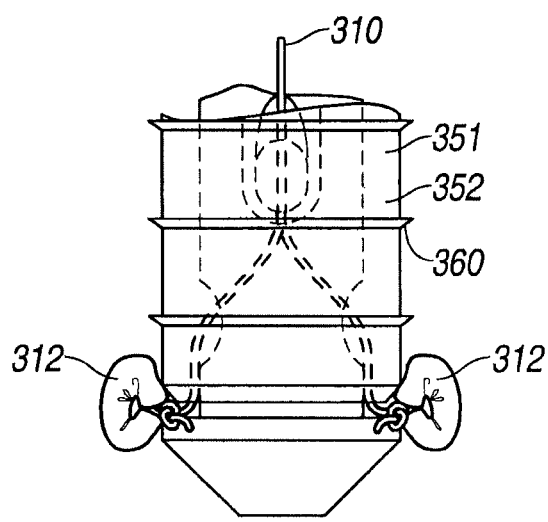

FIGS. 25A and 25B represent a fastener 348 having first and second portions 350, 352. Additionally shown is an insertion tool 354 which is used to facilitate the first and second fastener portions 350, 352 into an aperture 302 defined within a bone 304. The first portion of the fastener 348 has a head 358 which can have a generally conical shape. Additionally, the head 358 can have a bearing surface which functions, to constrain the movement of the suture construction 310 and/or the collapsible flexible tube 312.

The second fastener portion 352 has an interior portion 308 which can facilitate the acceptance of the flexible sleeve 312. Defined on an outer surface of the second portion 352 can be a plurality of bone engaging flanges 360. Optionally, the second portion can have an expandable member 362 which facilitates the engagement of the flanges 360 into the bone 304 upon the coupling of the first and second portions 350, 352. For installation, a central tool 354 has a pair of apertures with suture ends 310 threaded therethrough. The suture 310 can have a pair of flexible sleeves 312 being mounted thereon. These flexible sleeves 312 are optionally threaded through the suture accepting bore 306 defined within the first portion 350 of the two portion fastener 348.

FIG. 25B represents an assembled two component fastener 348 shown in FIG. 25A. In this regard, the first portion 350 is disposed within the central aperture 351 in the second portion fastener 352. As can be seen, the suture 310 is disposed between the first and second portions 350, 352. Application of tension to the suture 310 causes the collapse of the flexible sleeve 312 and associated locking of the suture construction 310 to the fastener 348.

Figure 26A:
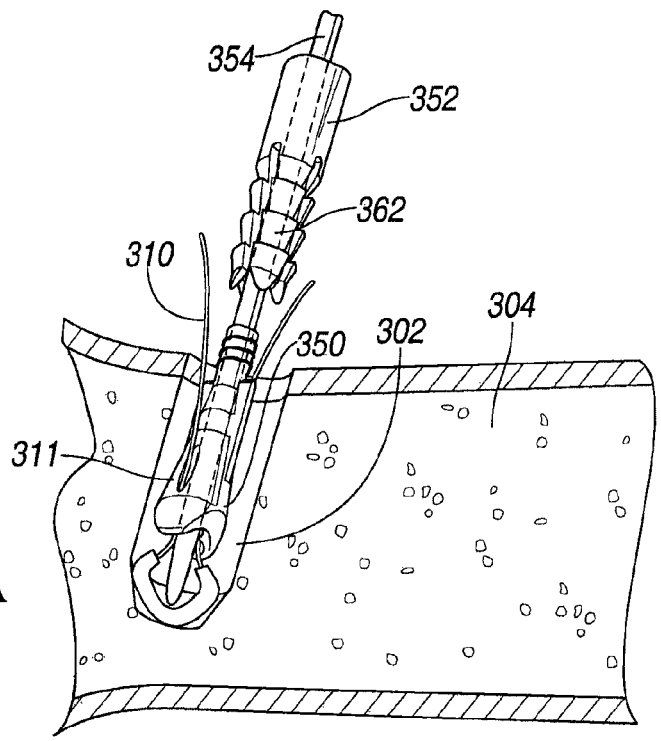
FIGS. 26A-26C represent the insertion of the fastener shown in FIGS. 25A and 25B.

With general reference to FIGS. 26A-27, shown is the insertion of a two-part fastener 348 according to the present teachings. Shown is the first portion 350 having a tapered smooth exterior surface, and a second fastener portion 352 having a plurality of movable bone engaging flanges 362. A pair of apertures 306 defined within the first fastener 350 accept the suture 310 and flexible sleeve 312.

Figure 26B:
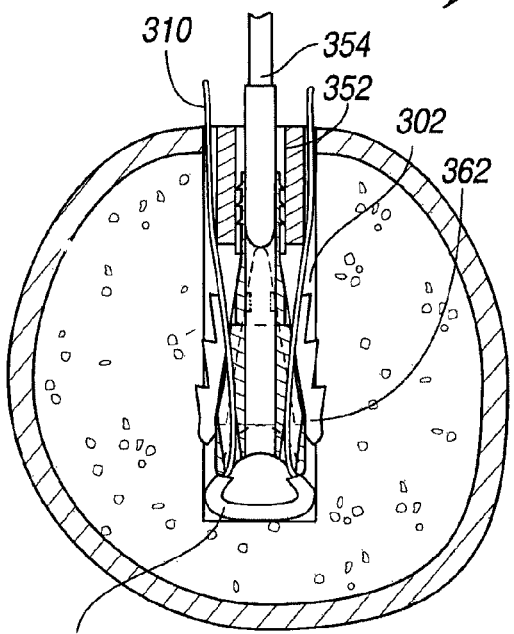
Figure 26C:
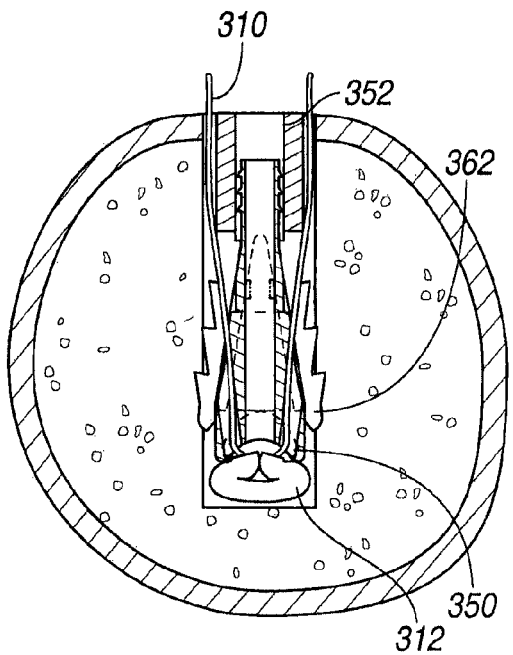

As best shown in FIGS. 26B and 26C, the first and second portions of the fastener 350, 352 are fed over an insertion tool 354. Disposed on the first portion 350 of the fastener 348 is a suture 310 having the flexible sleeve 312 threaded thereon. Threaded through an optional pair of apertures 311 within the first fastener portion 350 is a pair of ends of the suture 310. These ends are then threaded through a central bore or a slot defined in the second fastener portion 352.

After the insertion of the fastener 348 into a bore 302 defined within the bone 304, the second fastener portion 302 is coupled to the first fastener portion 305. This coupling optionally causes an expansion of the bone engaging flanges 362. Tension can be applied to the ends of the suture 310 to cause the compression of the flexible member 312. This collapsing of the flexible member can then lock the suture 310 to the first and/or second portions of the fastener 350, 352.

The foregoing discussion discloses and describes merely exemplary arrangements. One skilled in the art will readily recognize from such discussion, and from the accompanying drawings and claims, that various changes, modifications and variations can be made therein without departing from the spirit and scope of the present teachings as defined in the following claims. For example, multiple fixation members can be inserted in bone and can be coupled to suture anchors as described. The suture anchors can be coupled to the anchors before or after the anchors are coupled to the bone.

What is claimed is:

1. A method for securing a flexible strand to at least one fixation member for a surgical procedure, the method comprising:

passing a flexible sleeve through a hole in the at least one fixation member in a first configuration;

positioning the at least one fixation member, having the flexible strand passing through the fixation member from a first side to a second side of the fixation member and through the flexible sleeve on the first side of the fixation member, into a bore formed into tissue; and tensioning the flexible strand on the second side of the fixation member to deform the flexible sleeve to a second configuration to prevent the flexible sleeve from passing through the hole and cause the fixation member to rotate in the bore.

2. The method of claim 1, further comprising forming the bore in the tissue, where the tissue is bone.

3. The method of claim 1, wherein tensioning the flexible strand includes tensioning first and second ends of the flexible strand on the second side of the fixation member to deform the flexible sleeve on the first side of the fixation member and cause the fixation member to rotate in the bore such that a tissue engaging surface of the fixation member engages the bore.

4. The method of claim 1, wherein the fixation member is disk-shaped and defines a hole passing through the disc-shaped fixation member.

5. The method of claim 1, wherein positioning at least the one fixation member into the bore formed into tissue includes moving the fixation member in a first direction with the flexible sleeve in a first configuration and wherein tensioning the flexible strand includes moving the flexible strand in a second opposite direction to deform the flexible sleeve to a second configuration.

6. A method for securing a flexible strand to at least one fixation member for a surgical procedure, the method comprising:

forming a bore in tissue and forming a bore in bone;

positioning a flexible sleeve attached to a flexible strand and the fixation member into the bore; and tensioning the flexible strand to deform the flexible sleeve and cause the fixation member to rotate in the bore;

wherein the fixation member includes a disk-shaped member having a bone-engaging surface about the disk-shaped member, wherein upon rotating the fixation member in the bore, the bone-engaging surface engages the bone to secure the flexible strand relative to the bone.

7. The method of claim 6, wherein the fixation member is a disk-shaped fixation member defining a hole passing therethrough, wherein the method further includes passing the flexible sleeve through the hole in the disk-shaped fixation member in a first configuration and wherein tensioning the flexible strand deforms the flexible sleeve to a second configuration.

8. The method of claim 6, wherein the flexible sleeve is on a first side of the fixation member and an end of the flexible strand is on an opposite side of the fixation member, wherein upon tensioning the flexible strand on the second side of the fixation member, the flexible sleeve on the first side of the fixation member deforms.

9. The method of claim 6, wherein the fixation member defines a first hole and a second hole passing through the fixation member from a first side of the fixation member to a second side of the fixation member, wherein the flexible sleeve and ends of the flexible strand are on the first side of the fixation member upon tensioning the flexible strand.

10. The method of claim 6, wherein the flexible sleeve has first and second ends and first and second ends of the flexible strand exit the sleeve from corresponding first and second openings of the sleeve.

11. The method of claim 10, wherein the corresponding first and second openings of the sleeve are at the first and second ends of the sleeve.

12. A method for securing a flexible strand to at least one fixation member, the method comprising:

providing a disk-shaped fixation member having a tissue-engaging surface and defining at least one hole extending through the disk-shaped fixation member from a first side to a second side of the disk-shaped fixation member;

passing at least a portion of the flexible strand having first and second ends through at least a portion of a longitudinal bore of a flexible sleeve such that the first and second ends of the flexible strand are outside the flexible sleeve;

positioning the flexible strand through the hole in the disk-shaped fixation member such that the flexible sleeve is positioned on the first side of the disk-shaped fixation member and at least the first end of the flexible strand extends from the disk-shaped fixation member; and positioning the flexible sleeve attached to the flexible strand and the disk-shaped fixation member into a bore formed in bone.

13. The method of claim 12, wherein the at least first end of the flexible strand extends from the second side of the disk-shaped fixation member.

14. The method of claim 12, wherein the disk-shaped fixation member defines a second hole extending through the disk-shaped fixation member from the first side to the second side of the disk-shaped fixation member, the method further comprising passing the flexible strand through the second hole in the disk-shaped fixation member.

15. The method of claim 12, further comprising tensioning the flexible strand to deform the flexible sleeve and cause the disk-shaped fixation member to rotate in the bore.

16. The method of claim 15, wherein positioning the flexible sleeve on the first side of the fixation member includes deforming the flexible sleeve into a first configuration and passing through the hole, wherein tensioning the flexible strand includes tensioning the flexible strand to change the sleeve to a second configuration that cannot re-enter the hole.

\* \* \* \* \*